(12) United States Patent
Teisen

(10) Patent No.: US 12,350,166 B2
(45) Date of Patent: *Jul. 8, 2025

(54) METHOD AND APPARATUS FOR AUGMENTING BONE

(71) Applicant: DePuy Synthes Products, Inc., Raynham, MA (US)

(72) Inventor: Jacques Teisen, Zurich (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/156,458

(22) Filed: Jan. 19, 2023

(65) Prior Publication Data

US 2023/0149058 A1 May 18, 2023

Related U.S. Application Data

(60) Continuation of application No. 16/566,949, filed on Sep. 11, 2019, now Pat. No. 11,576,704, which is a
(Continued)

(51) Int. Cl.
*A61F 2/44* (2006.01)
*A61B 17/16* (2006.01)
(Continued)

(52) U.S. Cl.
CPC .......... *A61F 2/441* (2013.01); *A61B 17/1671* (2013.01); *A61B 17/7097* (2013.01);
(Continued)

(58) Field of Classification Search
CPC . A61F 2/441; A61F 2002/448; A61B 17/7097
See application file for complete search history.

(56) References Cited

U.S. PATENT DOCUMENTS

| | | | |
|---|---|---|---|
| 5,059,193 A | 10/1991 | Kuslich | |
| 5,772,681 A | 6/1998 | Leoni | |

(Continued)

FOREIGN PATENT DOCUMENTS

| | | |
|---|---|---|
| CA | 2599009 A1 | 9/2006 |
| CN | 101442963 A | 5/2009 |

(Continued)

OTHER PUBLICATIONS

U.S. Appl. No. 16/566,949, filed Sep. 11, 2019.
(Continued)

*Primary Examiner* — Andrew Yang
(74) *Attorney, Agent, or Firm* — BakerHostetler

(57) ABSTRACT

An expandable implant system is configured to increase the height of a target bone, for instance that has been subjected to a compression fracture. The expandable implant system includes an implant assembly that can be inserted into the target bone, and subsequently expanded so as to increase the height of the target bone. The expandable implant system further includes an and insertion assembly that is configured to create an insertion channel into the target bone, such that the implant assembly can be inserted in a collapsed configuration into the target bone along the insertion channel, and subsequently expanded.

20 Claims, 33 Drawing Sheets

Related U.S. Application Data continuation of application No. 15/977,454, filed on May 11, 2018, now Pat. No. 10,413,340, which is a continuation of application No. 14/700,255, filed on Apr. 30, 2015, now Pat. No. 9,987,055, which is a division of application No. 12/859,732, filed on Aug. 19, 2010, now Pat. No. 9,247,970.

(60) Provisional application No. 61/235,196, filed on Aug. 19, 2009.

(51) Int. Cl.
*A61B 17/70* (2006.01)
*A61B 17/88* (2006.01)

(52) U.S. Cl.
CPC ...... *A61B 17/8872* (2013.01); *A61B 17/1642* (2013.01); *A61B 17/1662* (2013.01)

(56) References Cited

U.S. PATENT DOCUMENTS

| | | | |
|---|---|---|---|
| 6,127,597 | A | 10/2000 | Beyar et al. |
| 6,224,603 | B1 | 5/2001 | Marino |
| 6,478,823 | B1 | 11/2002 | Michelson |
| 6,582,467 | B1 | 6/2003 | Teitelbaum et al. |
| 6,632,235 | B2 | 10/2003 | Weikel et al. |
| 7,001,431 | B2 | 2/2006 | Bao et al. |
| 7,008,422 | B2 | 3/2006 | Foley et al. |
| 7,141,061 | B2 | 11/2006 | Williams et al. |
| 7,465,318 | B2 | 12/2008 | Sennett et al. |
| 7,601,172 | B2 | 10/2009 | Segal et al. |
| 7,618,457 | B2 | 11/2009 | Hudgins |
| 7,666,205 | B2 | 2/2010 | Weikel et al. |
| 7,842,040 | B2 | 11/2010 | Rabiner et al. |
| 7,879,041 | B2 | 2/2011 | Rabiner et al. |
| 7,988,735 | B2 | 8/2011 | Yurek et al. |
| 8,021,426 | B2 | 9/2011 | Segal et al. |
| 9,247,970 | B2 | 2/2016 | Teisen |
| 9,987,055 | B2 | 6/2018 | Teisen |
| 2003/0204189 | A1 | 10/2003 | Cragg |
| 2004/0092933 | A1 | 5/2004 | Shaolian et al. |
| 2004/0133280 | A1 | 7/2004 | Trieu |
| 2004/0167625 | A1 | 8/2004 | Beyar et al. |
| 2004/0186551 | A1 | 9/2004 | Kao et al. |
| 2005/0027358 | A1 | 2/2005 | Suddaby |
| 2005/0070913 | A1 | 3/2005 | Milbocker et al. |
| 2005/0209629 | A1 | 9/2005 | Kerr et al. |
| 2005/0261684 | A1 | 11/2005 | Shaolian et al. |
| 2005/0261781 | A1 | 11/2005 | Sennett et al. |
| 2006/0004437 | A1 | 1/2006 | Jayaraman |
| 2006/0025861 | A1 | 2/2006 | McKay |
| 2006/0100706 | A1 | 5/2006 | Shadduck et al. |
| 2006/0161164 | A1* | 7/2006 | Hwang .............. A61B 17/7097 606/86 R |
| 2006/0184188 | A1 | 8/2006 | Li et al. |
| 2006/0271061 | A1 | 11/2006 | Beyar et al. |
| 2006/0287726 | A1 | 12/2006 | Segal et al. |
| 2006/0287727 | A1 | 12/2006 | Segal et al. |
| 2007/0016191 | A1 | 1/2007 | Culbert et al. |
| 2007/0038301 | A1 | 2/2007 | Hudgins |
| 2007/0043440 | A1 | 2/2007 | William et al. |
| 2007/0088436 | A1 | 4/2007 | Parsons et al. |
| 2007/0093899 | A1 | 4/2007 | Dutoit et al. |
| 2007/0161991 | A1 | 7/2007 | Altarac et al. |
| 2007/0179610 | A1 | 8/2007 | Biedermann et al. |
| 2007/0255287 | A1 | 11/2007 | Rabiner |
| 2007/0260252 | A1 | 11/2007 | Schmitz et al. |
| 2007/0276491 | A1 | 11/2007 | Ahrens et al. |
| 2008/0071356 | A1 | 3/2008 | Greenhalgh et al. |
| 2008/0125784 | A1 | 5/2008 | Rabiner et al. |
| 2008/0208255 | A1 | 8/2008 | Siegal |
| 2008/0208320 | A1 | 8/2008 | Tan-Malecki et al. |
| 2008/0249481 | A1 | 10/2008 | Crainich et al. |
| 2008/0294205 | A1 | 11/2008 | Greenhalgh et al. |
| 2009/0024204 | A1 | 1/2009 | Greenhalgh et al. |
| 2009/0105809 | A1 | 4/2009 | Lee et al. |
| 2009/0177204 | A1 | 7/2009 | Colleran et al. |
| 2009/0187192 | A1 | 7/2009 | Rabiner et al. |
| 2009/0204216 | A1 | 8/2009 | Biedermann et al. |
| 2009/0299476 | A1 | 12/2009 | Diwan et al. |
| 2010/0121333 | A1 | 5/2010 | Crainich et al. |
| 2010/0286782 | A1 | 11/2010 | Schaller et al. |
| 2011/0028978 | A1 | 2/2011 | Li et al. |
| 2011/0046737 | A1 | 2/2011 | Teisen |
| 2011/0112643 | A1 | 5/2011 | Schwab |
| 2011/0264147 | A1 | 10/2011 | Culbert |

FOREIGN PATENT DOCUMENTS

| | | |
|---|---|---|
| CN | 101448471 A | 6/2009 |
| EP | 1265541 A4 | 5/2006 |
| EP | 1681021 A2 | 7/2006 |
| JP | 2006-507090 A | 3/2006 |
| JP | 2006-522612 A | 10/2006 |
| JP | 2008-531123 A | 8/2008 |
| WO | 2004/043271 A1 | 5/2004 |
| WO | 2004/047691 A1 | 6/2004 |
| WO | 2004/110300 A2 | 12/2004 |
| WO | 2005/027734 A2 | 3/2005 |
| WO | 2006/116761 A2 | 11/2006 |
| WO | 2007/076376 A2 | 7/2007 |
| WO | 2007/078692 A2 | 7/2007 |
| WO | 2009/064847 A2 | 5/2009 |
| WO | 2011/041038 A2 | 4/2011 |

OTHER PUBLICATIONS

U.S. Appl. No. 15/977,454, filed May 11, 2018.
U.S. Appl. No. 14/700,255, filed Apr. 30, 2015.
U.S. Appl. No. 12/859,732, filed Aug. 19, 2010.
International Patent Application No. PCT/US2010/033995: International Search Report dated Jul. 26, 2010, 8 pages.
U.S. Provisional Application filed Aug. 19, 2009 by Jacques Teisen, entitled "Augmentation of Fractured Bone, in Particular Vertebral Bodies", U.S. Appl. No. 61/235,196.

* cited by examiner

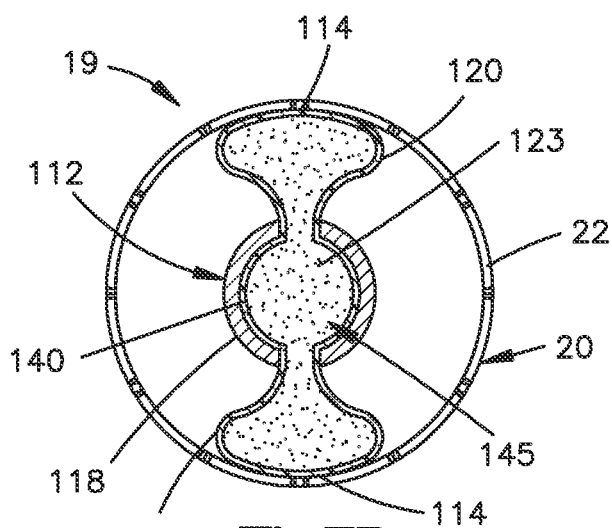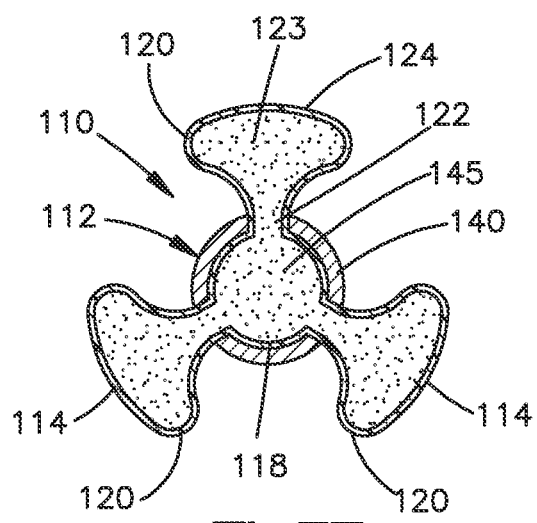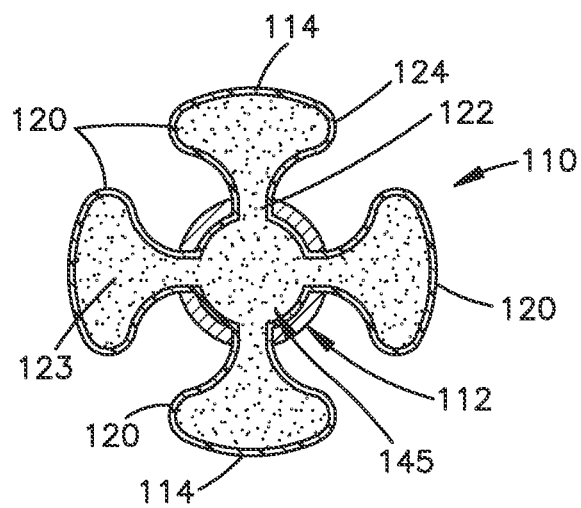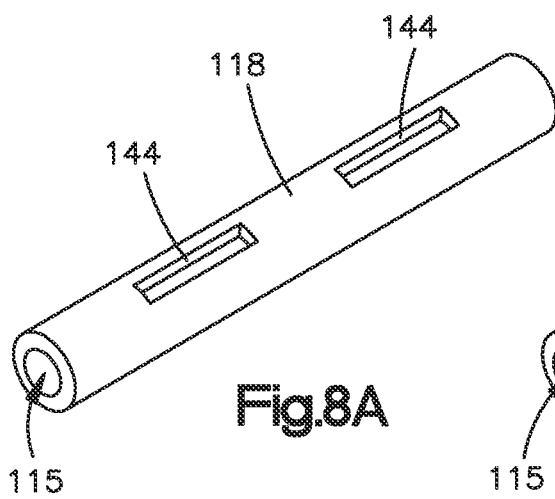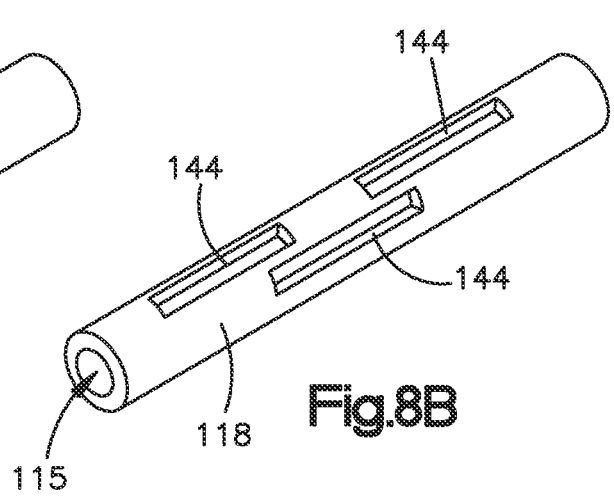

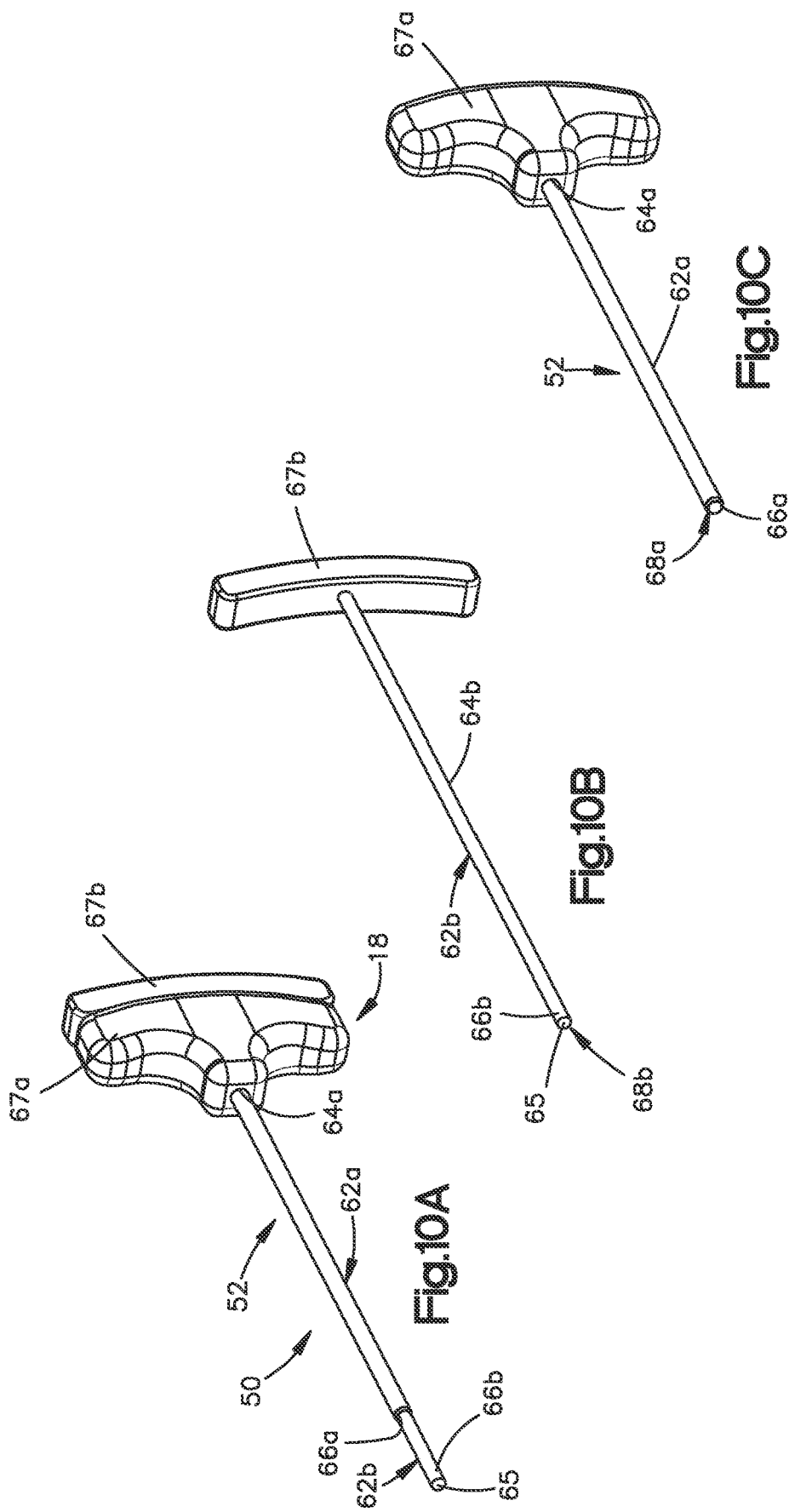

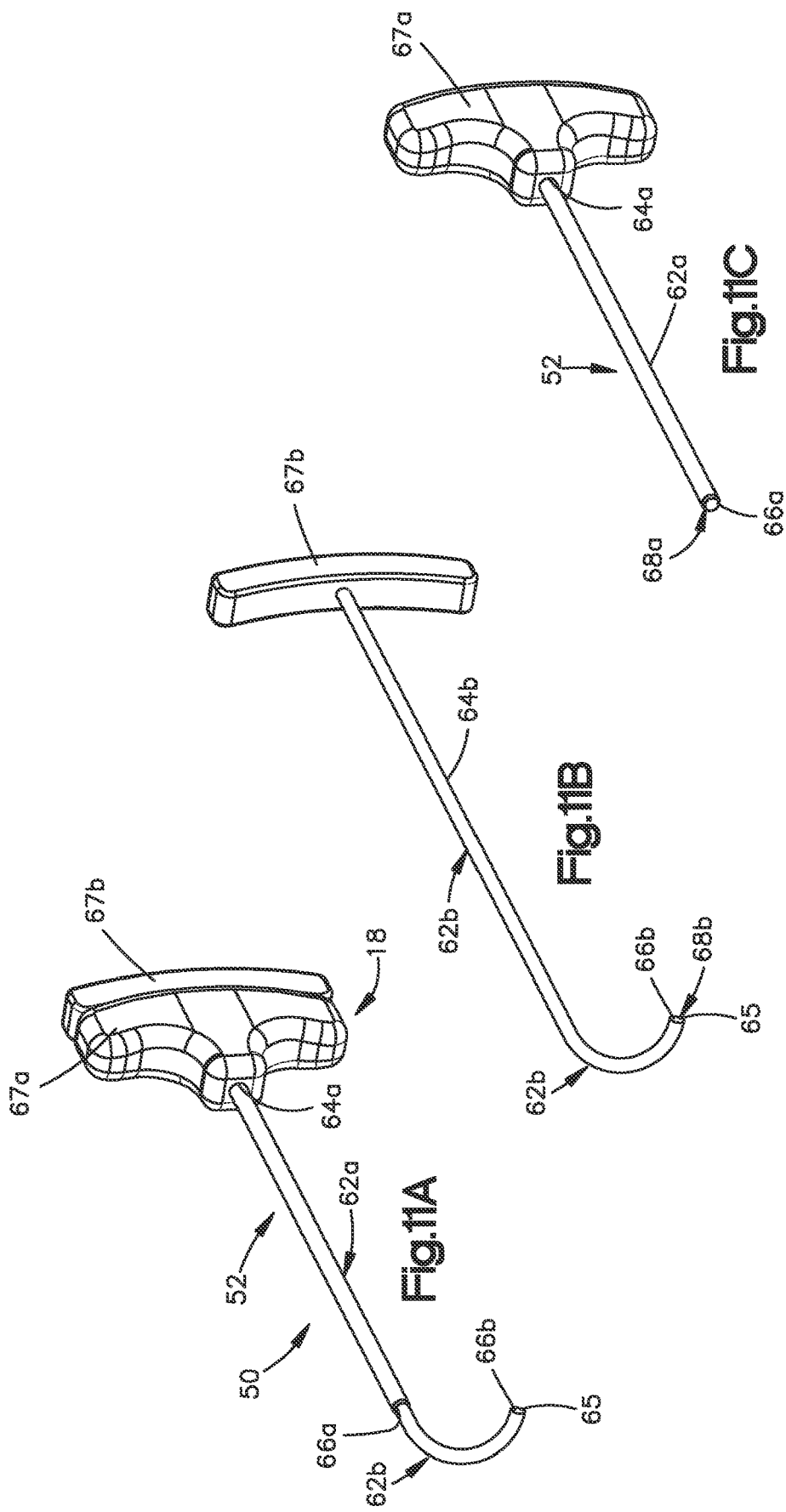

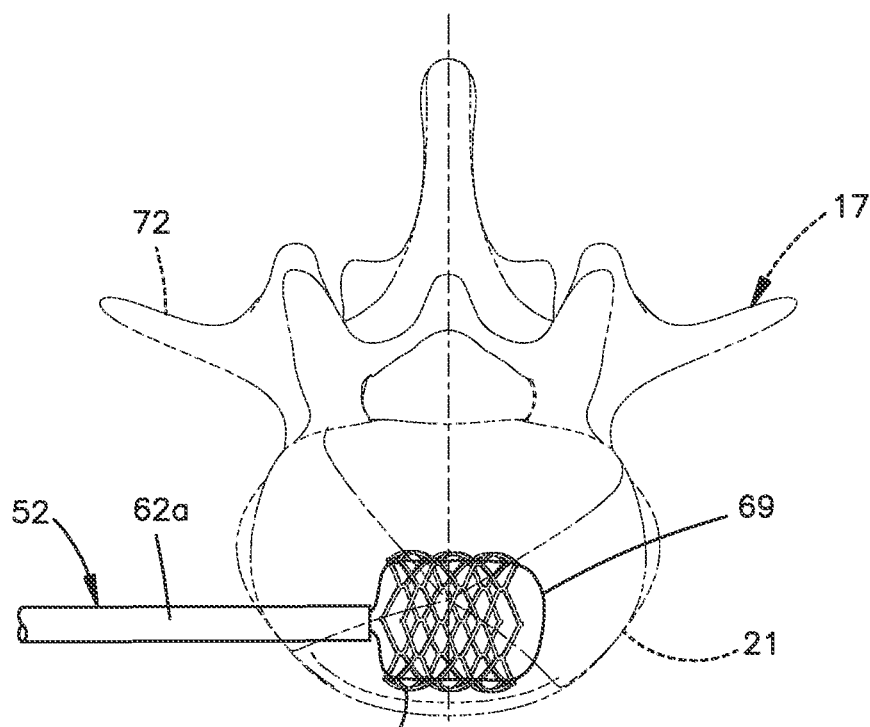
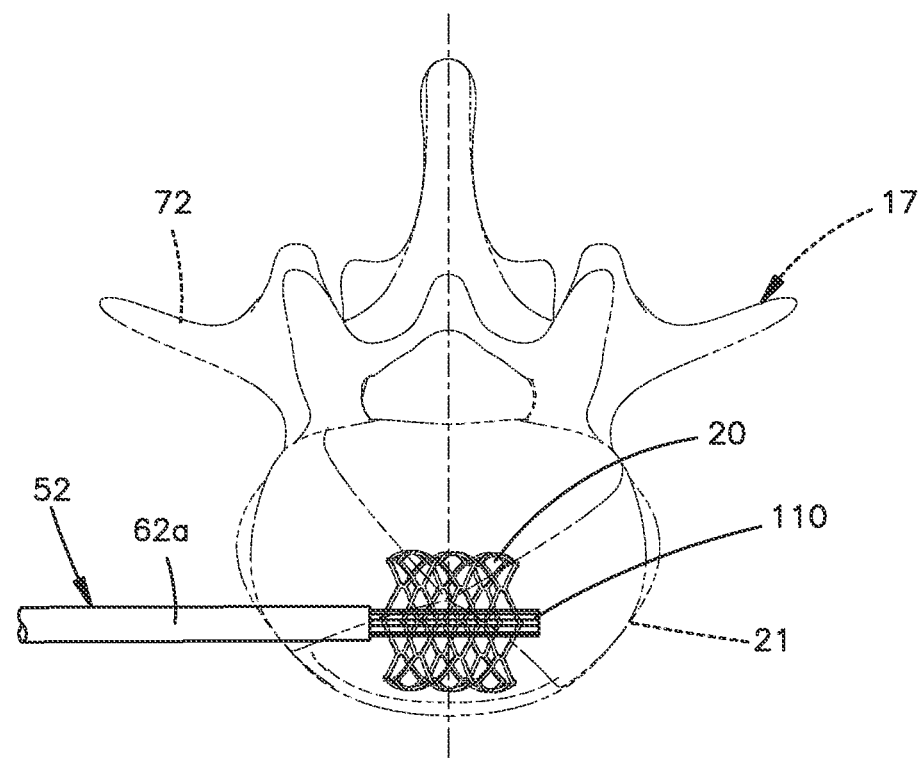

METHOD AND APPARATUS FOR AUGMENTING BONE

CROSS-REFERENCE TO RELATED APPLICATIONS

This application is a continuation of U.S. patent application Ser. No. 16/566,949, filed Sep. 11, 2019, which is a continuation of U.S. patent application Ser. No. 15/977,454, filed May 11, 2018, now U.S. Pat. No. 10,413,340, issued Sep. 17, 2019, which is continuation of U.S. patent application Ser. No. 14/700,255, filed on Apr. 30, 2015, now U.S. Pat. No. 9,987,055, issued Jun. 5, 2018, which is a divisional of U.S. patent application Ser. No. 12/859,732, filed on Aug. 19, 2010, now U.S. Pat. No. 9,247,970, issued Feb. 2, 2016, which claims the benefit of U.S. Provisional Patent Application Ser. No. 61/235,196, filed on Aug. 19, 2009. The entire disclosures of each application listed in this paragraph are hereby incorporated by reference into the present application as if set forth in their entirety herein.

TECHNICAL FIELD

The present disclosure relates generally to implant for augmenting or supporting bone, and in particular relates to expandable implants.

BACKGROUND

Vertebral compression fractures ("VCF") represent a common spinal injury and may result in prolonged disability. Generally speaking, VCF involves collapsing of one or more vertebral bodies in the spine. VCF usually occurs in the lower vertebrae of the thoracic spine or the upper vertebrae of the lumbar spine. VCF generally involves fracture of the anterior portion of the affected vertebral body. VCF may result in deformation of the normal alignment or curvature, e.g., lordosis, of the vertebral bodies in the affected area of the spine. VCF and/or related spinal deformities may result, for example, from metastatic diseases of the spine, from trauma or may be associated with osteoporosis. Until recently, doctors were limited in how they could treat VCF and related deformities.

Recently, minimally invasive surgical procedures for treating VCF have been developed. These procedures generally involve the use of a cannula or other access tool inserted into the posterior of the targeted vertebral body, usually through the pedicles.

In one such procedure, a cannula or bone needle is passed through the soft tissue of the patient's back. Once properly positioned, a small amount of polymethylmethacrylate (PMMA) or other orthopedic bone cement is pushed through the needle into the targeted vertebral body. This technique may be effective in the reduction or elimination of fracture pain, prevention of further collapse, and a return to mobility in patients. However, this technique typically does not reposition the fractured bone into its original size and/or shape and, therefore, may not address the problem of spinal deformity due to the fracture.

Other treatments for VCF generally involve two phases: (1) reposition or restoration of the original height of the vertebral body and consequent lordotic correction of the spinal curvature; and (2) augmentation or addition of material to support or strengthen the fractured or collapsed vertebral body.

One such treatment involves inserting, through a cannula, a catheter having an expandable member into an interior volume of a fractured vertebral body, wherein the interior volume has a relatively soft cancellous bone surrounded by fractured cortical bone therein. The expandable member is expanded within the interior volume in an attempt to restore the vertebral body towards its original height. The expandable member is removed from the interior volume, leaving a void within the vertebral body. PMMA or other bone filler material is injected through the cannula into the void to stabilize the vertebral body. The cannula is then removed and the cement cures to augment, fill or fix the vertebral body.

Another approach for treating VCF involves inserting an expandable mesh graft bladder or containment device into the targeted vertebral body. The graft bladder remains inside the vertebral body after it is inflated with PMMA or an allograft product.

It is desirable in the art to provide a safe and effective apparatus and method for aiding and/or augmenting fractured or otherwise damaged vertebral bodies and other bones.

SUMMARY

In accordance with one embodiment, an expandable implant system is configured to increase the height of a fractured target bone. The expandable implant system includes a primary implant and an auxiliary implant. The primary implant includes a primary implant body configured to move from a collapsed configuration to an expanded configuration. The primary implant body defines an internal void. The auxiliary implant is configured to be disposed in the internal void of the primary implant body and expanded from a collapsed configuration to an expanded configuration. The auxiliary implant defines a central body portion and at least a pair of nodes that extend out from the central body portion. The nodes at least partially define at least one pocket when the auxiliary implant is in its expanded configuration while disposed in the primary implant.

DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings:

FIG. 7D is a sectional end elevation view of the implant assembly illustrated in FIG. 7A, taken along line 7D-7D;

FIG. 7E is a sectional end elevation view of an auxiliary implant similar to FIG. 7D, but constructed in accordance with an alternative embodiment;

FIG. 7F is a sectional end elevation view of an auxiliary implant assembly similar to the auxiliary implant assembly illustrated in FIG. 7E, but constructed in accordance with another alternative embodiment.

FIG. 8A is a perspective view of a support sleeve constructed in accordance with an alternative embodiment;

FIG. 8B is a perspective view of a support sleeve constructed in accordance with another alternative embodiment;

FIG. 10A is a perspective view of an opening assembly of an implant insertion assembly, including a cannulated body and an opening device received in the cannulated body;

FIG. 10B is a perspective view of the opening device illustrated in FIG. 10A;

FIG. 10C is a perspective view of the cannulated body illustrated in FIG. 10A;

FIG. 11A is a perspective view of the opening assembly as illustrated in FIG. 10A, but wherein the opening device has a curved distal end;

FIG. 11B is a perspective view of the opening device illustrated in FIG. 11A;

FIG. 11C is a perspective view of the cannulated body illustrated in FIG. 10A;

FIG. 12B is a top plan view similar to FIG. 12A, but showing the expansion body expanded inside the primary implant in the vertebral body; and FIG. 12C is a top plan view similar to FIG. 12B, but showing the expansion body removed from the primary implant, and the auxiliary implant inserted into the primary implant via the insertion assembly.

DETAILED DESCRIPTION

Figure 1B:
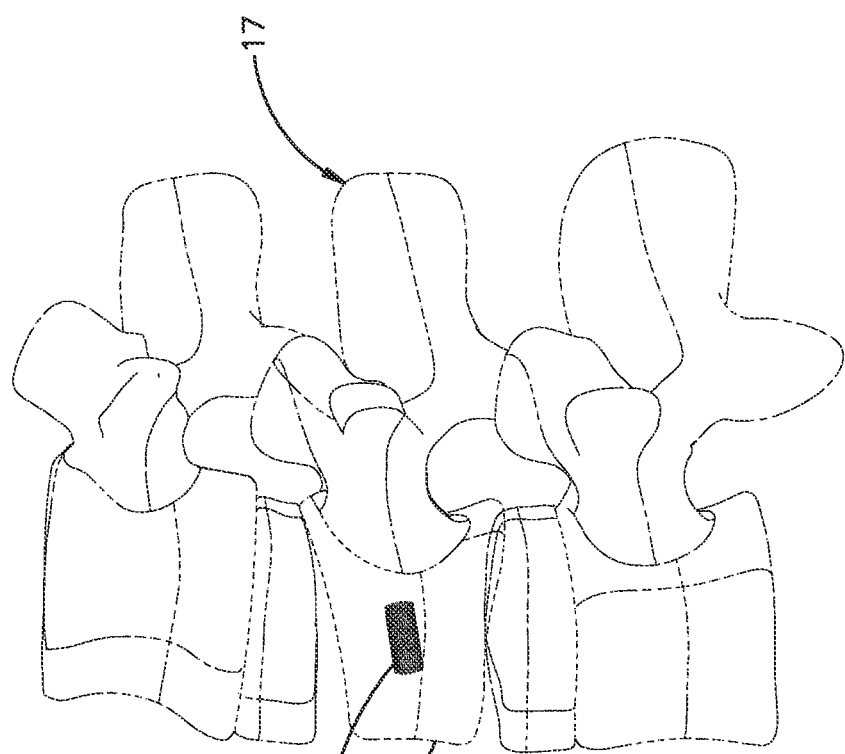
FIG. 1B is a schematic side elevation view of the series of vertebrae illustrated in FIG. 1A, showing a primary expandable implant disposed in the vertebral body of the target vertebra in a compressed insertion configuration.
Figure 1A:
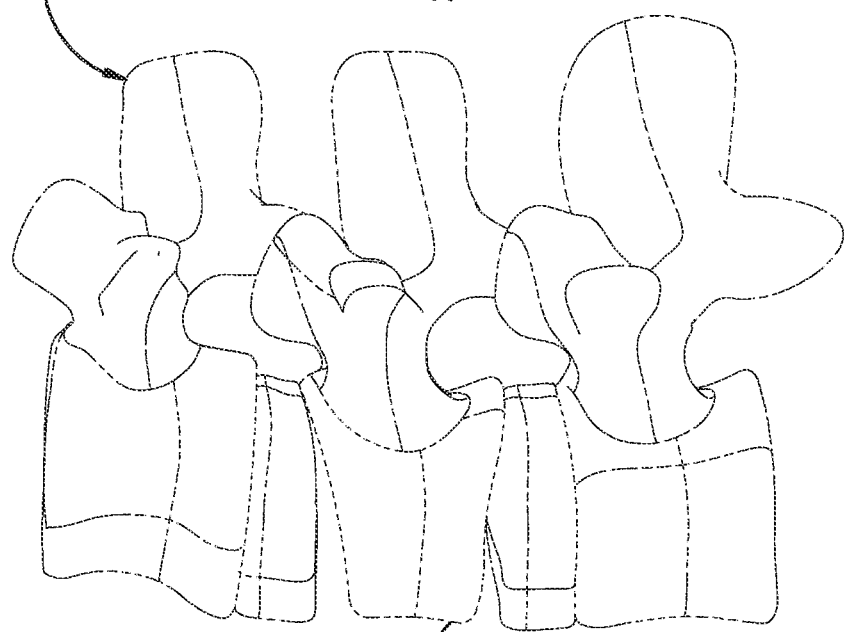
FIG. 1A is a schematic side elevation view of a series of vertebrae including a target vertebra whose vertebral body has been compressed.
Figure 1D:
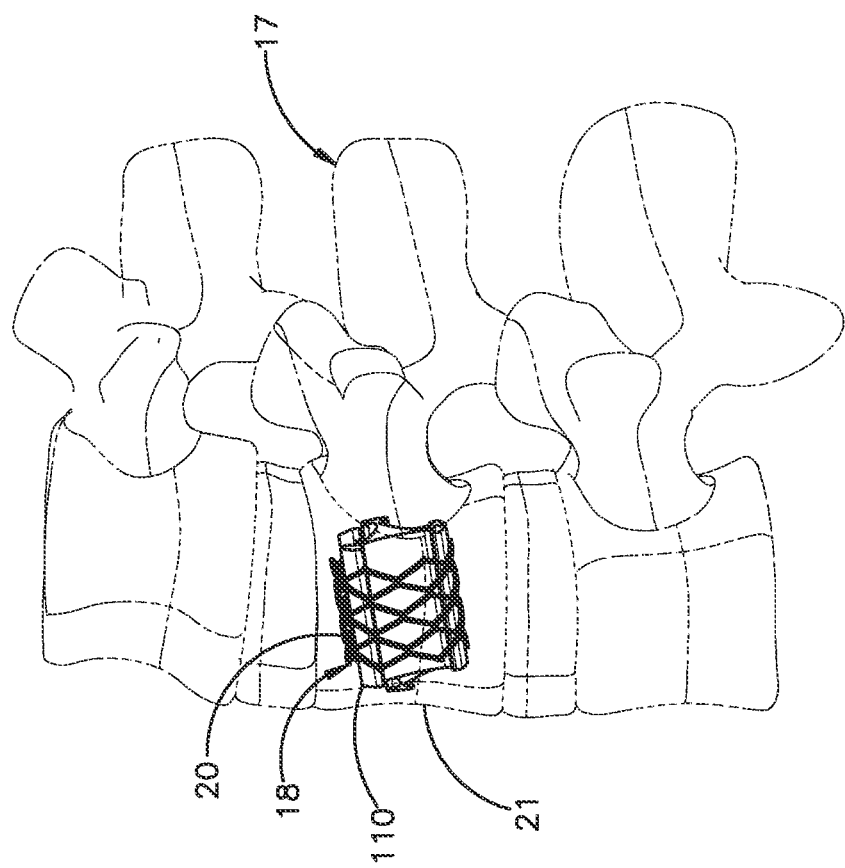
FIG. 1D is a perspective view of an implant system, including a primary implant illustrated in FIG. 1C and an auxiliary implant disposed in the primary implant, showing the primary implant assembly in an expanded configuration.
Figure 1C:
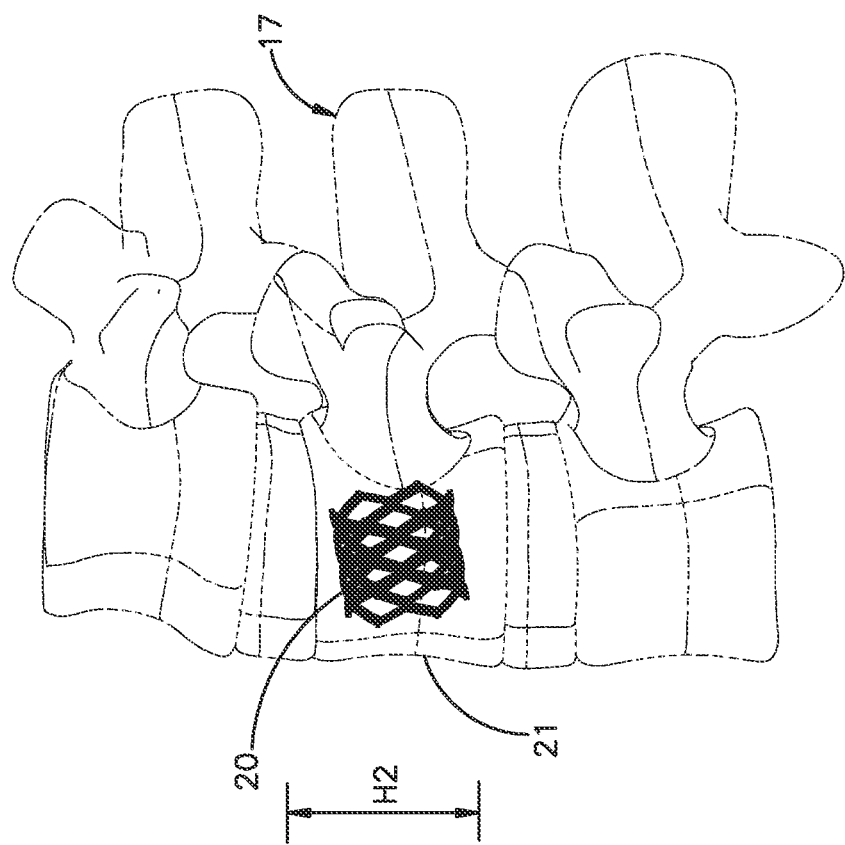
FIG. 1C is a schematic side elevation view of the series of vertebrae illustrated in FIG. 1B, showing the primary implant in an expanded configuration so as to restore height to the vertebral body of the target vertebra.

Referring initially to FIGS. 1A-D, an expandable implant system 18 includes at least one implant assembly 19, such as a pair of implant assemblies 19, that are configured to be inserted into a target bone, which can be a vertebra 17 as illustrated. In particular, each implant assembly 19 can be implanted in the vertebral body portion 21 of the vertebra 17 that has been subjected to trauma, such as a vertebral compression fracture ("VCF"), and has a reduced anterior height H1 and an increased kyphotic angle (FIGS. 1A-B) with respect to an anatomically normal height prior to the trauma. The implant assembly 19 includes a primary expandable implant 20, which can be a stent, that can be implanted into the vertebral body portion 21 via a minimally invasive surgical technique, such as, for example, through one or more cannulas, preformed holes or percutaneously. Once implanted, the expandable implant 20 is configured to reposition and stabilize the target bone to re-establish structural integrity and reduce or eliminate painful micro-movements.

As generally understood by one of ordinary skill in the art, it should be understood that while the expandable implant assembly 19 is illustrated as usable in an interior volume of the targeted vertebral body portion 21 in the spine (for example, in the lumbar, thoracic or cervical regions), it is appreciated that the expandable implant system 18 can be used in other parts of the body such as, for example, in an intervertebral disc space for cage, nucleus replacement, etc., between tissue and bone, in long bones such as proximal humerus and proximal tibia or bones in the hand, face, feet, extremities, cranium, or in nearly any bone in the human body, or as intervertebral spacers to restore intervertebral space height, and thus implanted in a degenerated intervertebral disc, or after removal of the intervertebral disc in an intervertebral space.

Thus, the primary implant 20 has a first insertion configuration having a corresponding first insertion size that is configured to allow the primary implant 20 to be inserted into an interior volume of the target bone. Once inserted into the target bone, the expandable implant can be expanded in situ from the insertion configuration to a second expanded configuration having a corresponding second expanded size that is greater than the insertion size. When in the expanded configuration, the primary implant 20 can generally create a cavity within the interior volume of the vertebral body portion 21, stabilize the vertebral body portion 21, and occupy a portion of, or augment, the interior volume of the vertebral body portion 21. Thus, the primary implant 20 is expandable to an expanded configuration that restores the height of the vertebral body portion to a second anterior height H2 that is greater than the first anterior height H1, and a reduced or eliminated kyphotic angle with respect to that illustrated in FIGS. 1A-B. The second height H2, for instance, can be an anatomically desirable height. The implant assembly 19 further includes an auxiliary implant 110 is configured to be inserted into the primary implant 20, for instance through the cannula, in a retracted configuration, and subsequently expanded inside the primary implant to support the primary implant in its expanded configuration such that the expandable implant system 18 can absorb post-operative anatomical forces subjected to the vertebra 17 during normal anatomical function, and maintain its structural integrity. The implants 20 and 110 can be made from any suitable reinforced biocompatible material, and can include titanium, a titanium alloy, polyetherether ketone (PEEK), polyetherketoneketon (PEKK) or the like.

Referring now to FIGS. 2A-D, the primary implant 20 is illustrated as including a substantially annular implant body 22 disposed about a central axis 24 that extends in an axial direction A. The implant 20 can be made from a polymeric material with directed fibres, and can be coated if desired with one or more antibiotic agents in order to inhibit infections. In accordance with one embodiment, the implant 20 is made from a Phynox (e.g., L605 alloy, or CoCrWNi alloy) material, though the implant 20 can alternatively be made from any suitable alternative material, such as stainless steel, Elgiloy (CoCrMo), Titanium, Ti-6A1-7Nb (TAN), Ti-6A1-4V (TAV), polyetheretherketone (PEEK), or any biocompatible plastic such as PEEK, PET, PUR, PCU, Silicones, or the like. The implant 20 can further be coated with an osteoconductive layer such as sprayed Hydroxyapatite or other Ca and P compositions. The implant 20 can be manufactured by selective laser cutting process in order to change the geometry as desired.

The implant body 22 includes an inner surface 22a that defines an internal void 23, and an opposed outer surface 22b. The implant body 22 includes a plurality of connected linkages 26. Each linkage 26 includes a first and second opposed flexible and plastically deformable side portions 28 and 30, respectively, and first and second opposed flexible end portions 32 and 34, respectively, that provide flexible and plastically deformable hinges connected between the side portions 28 and 30. The end portions 32 and 34 can be curved or otherwise shaped as desired, and define a radius of curvature in accordance with the illustrated embodiment. Likewise, the side portions 28 and 30 are substantially straight and parallel along the axial direction when the implant 20 is in the insertion configuration, though it should be appreciated that the side portions 28 and 30 can define any suitable shape and spatial relationship as desired.

In accordance with the illustrated embodiment, the linkages 26 are arranged in at least one, such as a plurality of, columns 27, and at least one, such as a plurality of, rows 29. The columns 27 extend along a column direction that is coincident with the axial direction A in the illustrated embodiment. The rows 29 extend along a row direction that is circumferential so as to define an annulus in the illustrated embodiment. The ends of the linkages 26 are integrally or directly connected to each other along the column direction as illustrated, though it should be appreciated that the linkages 26 could alternatively be connected to each other indirectly via a connection member. The sides of the linkages 26 are indirectly connected to each other via corresponding circumferential arms 36, though it should be appreciated that the sides of the linkages 26 could alternatively be directly connected to each other. It can thus be said that the linkages 26 are connected to each other, either indirectly or indirectly, along the column and row directions so as to define respective columns 27 and rows 29.

In accordance with one embodiment, the side portions 28 and 30 extend axially, that is they extend along a direction having an axial component. Otherwise stated, the side portions 28 and 30 extend along a direction that is angularly offset with respect to a radial direction R that extends along a direction perpendicular with respect to the central axis 24. Accordingly, as will be appreciated from the description below, the side portions 32 and 34 are configured to expand and plastically deform when a radially outward force is applied to the implant body 22, thereby expanding the size of the internal void 23. The implant 20 can be expanded from its insertion configuration to its expanded configuration by inserting a sufficient volume of thermosetting bone filler material into the internal void 23 of the implant 20, such that the material fills the void 23 and applies a radially outward expansion force F against the linkages 26. For instance, as will be described in more detail below, the implant assembly 19 can include an expansion device 58, such as an expandable bladder 69 (see FIGS. 10E-F), that is temporarily placed inside the implant body 22 and expanded so as to expand the implant body 22, such that the implant body 22 is plastically deformed in an expanded configuration. The bladder can then be deflated and removed from the implant body 22, and the auxiliary implant 110 can be implanted in the primary implant and subsequently expanded so as to augment, support, and stabilize the primary implant 20.

Figure 2A:
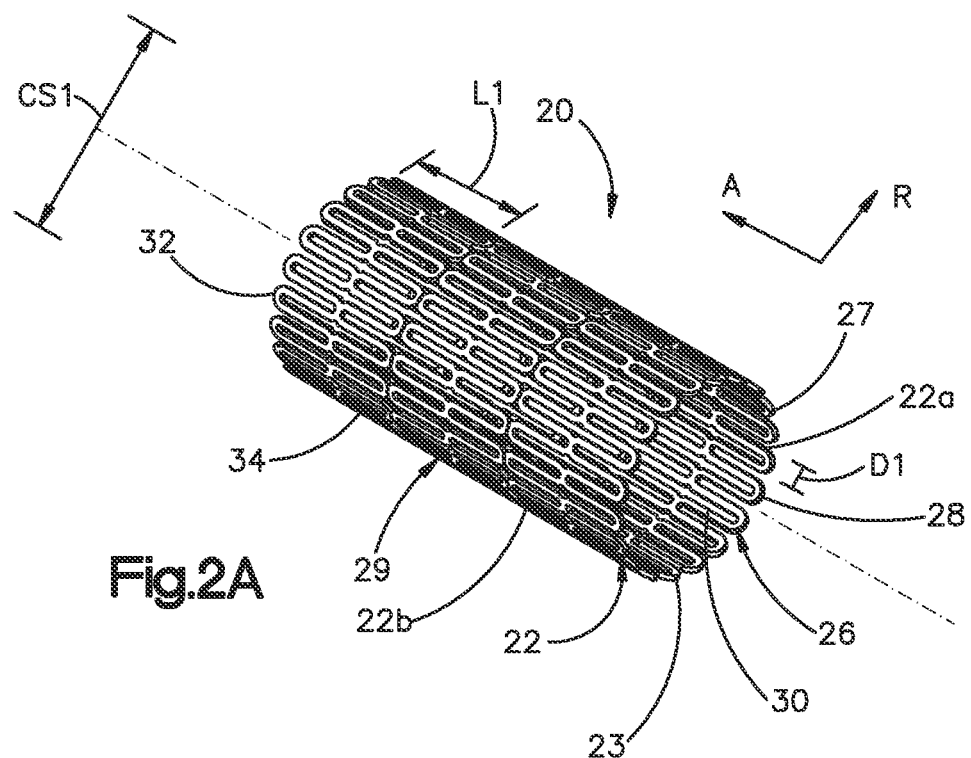
FIG. 2A is a perspective view of the primary implant illustrated in FIG. 1D, shown in a collapsed configuration.

In accordance with the embodiment illustrated in FIG. 2A, when the primary implant 20 is in the compressed or collapsed insertion configuration, each given linkage defines a length L1 that extends between the opposed end portions 32 and 34. Furthermore, when the implant 20 is in the insertion configuration, the side portions 28 and 30 extend substantially parallel to each other and are separated from each other by a first or insertion distance D1, which extends circumferentially in accordance with the illustrated embodiment. Otherwise stated, the side portions 28 and 30 are separated by the first distance D1 at a select location along the length of the side portions 28 and 30. Thus, the circumference of the implant body 22 is at least partially defined by the first distance D1. When the implant 20 is in the insertion configuration, the implant body 22 defines a first cross-sectional distance CS1, which can be a diameter, for instance when the implant defines a cylindrical surface as illustrated. The first cross-sectional distance CS1, and thus the first distance D1, provides the implant 20 with the first insertion size that is configured to allow the implant 20 to be inserted into an interior volume of the target bone.

Figure 2B:
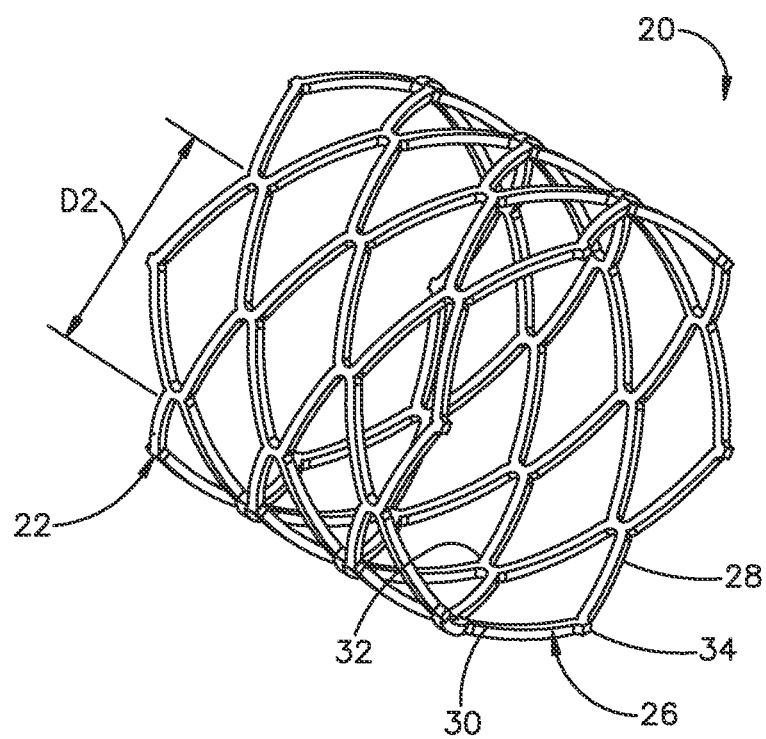
FIG. 2B is a perspective view of the primary implant illustrated in FIG. 2A, shown in an expanded configuration.
Figure 2C:
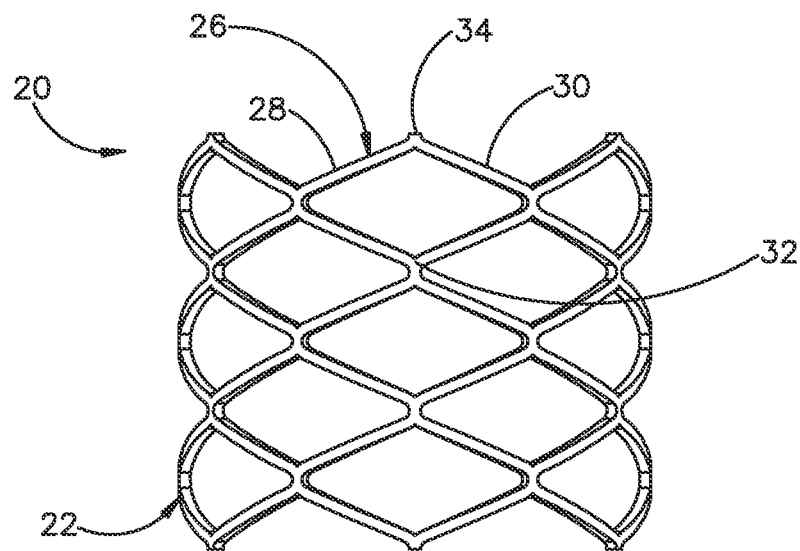
FIG. 2C is a side elevation view of the primary implant illustrated in FIG. 2B.
Figure 2D:
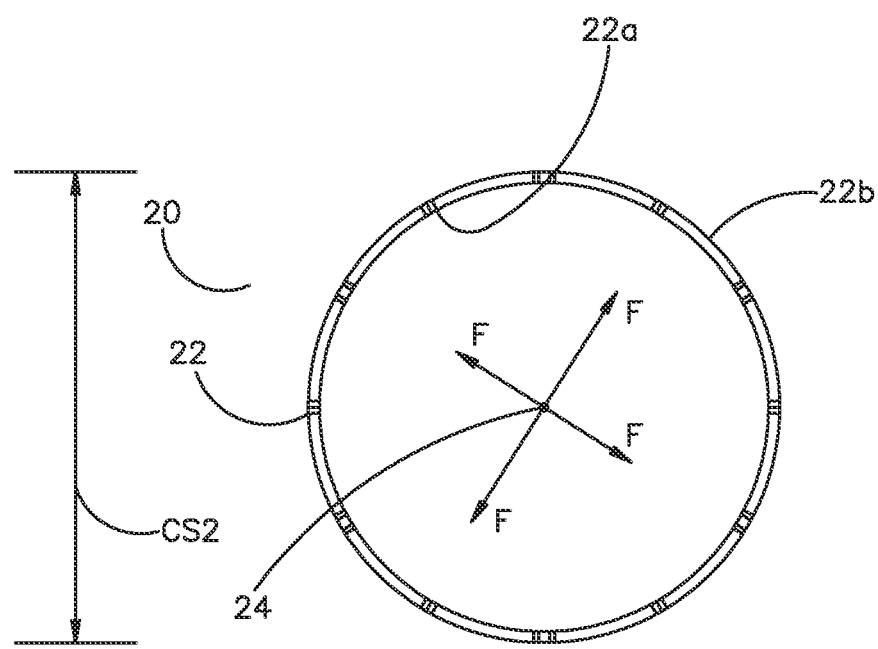
FIG. 2D is an end elevation vie of the primary implant illustrated in FIG. 2B.

The expandable implant 20 is configured to expand from the insertion configuration illustrated in FIG. 2A to the expanded configuration illustrated in FIGS. 2B-D. Each linkage 26 can be substantially identically constructed, and thus defines substantially the same initial length L1 and distance D1 as the other linkages 26. When the radially outward expansion force F is applied to the inner surface of the linkage body 22, and in particular to the linkages 26, the linkages 26 expand circumferentially. For instance, the initial distance extending between the side portion 28 and 30 of at least one up to all of the linkages 26 increases from the first insertion distance D1 to a second expanded distance D2 that is greater than the first insertion distance D1. Simultaneously, the length of at least one up to all of the linkages 26 is reduced from the first length L1 to a second expanded length L2 that is less than the first insertion length L2. Assuming that the expansion force F is distributed uniformly about the implant body 22, the identically constructed linkages 26 will expand substantially uniformly, and the implant body 22 will expand to a second expanded cross-sectional distance or diameter CS2 that is greater than the first insertion cross-sectional distance or diameter CS1.

Figure 3A:
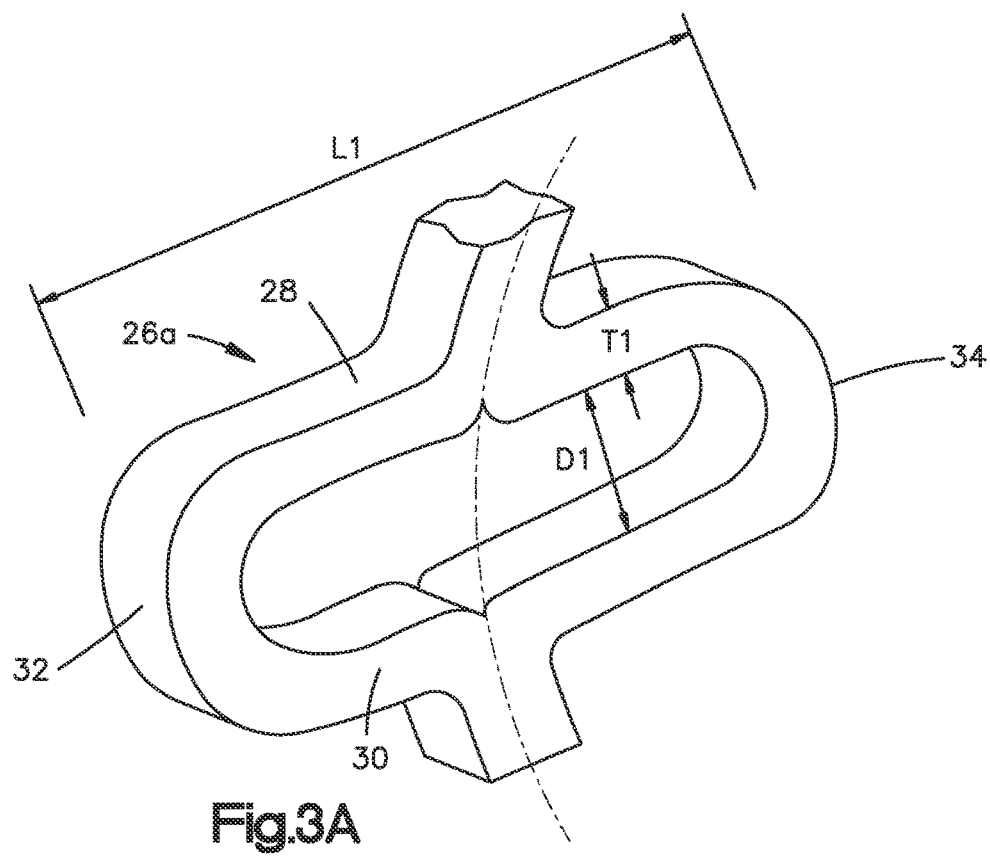
FIG. 3A is a perspective view of a first linkage of the primary implant constructed in accordance with an alternative embodiment.
Figure 3B:
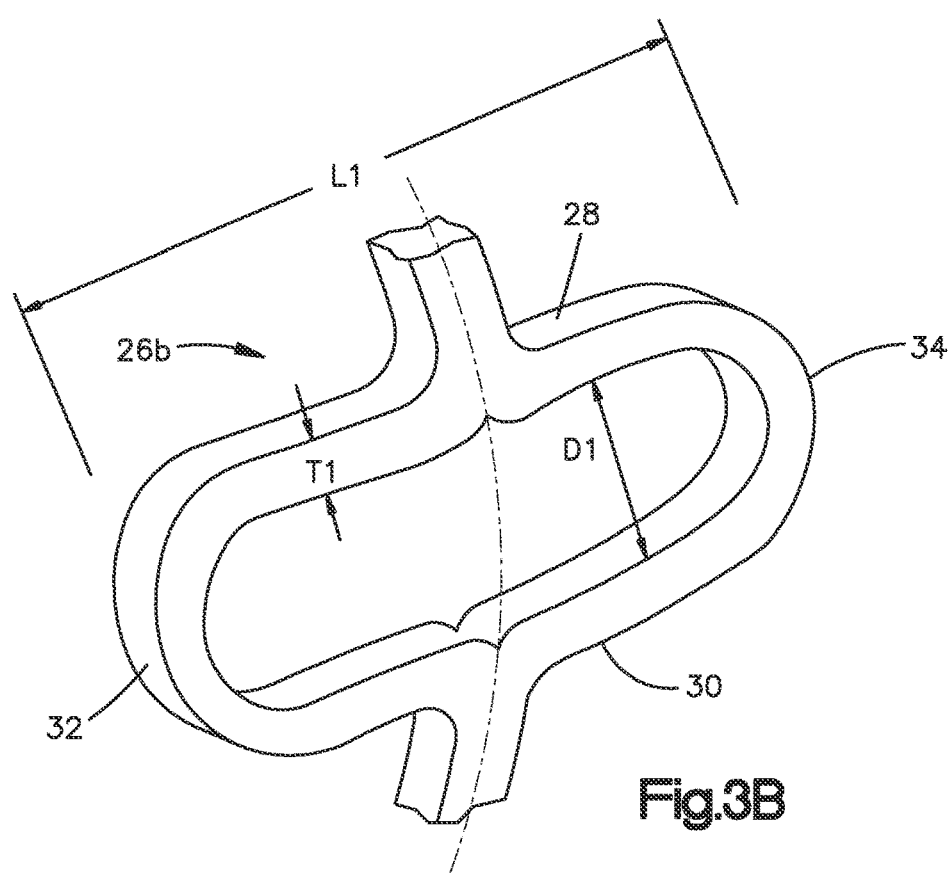
FIG. 3B is a perspective view of a second linkage of the primary implant of FIG. 3A.

While the linkages 26 can all be substantially identically constructed as described above with respect to FIGS. 2A-D, it is appreciated that at least one, such as a first plurality, of the linkages 26 can be constructed differently than at least one, such as a second plurality, of the linkages 26. For instance, referring to FIGS. 3A-B, the implant 20 can include a first plurality of elements or linkages 26a and a second plurality of elements or linkages 26b. The linkages 26a can be circumferentially spaced from the linkages 26b, such that they are on circumferentially opposed sides of the implant body 22 relative to each other. Otherwise stated, a first select number of columns 27, and in particular adjacent columns 27 can include linkages 26a, while a second select number of columns 27, and in particular adjacent columns 27, can include linkages 26b. Alternatively or additionally, the linkages 26a can be axially spaced from the linkages 26b, such that a first select number of rows 29, and in particular adjacent rows 29, can include linkages 26a, while a second select number of rows 29, and in particular adjacent rows 29, can include linkages 26b.

In accordance with the illustrated embodiment, the axial insertion length L1 of the first plurality of linkages 26a is greater than the axial insertion length L1 of the second plurality of linkages 26b when the implant 20 is in the insertion configuration, such that the circumferential distance of the first plurality of linkages 26a is substantially equal to the circumferential distance of the second plurality of linkages 26b (though the circumferential distances could be different between the linkages 26a and the linkages 26b as desired). Furthermore, the linkages 26a can have a wall thickness T1 that is greater than the wall thickness Ti of the linkages 26b. It should thus be appreciated that the circumferential distance of the first plurality of linkages 26a is configured to expand greater than the circumferential distance of the second plurality of linkages 26b. In accordance with one embodiment, the first plurality of linkages 26a expands at a greater rate than the second plurality of linkages 26b when subjected to substantially the same expansion force as the second plurality of linkages 26b.

Each implant assembly 19 can thus include the primary implant 20 and the auxiliary expandable implant 110 that are configured to be inserted into a target bone, such as a vertebral body portion 21 of a vertebra 17. While the expandable implant system 18 can include a pair of implant assemblies 19 implanted into the vertebral body portion 21 as illustrated, it should be appreciated that includes at least one implant assembly 19. For instance, in embodiments where one implant assembly 19 is implanted into the vertebral body portion 21, the implant assembly can be centrally disposed in the vertebral body portion 21 so as to prevent the intrusion of disc material from the pressurized adjacent intervertebral disc into or through the broken endplates into the vertebral body portion 21.

Figure 3C:
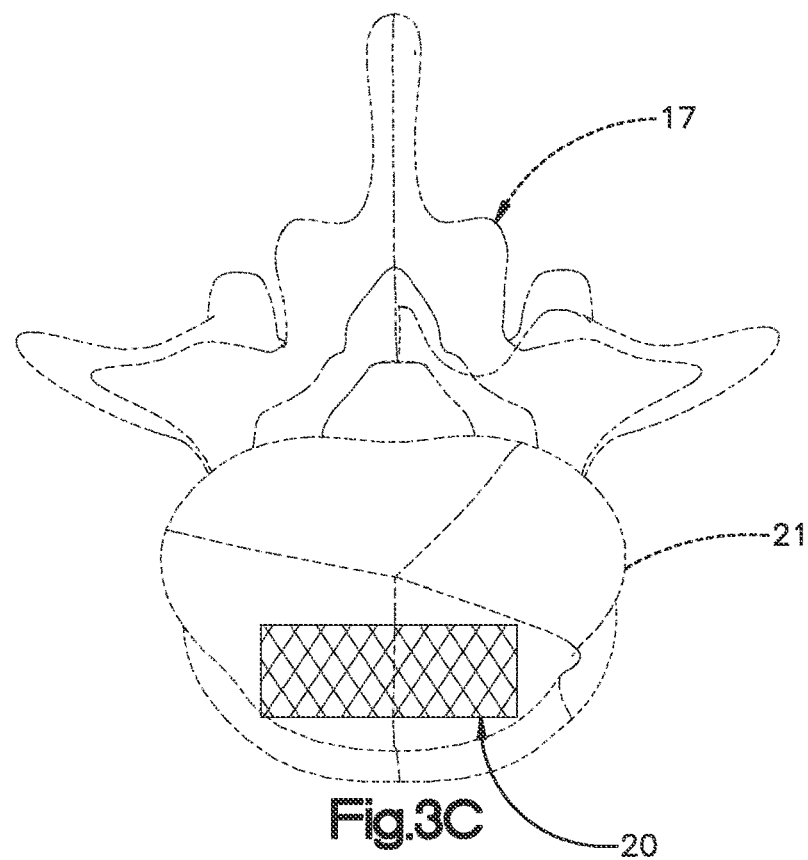
FIG. 3C is a top plan view of the primary implant inserted into a target bone in accordance with one embodiment.
Figure 3D:
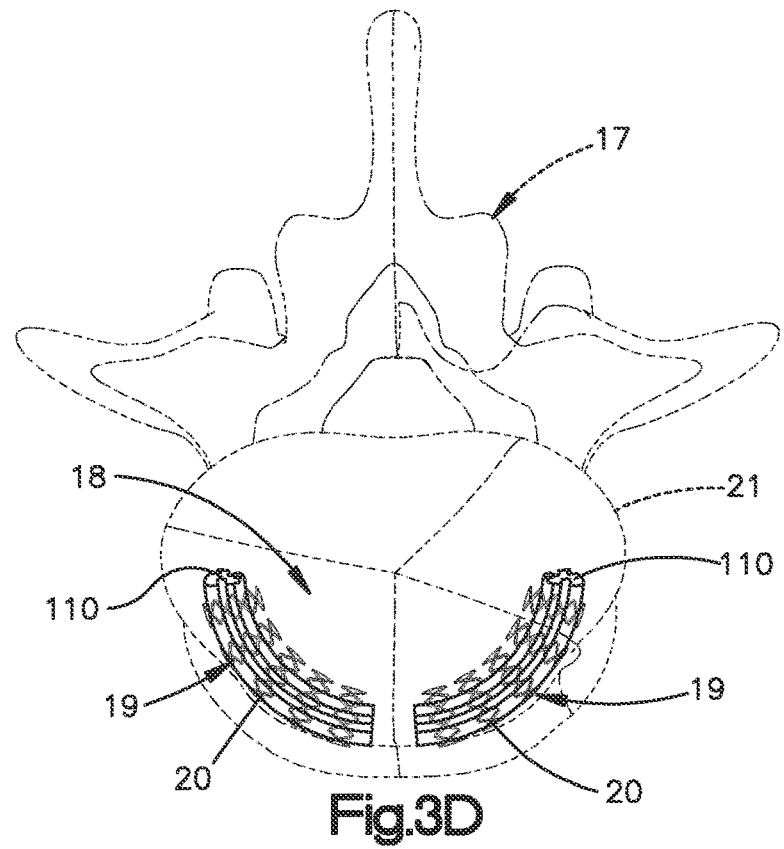
FIG. 3D is a top plan view of an implant system inserted into a target bone in accordance with an alternative embodiment.
Figure 3E:
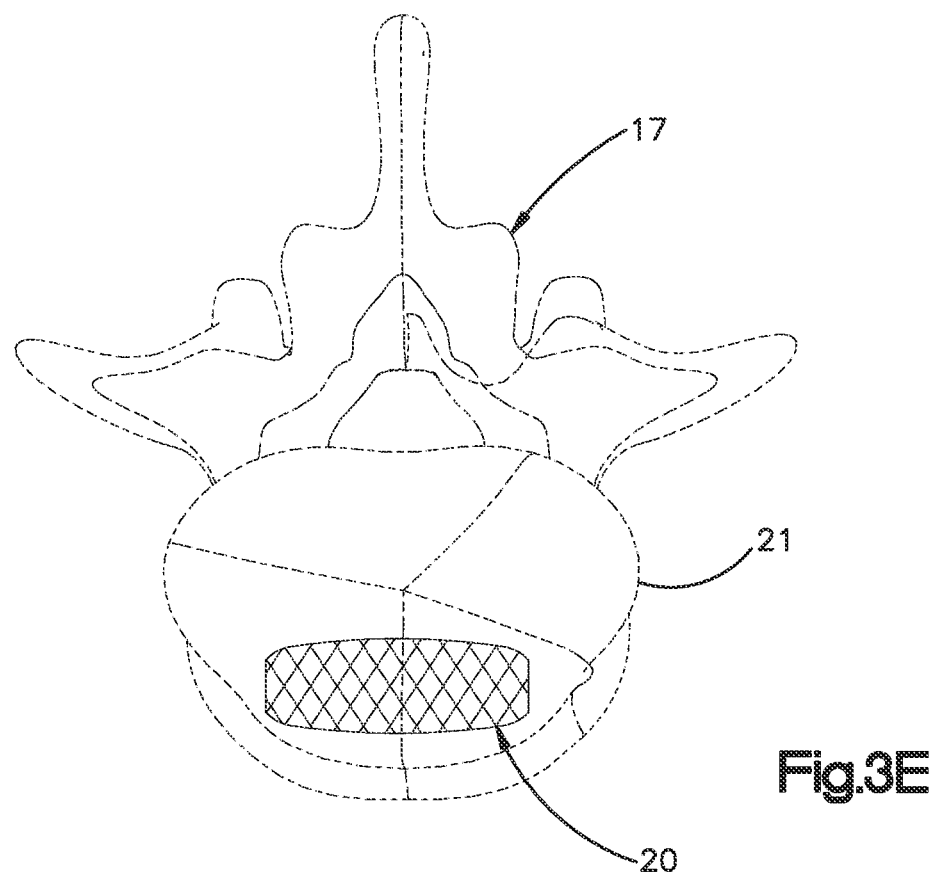
FIG. 3E is a top plan view of an implant system inserted into a target bone in accordance with an alternative embodiment.

When implanted into the target bone, the implant 20 can be configured to produce a symmetric cylindrical shape under a uniform expansion force as illustrated in FIG. 3C, or the implant 20 can be configured to produce an asymmetrically curved shape that resembles the shape of a banana under a uniform expansion force, as illustrated in FIG. 3D. Alternatively still, the implant 20 can assume any shape when expanded. For instance, as illustrated in FIG. 3E, the symmetrical shape of the implant 20 can be cigar-shaped, whereby the implant 20 defines opposed outer surfaces 35 that are curved, such as convex, along its axial direction of extension and elongation. It is also appreciated that the expandable implant system 18 can include a pair of implant assemblies 19, or a single implant assembly that is centrally implanted into the vertebral body 21 so as to prevent intrusion of the adjacent intervertebral disc into the fractured vertebral body 21 as described in more detail below.

In accordance with one embodiment, the implant 20 is inserted into the target bone in its insertion configuration, whereby the linkages 26 can be referred to as in a compressed or collapsed configuration, which can be folded as illustrated, such that the implant 20 can be passed through a cannula, through the openings formed in the pedicles or in lateral openings extending into the vertebral body portion 21, and into an interior cavity of the vertebral body portion 21, as described in more detail below. The implant 20 can follow a guide path of a guide wire in accordance with one embodiment. The guide path can be straight or curved, and thus the implant 20 can be flexible so as to follow the curved guide path. When the target bone is the vertebral body portion 21, the plastic deformation of the primary implant 20 allows the implant 20 to provide augmentation in the anterior aspect of the vertebral body portion 21.

When the primary implant 20 includes the first plurality of linkages 26a and the second plurality of linkages 26b, Hooke's Law demonstrates that the implant body 22 can assume an asymmetrical or bent shape when the implant body 22 is expanded elastically. It should be appreciated, however, that expansion of the linkages 26a and 26b occurs beyond the elastic deformation limit, such that the implant body 22 undergoes plastic deformation. Due to the inflation and expansion of the auxiliary implant 110, the primary implant 20 can be substantially in its expanded configuration.

Example Embodiment—Application of the Hooke's Law

Definitions:
 $\varepsilon$ Strain
 $\sigma$ Tensile Strength
 A Cross-sectional area of bar
 $A_i$ 0.4 mm2;
 $A_o$ 0.2 mm2
 l Length of bar
 $l_i$ 8 mm
 $l_o$ 10 mm
 E Modulus of Elasticity Phynox: 203-400 Mpa
 Elongation: $\Delta l = \varepsilon \cdot l$
 Whereas strain is: $\varepsilon = \sigma / E$
 And: $\Delta l = \sigma \cdot l / E$ Assumption, where "i" indicates the region of the implant body 22 having the second plurality of linkages 26b (which can be located at a circumferentially inner end of the implant body 22), while "o" indicates the region of the implant body 22 having the first plurality of linkages 26a (which can be located at a circumferentially outer end of the implant body 22), and the expansion is under a substantially uniform expansion force (or tensile force). The resulting tensile strength of the second plurality of linkages 26b and the first plurality of linkages 26a, respectively, is as follows:

$$\sigma_i = F/A_i = 120N/0.2 \text{ mm2} = 600[N/\text{mm2}]$$

$$\sigma_o = F/A_o = 120N/0.4 \text{ mm2} = 300[N/\text{mm2}]$$

The resulting elongation of the second plurality of linkages 26b and the first plurality of linkages 26a, respectively, is as follows:

$$\Delta l_i = \sigma_i \cdot l_i / E = 300 \text{ MPa} \cdot 8 \text{ mm} / 203'400 \text{ MPa} = 0.011 \text{ mm}$$

$$\Delta l_o = \sigma_o \cdot l_o / E = 600 \text{ MPa} \cdot 10 \text{ mm} / 203'400 \text{ MPa} = 0.030 \text{ mm}$$

Based on this analysis, the implant 20 expands at the region of linkages 26a significantly more than at the region of linkages 26b (approximately 3 fold in above-identified example). Consequently, the implant 20 becomes bent during expansion since the second plurality of linkages 26b has a smaller elongation compared to the first plurality of linkages 26a. It should be appreciated that the numbers of the above example are merely assumptions used to demonstrate the bending effect based on different linkage sizes of the expansion implant 20, and do not represent actual test data.

Figure 4A:
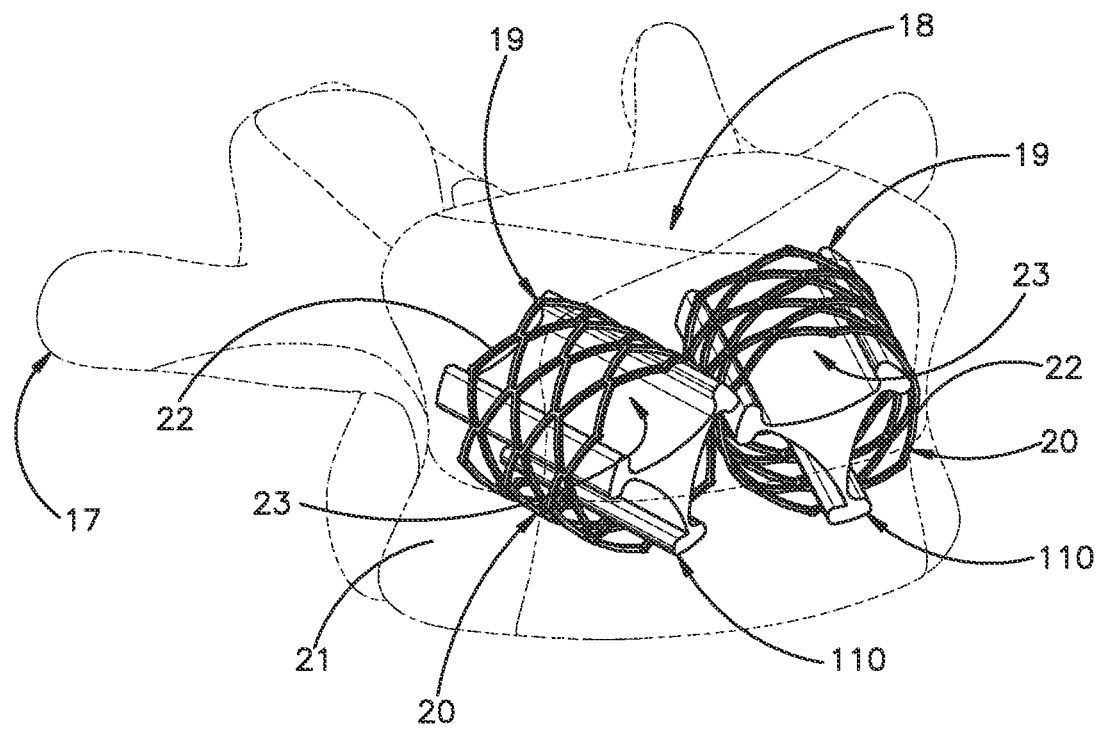
FIG. 4A is a perspective view of an implant system inserted in a target bone, the implant system including a pair of implant assemblies, each including a primary implant an auxiliary implant disposed in the primary implant, wherein the implant system is shown in an expanded configuration.
Figure 4B:
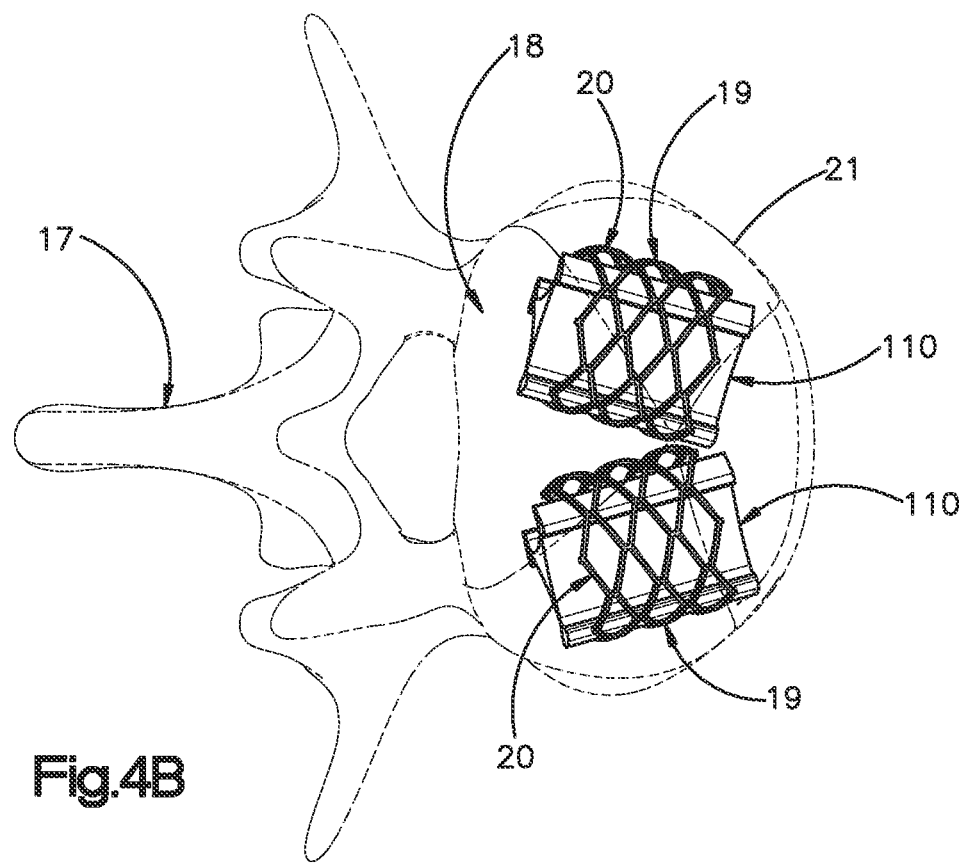
FIG. 4B is a top plan view of the implant system illustrated in FIG. 4A.
Figure 4C:
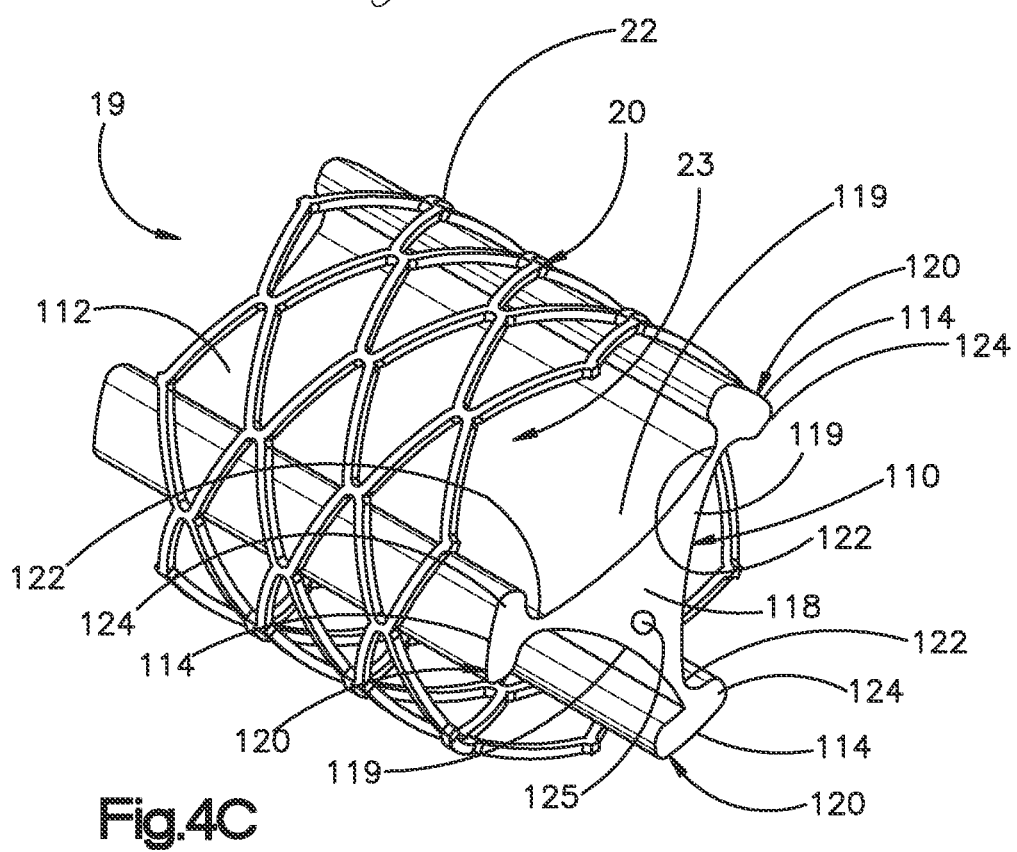
FIG. 4C is a perspective view of one of the implant assemblies illustrated in FIG. 4A.
Figure 4D:
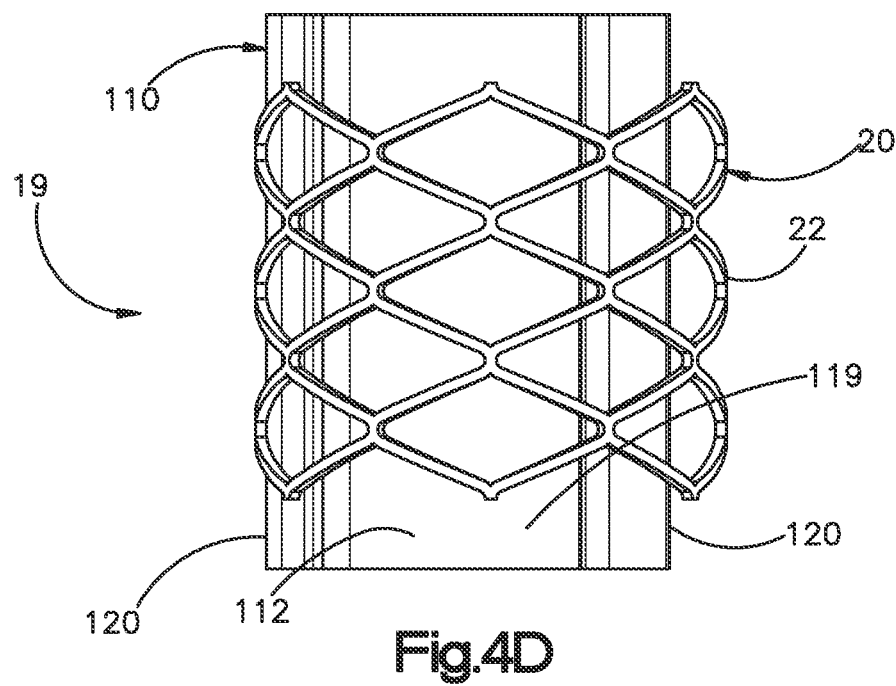
FIG. 4D is a top plan view of the implant assembly illustrated in FIG. 4C.
Figure 4E:
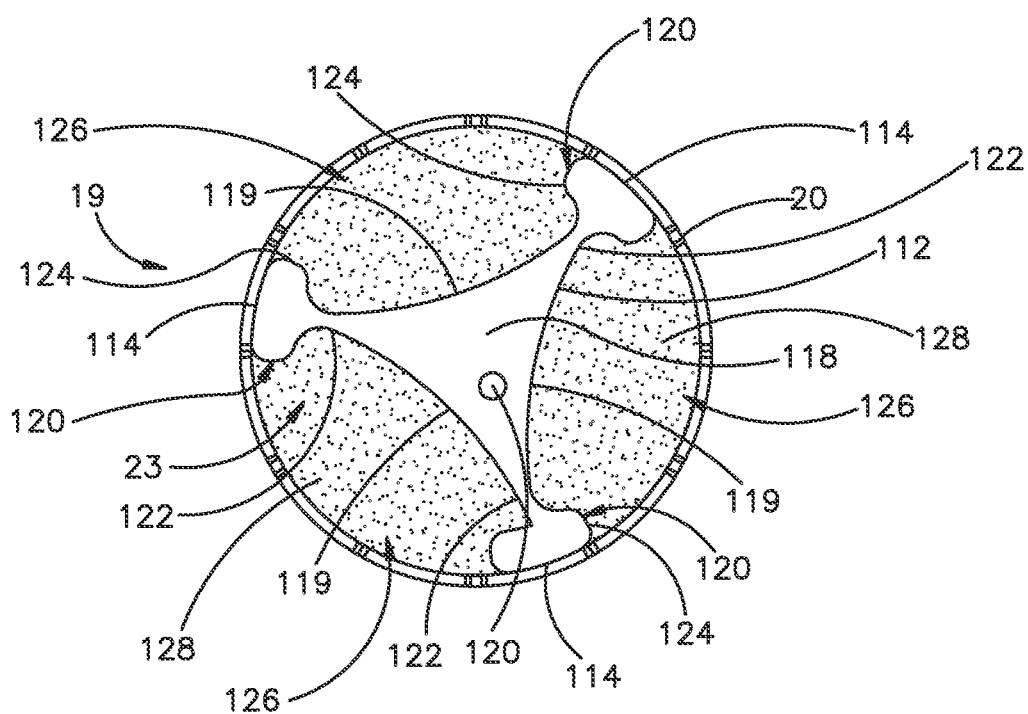
FIG. 4E is an end elevation view of the implant assembly illustrated in FIG. 4D, showing bone stimulating material injected into pockets disposed between the primary and auxiliary implants.
Figure 4F:
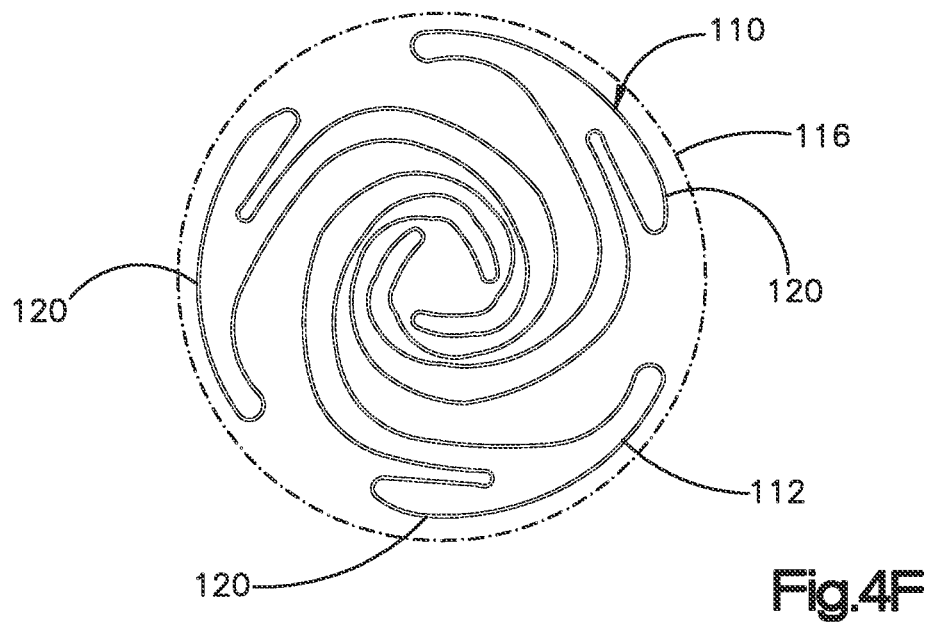
FIG. 4F is an end elevation view of the auxiliary implant illustrated in FIG. 4A, shown in a folded or collapsed insertion configuration.

Referring now to FIGS. 1D and 4A-F, the auxiliary expandable implant 110 is configured to be inserted into the internal void 23 of the primary implant 30 when the primary implant 30 is in the expanded configuration. In particular, the auxiliary implant 110 is insertable into the internal void 23 in a compressed or collapsed insertion configuration (see FIG. 4F), and subsequently expanded in situ inside the internal void 23 to an expanded configuration. The auxiliary implant 110 defines an implant body 112 that includes at least one contact surface 114, such as a plurality of contact surfaces 114 that contact and support the inner surface of the implant body 22, so as to support the primary implant 20 in its expanded configuration. When the auxiliary implant 110 is in the insertion configuration, the contact surfaces 114 are recessed and spaced from the primary implant body 22. When the auxiliary implant body 112 is expanded to the expanded configuration, the contact surfaces 114 contact the inner surface of the primary implant body 22. The contact surfaces 114 can provide a radially outward directed support force onto the implant body 22. As illustrated in FIG. 4F, the auxiliary implant 110 can be inserted into the internal void 23 of the primary implant 20 in its compressed or collapsed insertion configuration inside a sleeve 116, the sleeve 116 can be subsequently removed, and the auxiliary implant 110 can be subsequently expanded.

The auxiliary implant 110 can be expanded from the insertion configuration to the expanded configuration via in-situ injection of a hardening, bone filler material 123, such as for example a biocompatible bone cement, into the interior 115 of the implant body 112 (see, e.g., FIG. 4H) via a port 125 that extends through the implant body 112. In accordance with one embodiment, the bone cement is load-bearing polymethylmethacrylate (PMMA), which is self hardening (e.g., self-curing), though it should be appreciated that the bone filler material can be selected from any suitable bone filling material as desired. The bone cement can also contain radiopacifiers, such as barium sulfate and/or zirconium oxide (ZrO2) to visualize the cement build-up and manage any potential cement leakage in case of leakage in the auxiliary implant 110. However, the bone cement can be devoid of biological constituents since it's shielded from the vertebra 21 under normal operating conditions.

When in the expanded configuration, the auxiliary implant 110 can define any suitable shape as desired. For instance the implant body 112 be substantially equilaterally triangular, so as to define the shape of the Greek letter "delta." It should be appreciated that the triangular shape of the implant body 112 can assume any geometric configuration as desired. In accordance with the illustrated embodiment, the implant body 112 defines a substantially triangular central body portion 118 having side surfaces 119 that can be shaped as desired, such as curved (e.g., concave) or substantially straight, and a plurality of nodes 120 that extend radially out from the vertices of the implant body 112. In accordance with the illustrated embodiment, three nodes 120 are spaced circumferentially equidistantly, though they can be spaced at consistent or variable spacing about the implant body 112. Furthermore, the auxiliary implant 110 can include any number of nodes 120 as desired. Each node 120 can include a neck 122 and a stabilizing support foot 124 that defines a greater circumferential dimension than the neck 122. The support feet 124 define respective radially outer contact surfaces 114 configured to contact the primary implant body 22 in the manner described above. The contact surfaces 114 can be shaped as desired. For instance, the contact surfaces 114 can be curved (e.g., convex) or substantially straight.

It should be appreciated that the expanded configuration can include unfolding the auxiliary implant body 112, and that the auxiliary implant body 112 can be non-compliant when injected with the bone filler material 123, such that the bone filler material 123 unfolds the implant body 112 from the folded insertion configuration illustrated in FIG. 4F, but does not substantially stretch the implant body 112 from the unfolded configuration. Accordingly, the implant body 112 maintains a substantially constant surface are in both the folded or collapsed, and unfolded or expanded, configurations. Alternatively, the implant body 112 can be compliant and semi-stretchable or stretchable in situ after the implant body 112 has been unfolded with respect to the insertion configuration, thereby increasing the outer surface area of the auxiliary implant 110 in the expanded configuration with respect to the collapsed or folded configuration. Accordingly, a sufficient quantity of bone filler material 123 can be injected into the implant body 112 that causes the implant body to unfold from the insertion configuration and subsequently stretch, either elastically or plastically, with respect to the unfolded configuration. Thus, the expanded configuration of the auxiliary implant 110 can include both an unfolded configuration and a stretched configuration.

Referring now to FIG. 4E, the implant assembly 19 can define a plurality of pockets 126 disposed in the internal void 23 between the implant body 112 and the primary implant 20. In particular, each pocket 126 is disposed circumferentially between adjacent nodes 120, and radially between the central body portion 118 and the primary implant 20. Thus, the implant assembly 19 can define three pockets 126 as illustrated, or can define any alternative number of pockets 126 as desired, such as at least one pocket 126. Accordingly, a bone stimulating material or bone-growth material 128 can be inserted into the pockets 126 so as to facilitate bone growth into the implant assembly 19. The bone stimulating material 128 can be, for example, calcium phosphate, bone chips harvested from the patient, allograft (harvested from a cadaver), ceramic granules such as hydroxyapatite (HA) based granules, calcium phosphate (CaP) based cements, and the like. In use, the bone stimulating material 128 can promote biological activity, such as bone in-growth and exchange of nutrients between cranial and caudal vertebral endplates.

Figure 4G:
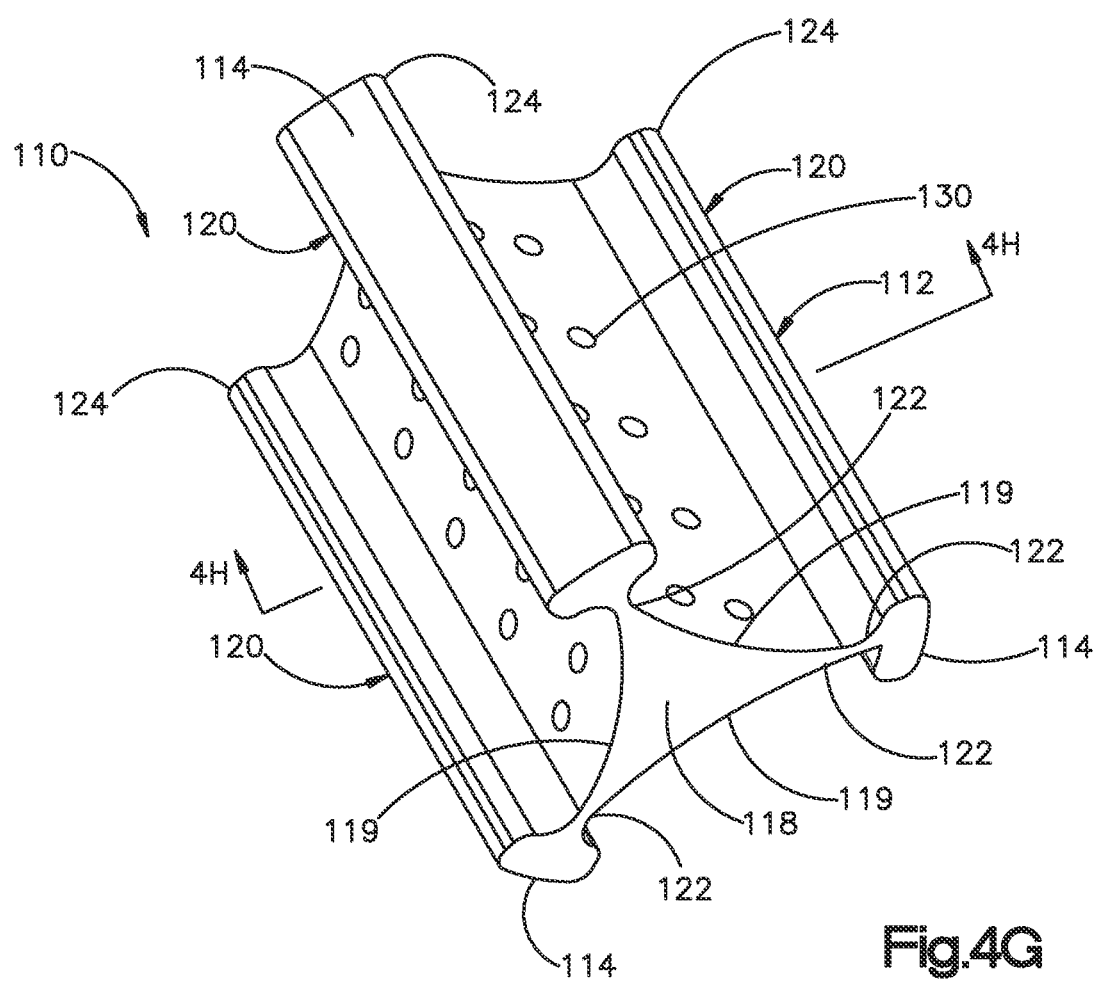
FIG. 4G is a perspective view of the auxiliary implant illustrated in FIG. 4A, including channels in accordance with an alternative embodiment.

While the pockets 126 described above can be discrete and separate from each other with respect to fluid communication, it should be appreciated that the implant assembly 19 can be constructed such that the pockets 126 are in fluid communication with each other. For instance, referring also to FIGS. 4G-H, the auxiliary expandable implant body 112 can further define at least one channel 130, such as a plurality of channels 130 that extend between and through the side walls 119, so as to place two or more of the pockets 126 in fluid communication. Furthermore, the channels 130 can be in fluid communication with each other such that the associated pockets 126 are in fluid communication. The channels 130 can be isolated from the interior 115 of the implant body 112 such that the bone filler material 123 is isolated with respect to the pockets 126. The channels 130 facilitate the transfer of bone stimulating material 128 between the pockets 126. For instance, bone stimulating material can be inserted into one pocket 126, and can travel under pressure through the channels 130 into the other pockets 126. Furthermore, the channels 130 facilitate biological activity such as, for example, bone in-growth through the channels 130 to provide for better rotational stability. The channels 130 can be elongate in the horizontal direction, the vertical direction, and at oblique angles relative to the horizontal and vertical directions. It should be further appreciated that the channels 130 can be in fluid communication with the interior 115 of the implant body 112 such that bone stimulating material injected into the interior 115 both expands the implant 110 and further introduces the bone stimulating material into the pockets 126. Alternatively, the contact surfaces 114 can define an uneven contact with the primary implant 20 so as to define channels that place the pockets 126 in fluid communication with each other.

Figure 5A:
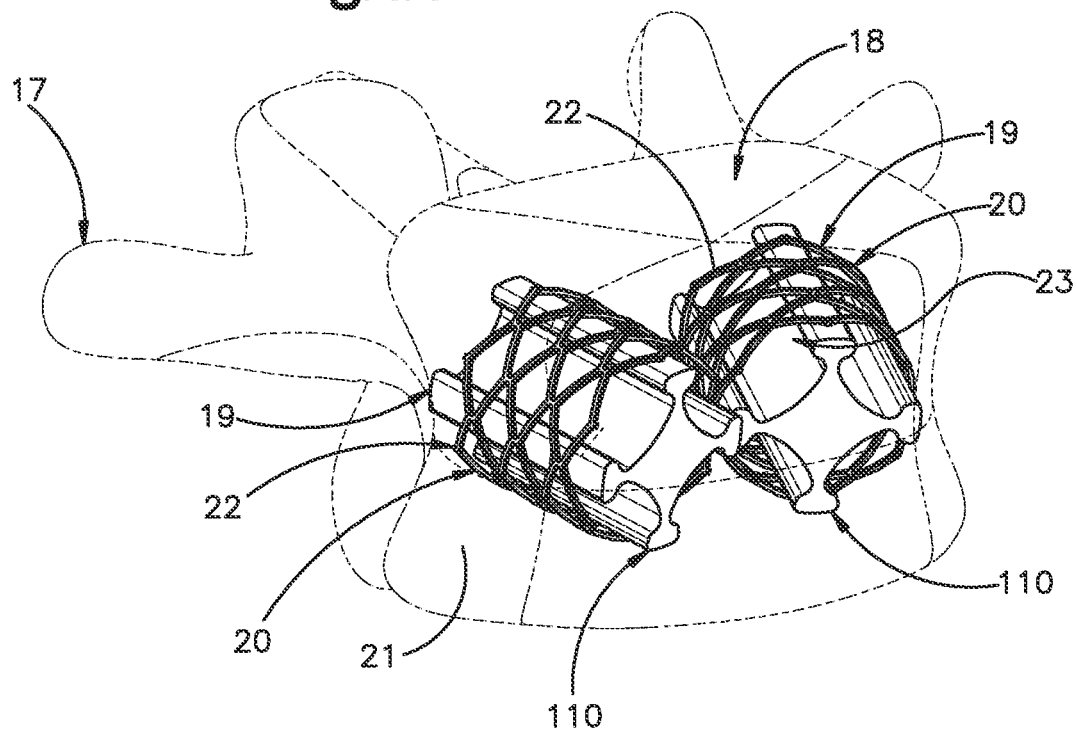
FIG. 5A is a perspective view of an implant system constructed in accordance with an alternative embodiment inserted in a target bone, the implant system including a pair of implant assemblies, each including a primary implant an auxiliary implant disposed in the primary implant, wherein the implant system is shown in an expanded configuration.
Figure 5B:
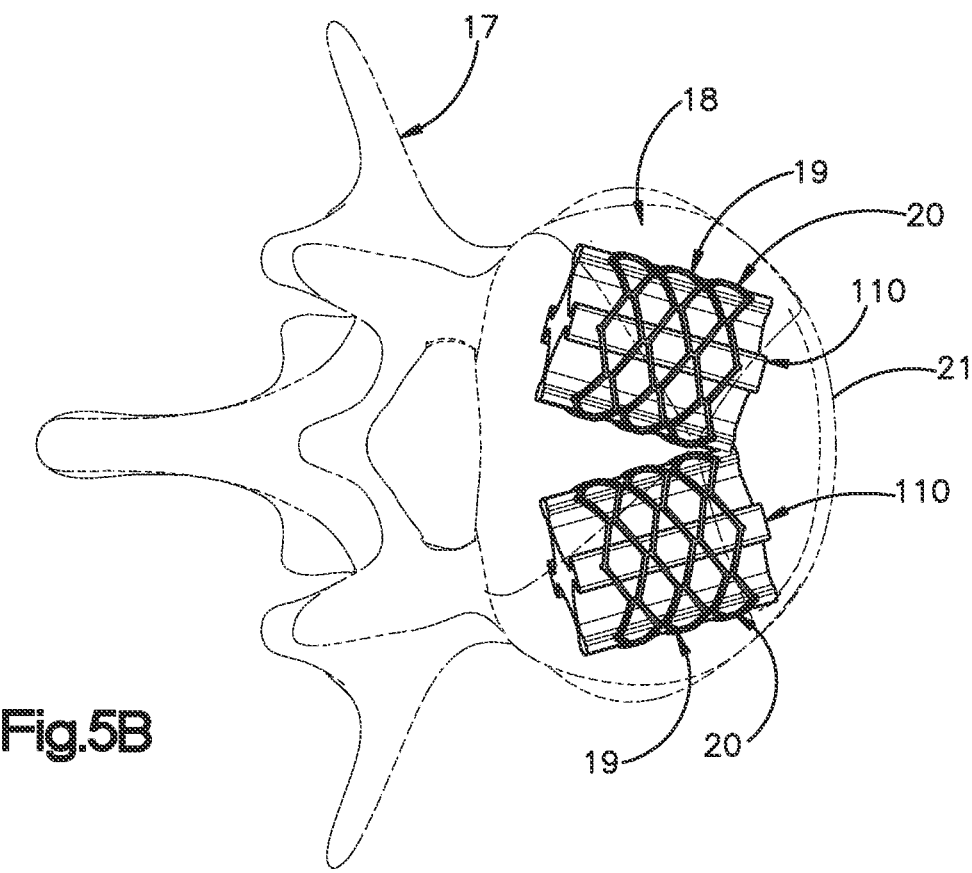
FIG. 5B is a top plan view of the implant system illustrated in FIG. 5A.
Figure 5C:
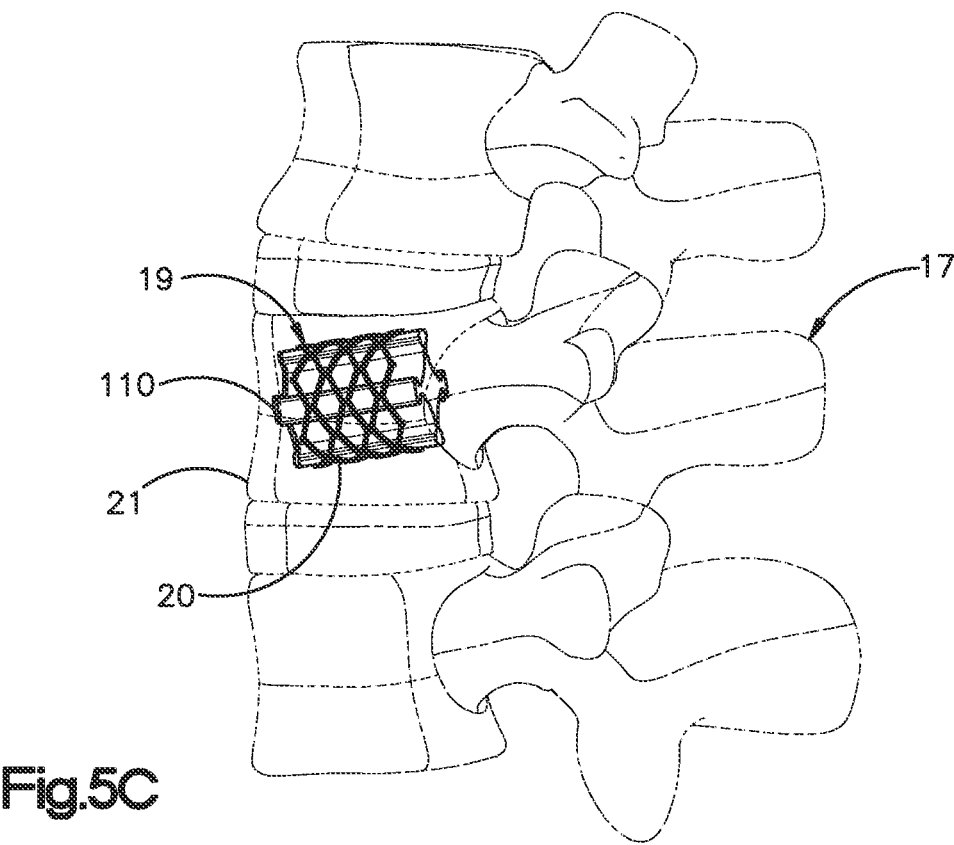
FIG. 5C is a side elevation view of one of the implant assemblies of the implant system illustrated in FIG. 5A.
Figure 5D:
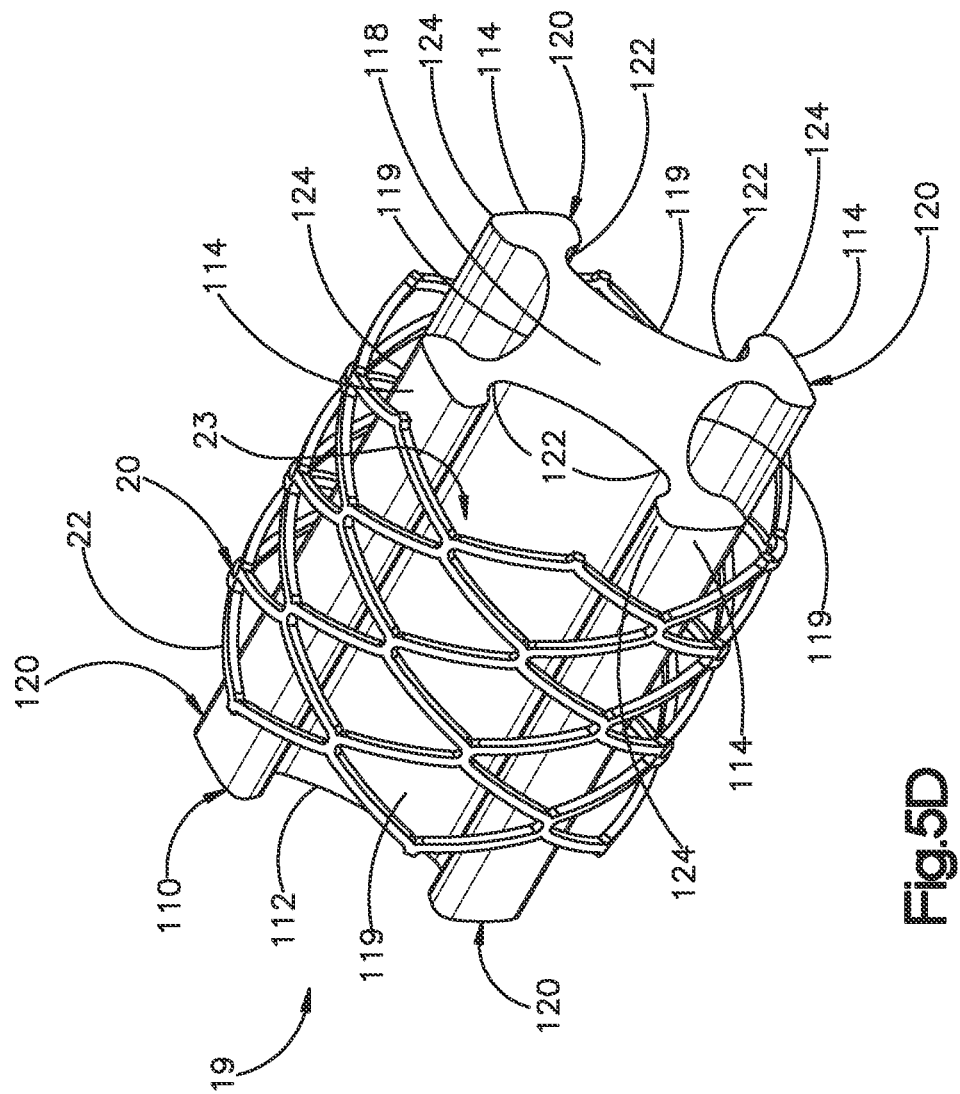
FIG. 5D is a perspective view of one of the implant assembly illustrated in FIG. 5C.
Figure 5E:
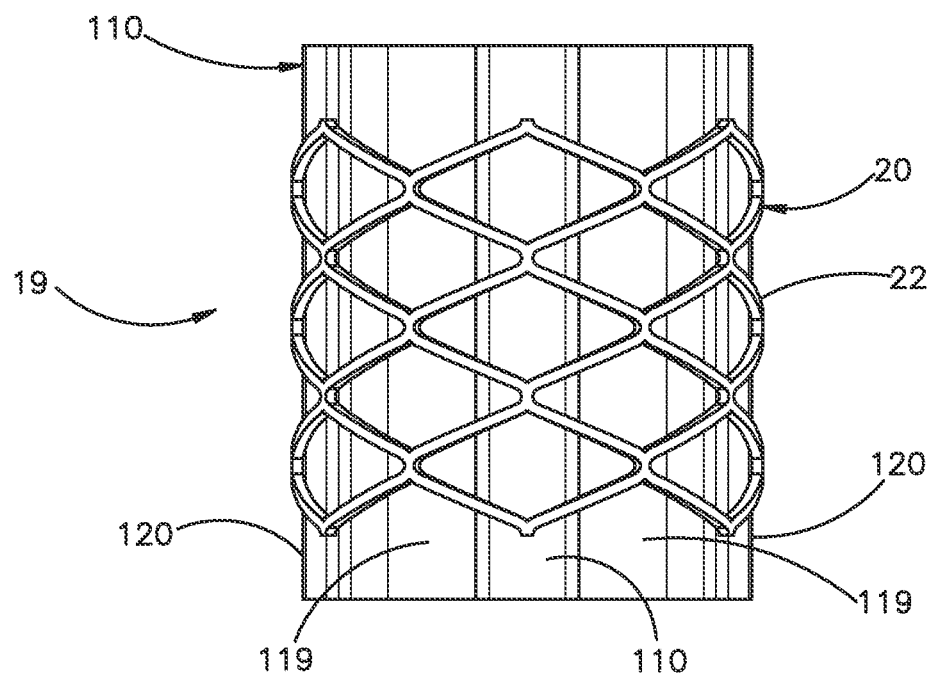
FIG. 5E is a top plan view of the implant assembly illustrated in FIG. 5C.

While the auxiliary implant 110 has been described as having a triangular shape, it should be appreciated that the implant 110 can define any alternative shape as desired that is suitable to support the primary implant 20 during a patient's normal anatomical function. For instance, referring now to FIGS. 5A-G, the auxiliary expandable implant body 112 can be substantially X-shaped. In accordance with the illustrated embodiment, the implant body 112 defines a substantially square or rectangular central body portion 118 having side surfaces 119 that can be shaped as desired, such as curved (e.g., concave) or substantially straight, and a plurality of nodes 120 that extend radially out from the corners of the implant body 112. In accordance with the illustrated embodiment, four nodes 120 are spaced circumferentially equidistantly, though they can be spaced at consistent or variable spacing about the implant body 112. Furthermore, the auxiliary implant 110 can include any number of nodes 120 as desired. The implant 110 is expandable from a compressed or collapsed configuration illustrated in FIG. 5G to the expanded position, for instance as illustrated in FIG. 5A.

Figure 5F:
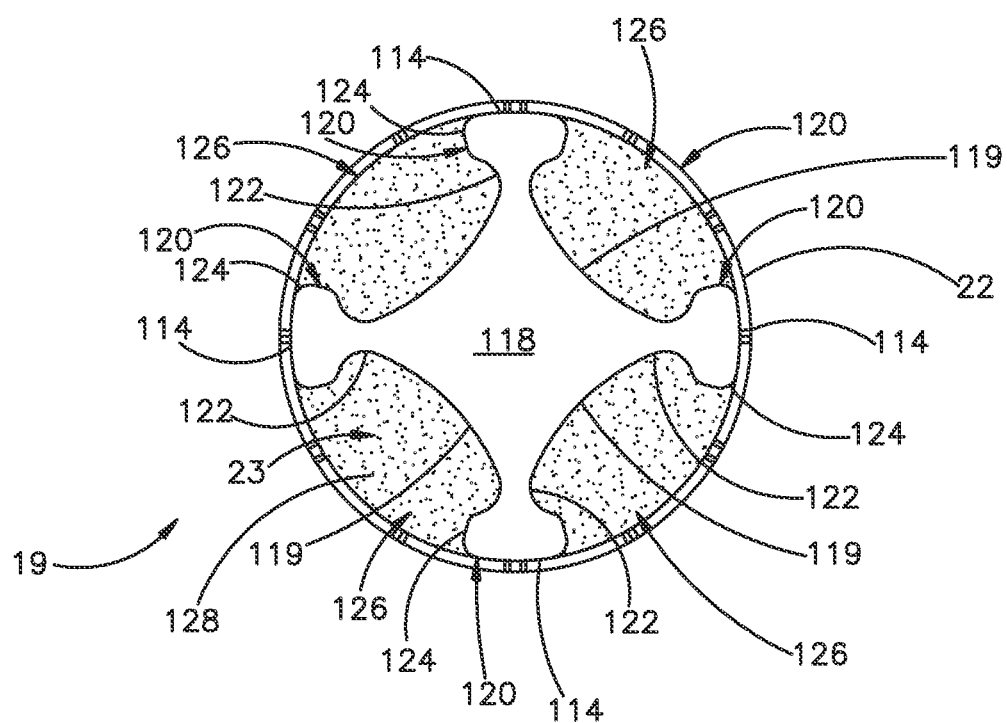
FIG. 5F is an end elevation view of the implant assembly illustrated in FIG. 5E, showing bone stimulating material injected into pockets disposed between the primary and auxiliary implants.
Figure 5G:
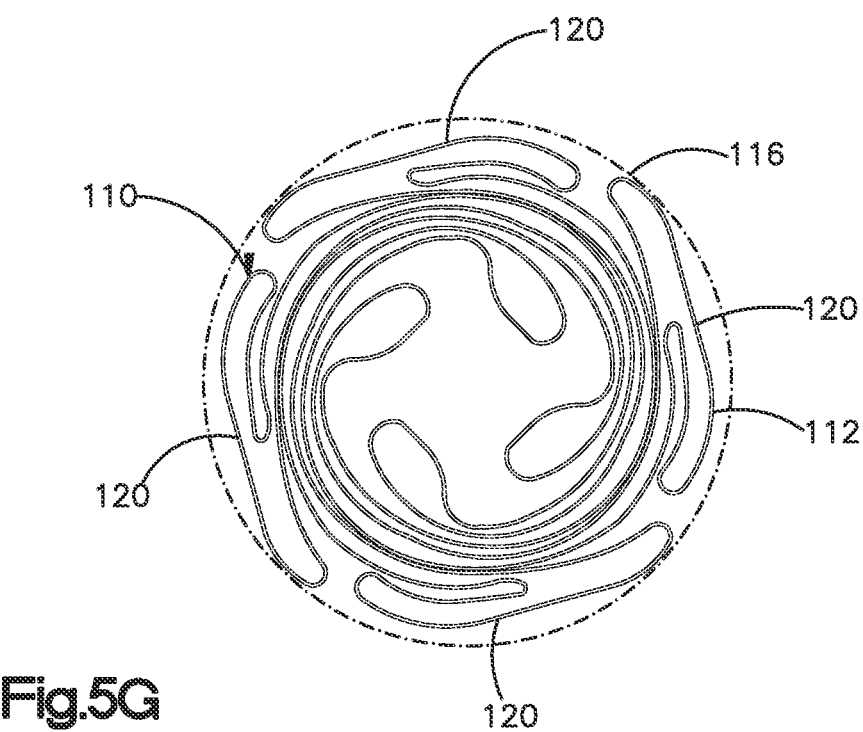
FIG. 5G is an end elevation view of the auxiliary implant illustrated in FIG. 5A, shown in a folded or collapsed insertion configuration.

Accordingly, referring to FIG. 5F, the implant assembly 19 can define four pockets 126 disposed in the internal void 23 between the implant body 112 and the primary implant 20. In particular, each pocket 126 is disposed circumferentially between adjacent nodes 120, and radially between the central body portion 118 and the primary implant 20. The pockets 126 can be separated and isolated from each other via the implant body 112, or can be placed in fluid communication with each other in the manner described above. Accordingly, a bone stimulating material 128 can be inserted into the pockets 126 so as to facilitate bone growth into the implant assembly 19. The bone stimulating material 128 can be, for example, calcium phosphate, hydroxyapatite, allograft, and the like. In use, the bone stimulating material 128 promotes biological activity, such as bone in-growth and exchange of nutrients between cranial and caudal vertebral endplates.

Figure 6A:
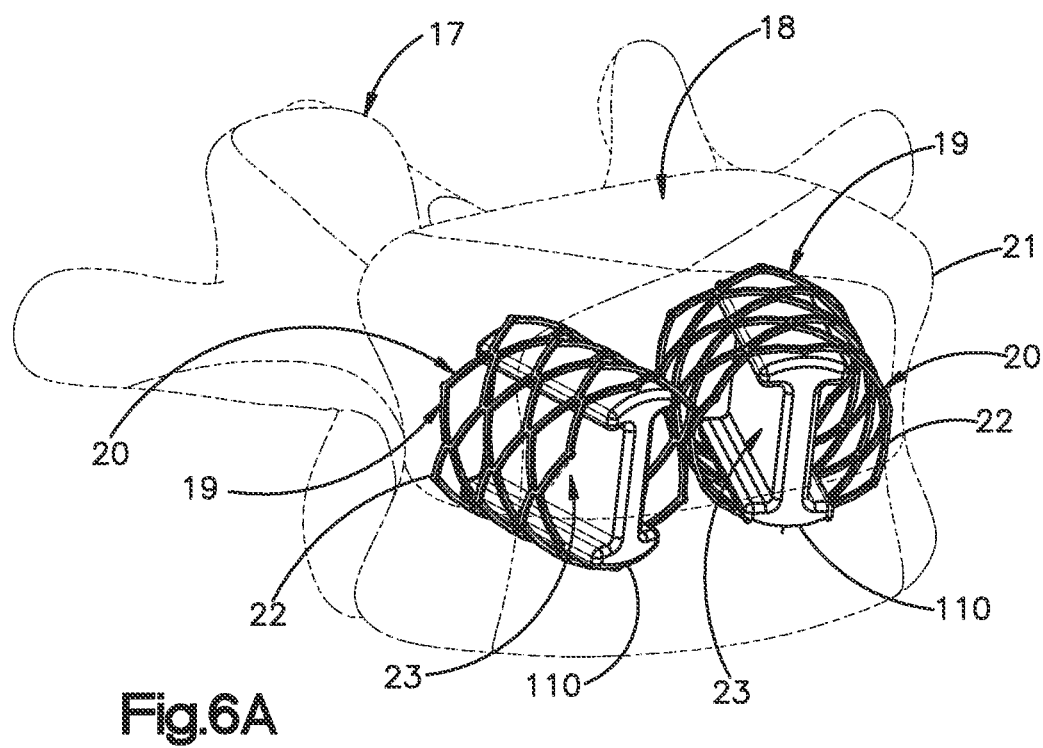
FIG. 6A is a perspective view of an implant system constructed in accordance with an alternative embodiment inserted in a target bone, the implant system including a pair of implant assemblies, each including a primary implant an auxiliary implant disposed in the primary implant, wherein the implant system is shown in an expanded configuration.
Figure 6B:
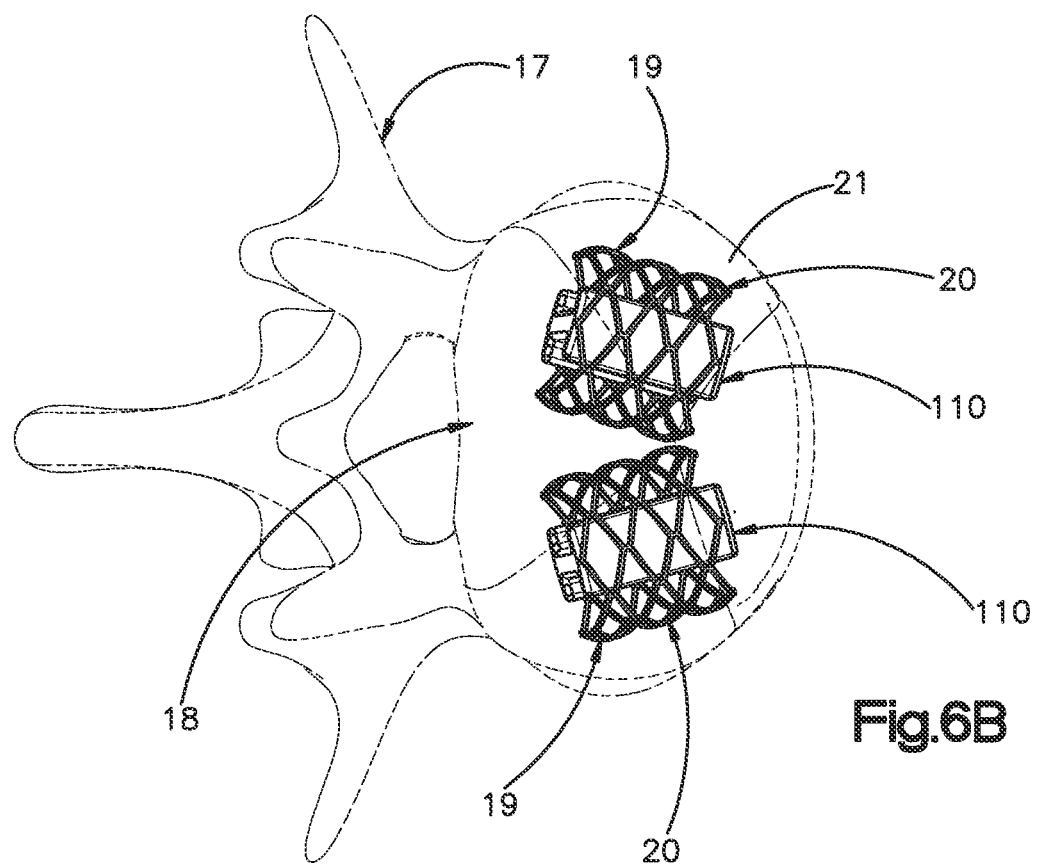
FIG. 6B is a top plan view of the implant system illustrated in FIG. 6A.
Figure 6C:
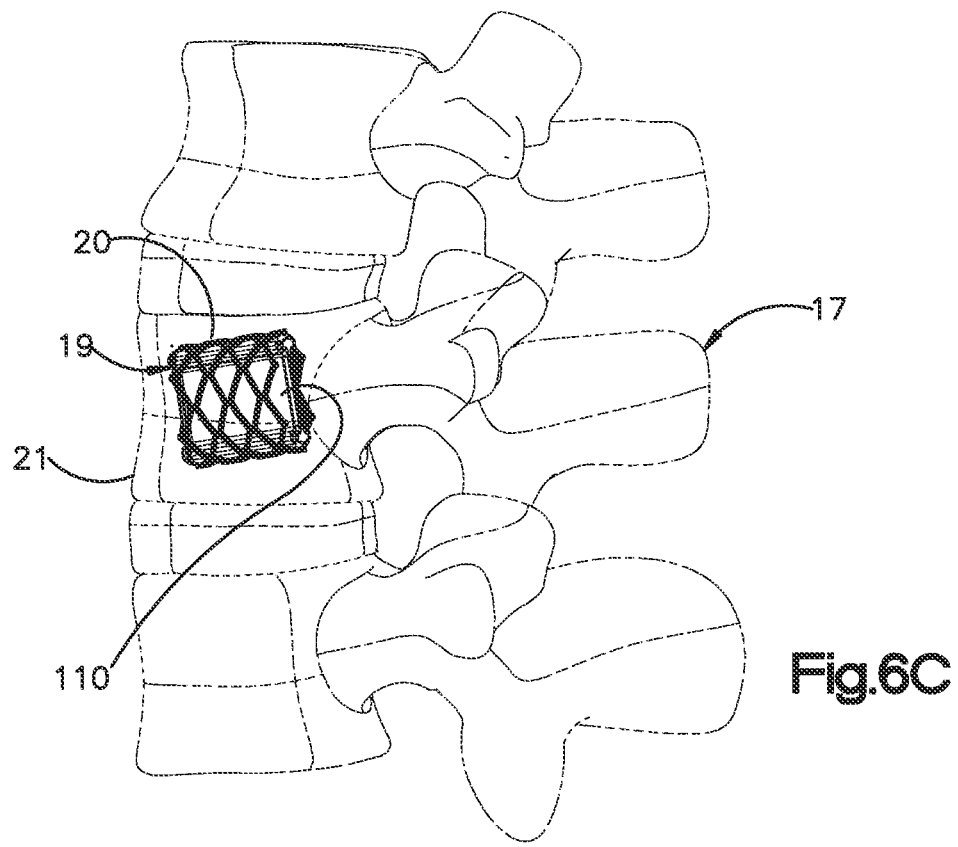
FIG. 6C is a side elevation view of one of the implant assemblies of the implant system illustrated in FIG. 6A.
Figure 6D:
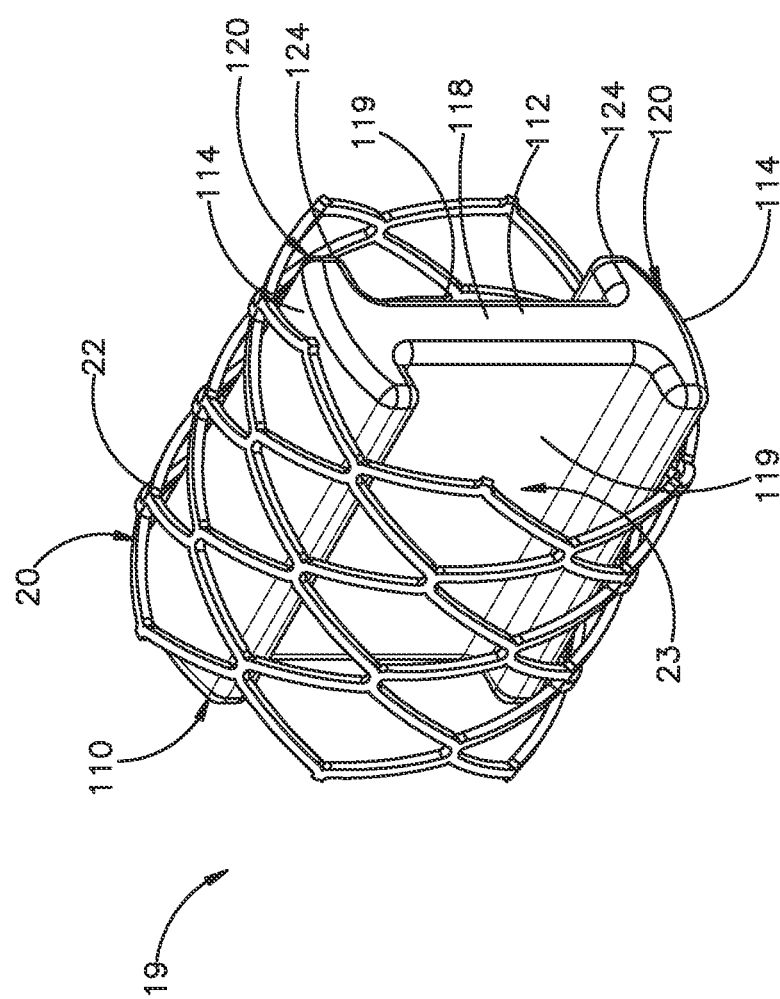
FIG. 6D is a perspective view of one of the implant assembly illustrated in FIG. 6C.
Figure 6E:
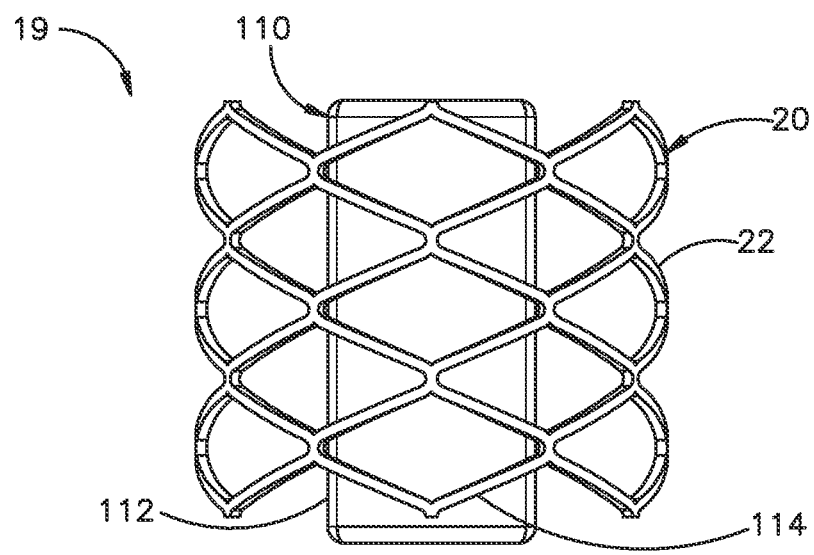
FIG. 6E is a top plan view of the implant assembly illustrated in FIG. 6C.

Referring now to FIGS. 6A-G, the auxiliary expandable implant body 112 can be substantially I-shaped. In accordance with the illustrated embodiment, the implant body 112 defines a substantially rectangular elongate central body portion 118 having side surfaces 119 that can be shaped as desired, such as curved (e.g., concave) or substantially straight, and a pair of nodes 120 that extend radially and circumferentially out from the outer ends the implant body 112. In accordance with the illustrated embodiment, two nodes 120 are spaced circumferentially equidistantly 180° apart, though they can be spaced at consistent or variable spacing about the implant body 112. Furthermore, the auxiliary implant 110 can include any number of nodes 120 as desired. The implant 110 is expandable from a compressed or collapsed configuration illustrated in FIG. 6G to the expanded position, for instance as illustrated in FIG. 6A.

Figure 6F:
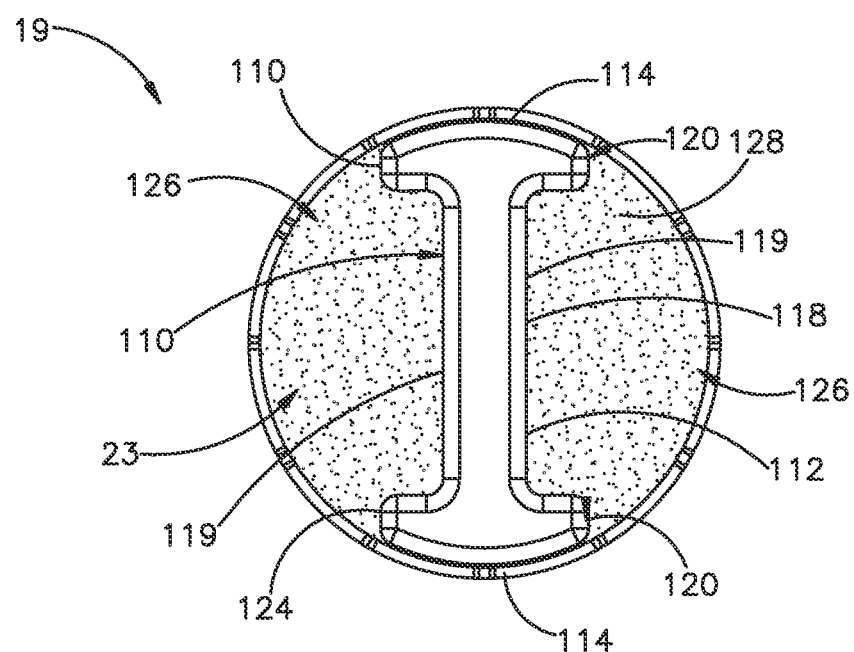
FIG. 6F is an end elevation view of the implant assembly illustrated in FIG. 6E, showing bone stimulating material injected into pockets disposed between the primary and auxiliary implants.
Figure 6G:
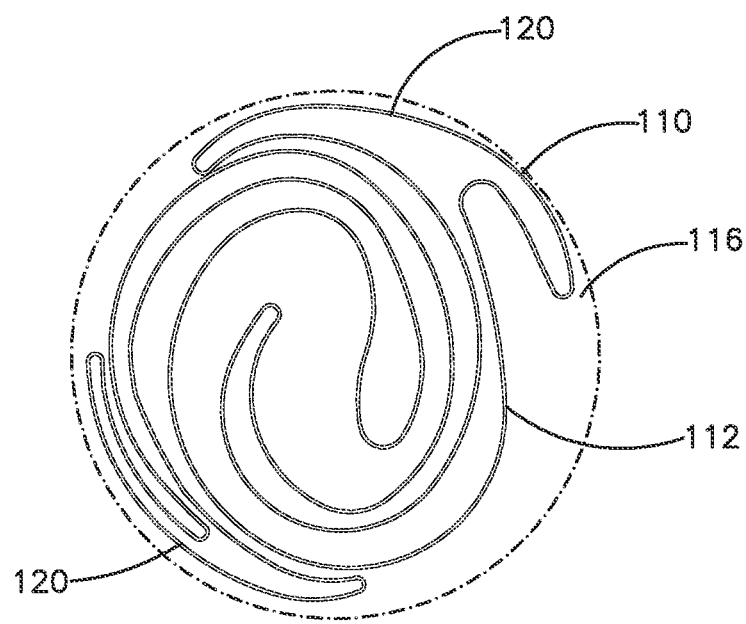
FIG. 6G is an end elevation view of the auxiliary implant illustrated in FIG. 6A, shown in a folded or collapsed insertion configuration.

Accordingly, referring to FIG. 6F, the implant assembly 19 can define a pair of pockets 126 disposed in the internal void 23 between the implant body 112 and the primary implant 20. In particular, each pocket 126 is disposed circumferentially between adjacent nodes 120, and radially between the central body portion 118 and the primary implant 20. The pockets 126 can be separated and isolated from each other via the implant body 112, or can be placed in fluid communication with each other in the manner described above. Accordingly, a bone stimulating material 128 can be inserted into the pockets 126 so as to facilitate bone growth into the implant assembly 19. The bone stimulating material 128 can be, for example, calcium phosphate, hydroxyapatite, allograft, and the like. In use, the bone stimulating material 128 promotes biological activity, such as bone in-growth and exchange of nutrients between cranial and caudal vertebral endplates.

Figure 6H:
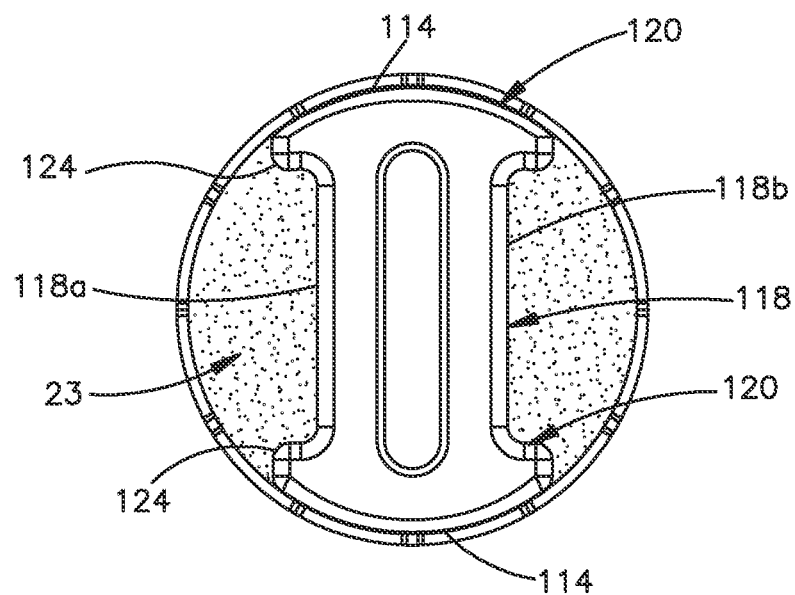
FIG. 6H is an end elevation view of an implant assembly similar to the implant assembly illustrated in FIG. 6F, but constructed in accordance with an alternative embodiment.

Referring now to FIG. 6H, the auxiliary expandable implant body 112 can be substantially double I-beam shaped. In accordance with the illustrated embodiment, the central body portion 118 of the implant body 112 defines a pair of parallel spaced elongate legs 118a and 118b, each having side surfaces 119 that can be shaped as desired, such as curved (e.g., concave) or substantially straight, and a pair of nodes 120 that extend radially and circumferentially out from the outer ends the legs 118a and 118. In accordance with the illustrated embodiment, two nodes 120 are spaced circumferentially equidistantly 180° apart, though they can be spaced at consistent or variable spacing about the implant body 112. Furthermore, the auxiliary implant 110 can include any number of nodes 120 as desired.

The expandable auxiliary implant 110 can be fabricated using any desirable manufacturing technique as desired. For instance, a plurality of biocompatible and inflatable thin-walled sheets (of polymeric material, for example) can be welded together, either ultrasonically or via light beam so as to form the implant body 112 that, expand into the above-illustrated configurations when filled with the bone filler material 123. For example, the expandable implant 110 can be manufactured by bonding two or more sheets of PEEK (or other biocompatible materials that are either inflatable or unfoldable).

Referring now to FIGS. 7A-D, the implant assembly 19 can include the expandable primary implant 20 and the expandable auxiliary implant 110 constructed in accordance with an alternative embodiment. For instance, the auxiliary implant 110 can include an implant body 112, which includes a central body portion 118 and an expandable balloon or bladder 140 that can be inserted into the central body portion 118 in a collapsed configuration, and injected with the bone filler material 123 under pressure, which causes the bladder 140 to expand to an expanded configuration. The bladder 140 can be made from any suitable expandable material, such as a polyurethane family polymer, for instance PCU (polycarbonate-urethane), such as Bionate. The central body portion 118 can likewise be made from any suitable material (which can be expandable or rigid), such as metal or a rigid polymer, such as PEEK, to locally restrain the bladder 140 and allow the bladder to define nodes 120 that contact the primary implant 20.

In accordance with the illustrated embodiment, the central body portion 118 is illustrated as an annular sleeve, and elongate along a central axis 142 that can be coextensive with the central axis 24 of the primary implant 20. The central body portion 118 defines an interior 115 that can be cylindrical or alternatively shaped as desired. The auxiliary implant 110 further defines at least one opening illustrated as a slot 144, such as a plurality of slots 144 that extend through the central body portion 118. Alternatively, the auxiliary implant 110 can be include a plurality of linkages 26 as described above with respect to the primary implant 20 (see FIGS. 2A-D). The central body portion 118 can include any number of slots or openings 144 spaced circumferentially and/or axially as desired. As will be appreciated from the description below, the slots 144 can define node locations for the auxiliary implant body 112. Thus, the slots 144 can be spaced circumferentially equidistantly as illustrated, or can define variable circumferential distances therebetween as desired.

Figure 7A:
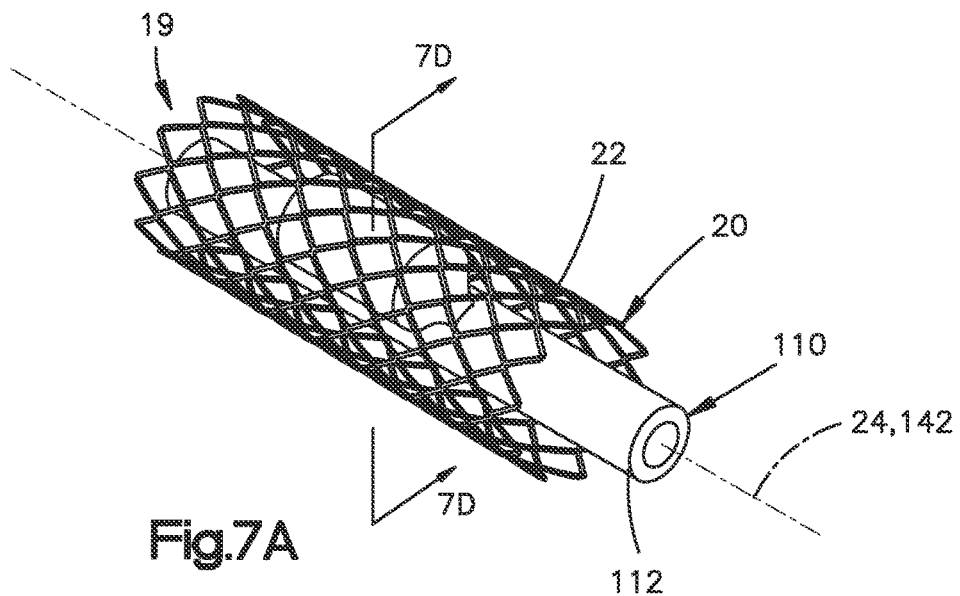
FIG. 7A is an implant assembly including a primary implant, and an auxiliary implant constructed in accordance with an alternative embodiment, showing the implant assembly in an expanded configuration.
Figure 7B:
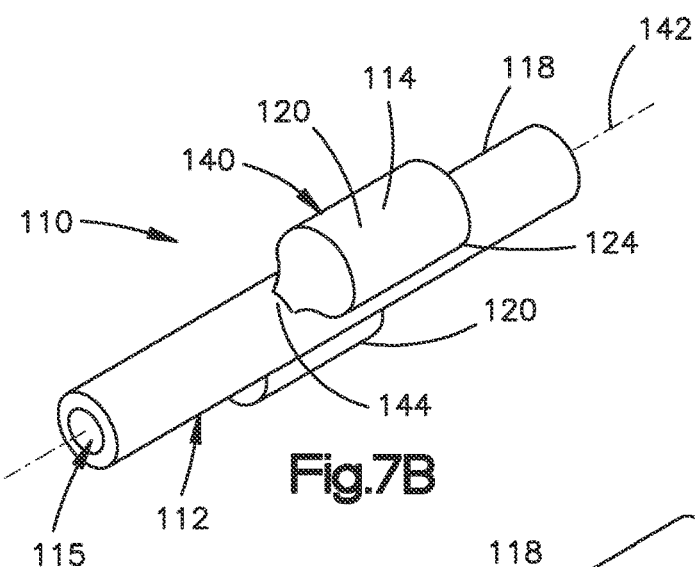
FIG. 7B is a perspective view of the auxiliary implant illustrated in FIG. 7A.
Figure 7C:
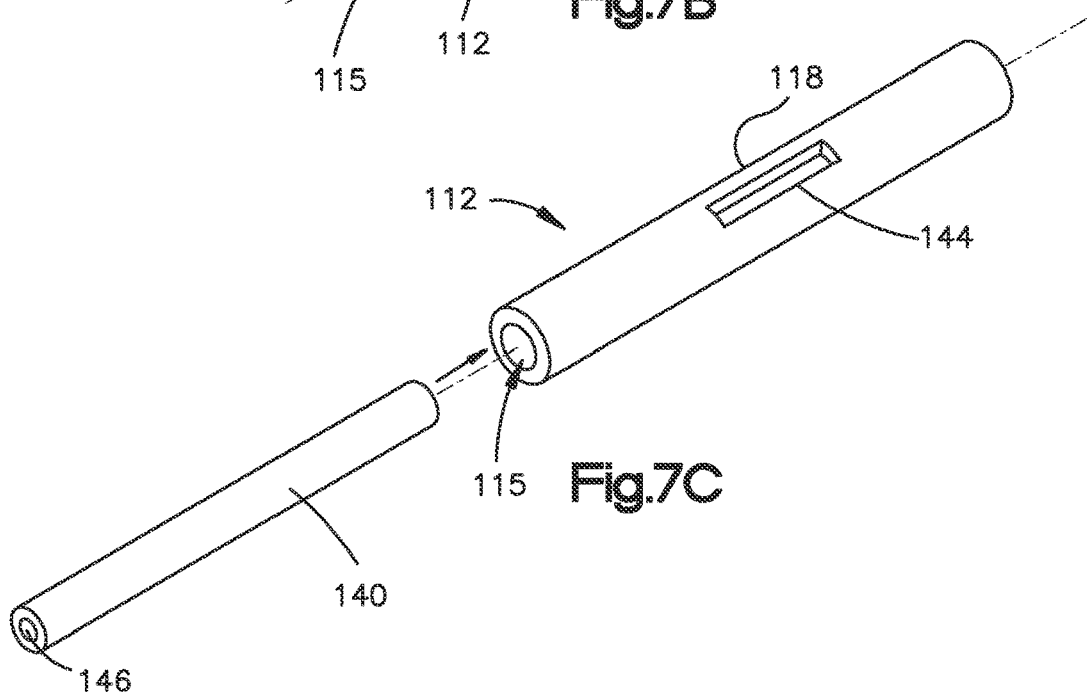
FIG. 7C is a perspective view of the auxiliary implant illustrated in FIG. 7B, showing a bladder being inserted into a support sleeve in a collapsed configuration.

During operation, the expandable bladder 140 can be placed inside the interior 115 of the central body portion 118 in its collapsed configuration (see FIG. 7C). The auxiliary implant 110, in its collapsed configuration, can then be placed inside the primary implant 20 which can be expanded prior to insertion of the auxiliary implant 110. Alternatively, the central body portion 118 can first be inserted inside the primary implant 20, and the expandable bladder 140, in its collapsed configuration, can subsequently be inserted into the interior of the central body portion 118. The bladder 140 can include a port 146 at its proximal end that can be coupled to a docking/dedocking mechanism that is configured to deliver bone filler material 123 into the internal void 145 of the bladder 140. The bladder 140 is compliant and thus stretchable as the bone filler material 123 is inserted through the port 146 so as to create a positive pressure in the internal void 145. For instance, a liquid such as liquid bone cement can be injected into the port 146 that causes the bladder 140 to expand, in turn causing portions of the bladder 140 to extend through the openings 144 so as to define nodes 120 that extend out from the central body portion 118. Because the bladder 140 stretches in situ, the bladder 140 increases in outer surface area as it expands in situ. The bone cement then hardens once the cement fully polymerizes, typically no later than 30 minutes.

As the bladder 140 expands inside the central body portion 118, a portion of the bladder 140 extends through the slots 144 so as to create a mushroom shaped nodes 120, each defining a neck 122 that extends through the slot 144 and a stabilizing support foot 124 that extends out from the slot 144 defines a greater circumferential dimension than the neck 122. support feet 124 define respective radially outer contact surfaces 114 configured to contact the primary implant body 22 in the manner described above. Thus, the bone filler material 123 can be inserted into the bladder 140 until the bladder 140 has expanded to the point that the contact surfaces 114 abut the inner surfaces of the primary implant body 22. As illustrated in FIG. 7D, the auxiliary implant 110 can include a pair of slots 144 spaced 180° apart from each other, thereby defining a pair of nodes 120. Thus, the auxiliary implant 110 can be substantially I-shaped as illustrated in FIG. 7D. As illustrated in FIG. 7E, the auxiliary implant 110 can include three slots 144 spaced 120° apart from each other, defining three nodes 120. Thus, the auxiliary implant 110 can be substantially triangular as illustrated in FIG. 7E. As illustrated in FIG. 7F, the auxiliary implant 110 can include four slots 144 spaced 90° apart from each other, defining four nodes 120. Thus, the auxiliary implant 110 can be substantially X-shaped. It should thus be appreciated that the auxiliary implant 112 (for instance the bladder 140) can be compliant and stretchable in response to the introduction of bone filler material 123, whereas the auxiliary implant 112 of the type illustrated in FIGS. 4-6 can be constructed non-compliant and rigid The nodes 120 of the auxiliary implant 112 and the primary implant 20 can define pockets that can be filled with a bone stimulating material in the manner described above with respect to FIG. 4E.

Figure 8C:
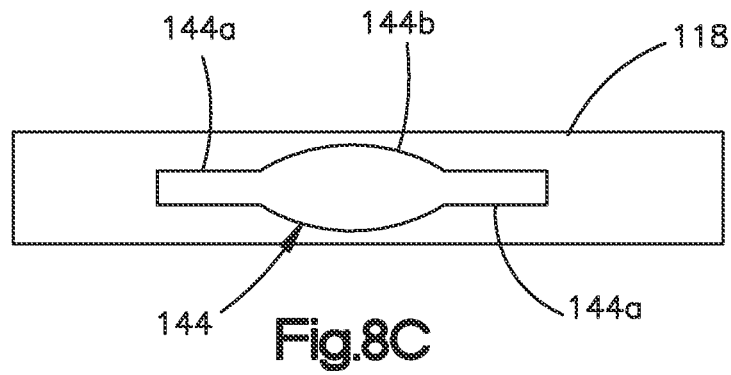
FIG. 8C is a top plan view of an enlarged an implant sleeve constructed in accordance with an alternative embodiment.
Figure 8D:
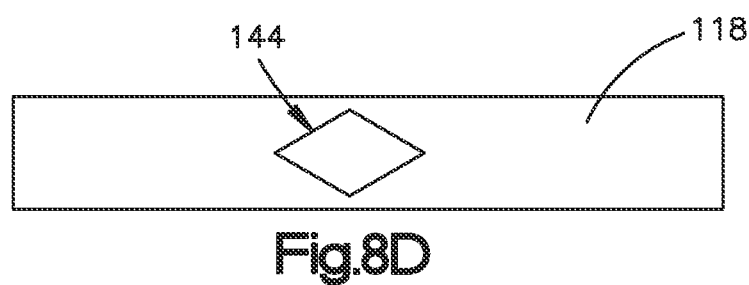
FIG. 8D is a top plan view of an enlarged an implant sleeve constructed in accordance with another alternative embodiment.

Referring now to FIGS. 8A, the auxiliary implant body 112 can define bifurcated slots 144 that are axially aligned. Furthermore, the slots 144 can be arranged in columns that overlap each other circumferentially as illustrated in FIG. 8B. Thus, the slots 144 can be arranged in the central body portion 118 in any orientation and configuration as desired. Furthermore, the slots 144 can be shaped as desired. For instance, the slots 144 can be rectangular and elongate in a direction substantially parallel to the central axis 142 as illustrated in FIG. 7C. Alternatively, as illustrated in FIG. 8C, the slots 144 can be keyhole-shaped, having outer portions 144a and a middle portion 144b that is disposed between the outer portions 144a and wider than the outer portions 144a. Alternatively, one or both of the outer portions 144a can be wider than the middle portion 144b. Alternatively still, as illustrated in FIG. 8D, the slots 144 can be diamond-shaped. It is appreciated that the size and shape of the slots 144 can at least partially determine the size and shape of the node 120 that extends through the slots 144.

Figure 9:
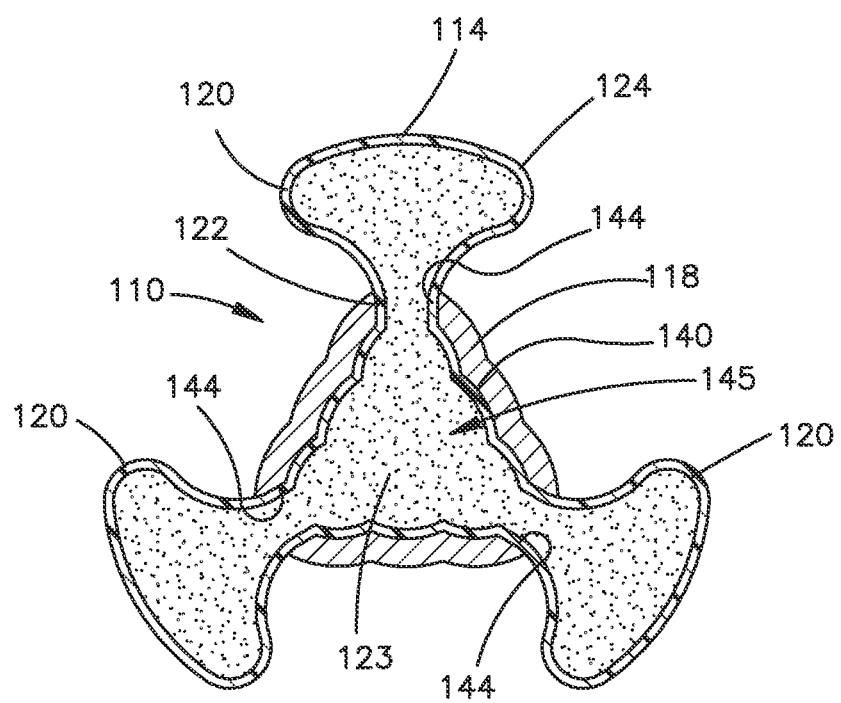
FIG. 9 is a sectional end elevation view of an auxiliary implant assembly similar to the auxiliary implant assembly illustrated in FIG. 7E, but wherein the sleeve is compliant and expandable in accordance with an alternative embodiment.

While the central body portion 118 can remain substantially rigid as the bladder 140 expands from the collapsed configuration to the expanded configuration as illustrated in FIGS. 7A-7F, it is appreciated that the central body portion 118 can alternatively be compliant, and part or all of the central body portion 118 expand in response to outward expansion forces imparted from the expanding bladder 140 onto the central body portion 118. For instance, as illustrated in FIG. 9, the central body portion 118 can expand radially outward at locations adjacent the slots 144 as the bladder 140 expands through the slots 144.

While the auxiliary implant 112 is placed inside the primary implant 20 and expanded in accordance with the embodiment illustrated in FIG. 7A, it should be appreciated that the auxiliary implant 112 can define a stand-alone implant that is inserted into the target bone, such as the vertebral body portion of a vertebra in its collapsed configuration, and subsequently expanded to restore height to the vertebral body portion.

Referring now also to FIGS. 10A-D, the implant system 18 can include at least one expandable implant assembly 19 as described above, along with an implant insertion assembly 50 that facilitates the insertion and expansion of the primary and auxiliary implants 20 and 110 within the target bone. The expandable implant assembly 19 may be implanted into the vertebral body portion 21 via any approach now or hereafter known in the art including, for example, via an anterior approach, a mono-axial or bilateral approach, a trans-pedicular approach, para-pedicular approach, extra-pedicular approach, trans-psoas, and the like.

In accordance with the embodiment illustrated in FIGS. 10A-J, implant assembly 19 is inserted via a bilateral, transpedicular approach. The insertion assembly 50 can include an opening assembly 52 configured to create an opening through the target bone that provides a guide path through which the implant assembly 19 is implanted. The opening assembly 52 includes a cannulated body 62a, an opening device 62b that is received inside the cannulated body 62a, and an aiming device 54 that supports the opening assembly 52.

The elongate cannulated body 62a that defines a proximal end 64a and an opposed distal end 66a, and a cannula 68a that extends through the cannulated body 62a from the proximal end 64a to the distal end 66a along the direction of elongation. The cannulated body 62a is substantially straight and is connected to a handle 67a at the proximal end 64a. The cannula 68a can extend through the respective handles 67a. The opening device 62b is sized to be received in the cannula 68a, and defines a proximal end 64b and an opposed distal end 66b. The opening device 62b includes a handle 67b coupled to the proximal end 64b. The distal end 66b can provide a cutting blade 65 illustrated as a cutting edge or alternatively configured opening member that is configured to cut through the target bone. The opening device 62b can further define a cannula 68b that extends from the proximal end 64b to the distal end 66b and through the handle 67b. Alternatively, the opening device 62b can be a solid body. The insertion assembly 50 can include a pair of symmetrically shaped opening assemblies 52 that can be inserted into the target vertebral body portion 21 when, for instance, implanting a pair of expandable implant assemblies 19.

During operation, the opening devices 62b can be inserted into the proximal end 64a of the cannulated body 62a, such that the cutting blade 65 extends out from the distal end 66a of the cannulated body 62a. In accordance with one embodiment, the opening devices 62b can be inserted into the vertebra 70 along a transpedicular approach. A stab incision can be used to access the pedicles 72 of the target vertebra 17, under intra-operative radiological observation. Both pedicles 72 of the targeted vertebra 17 can be opened by driving the distal cutting blades 65 into the respective pedicles 72, such that the opening devices 62b penetrate the cortical bone of the corresponding pedicles 72. The opening devices 62b can then be translated along the pedicle axes, so as to perforate the arched channel through the cancellous bone within the vertebral body portion 21.

The aiming device 54 includes a body 78 and a pair of spaced apertures 80 extending through the body 78 sized to receive the corresponding pair of cannulated bodies 62a. The apertures 80 are oriented so as to aim the cannulated body 62a, and thus the opening device 62b, with the pedicle 72 along a desired insertion path into the vertebral body portion 21 of the vertebra 17 so as to create an insertion channel 73 in the vertebral body portion 21.

Once the opening devices 52 have been inserted into the vertebra 70, the components of the expandable implant assembly 19 can be inserted into the channel 73 that has been formed in the vertebral body portion 21. In particular, the implant assembly components can be inserted through the cannula 68b of the opening device 62b, or the opening device 62b can be removed from the cannulated body 62a, and the implant assembly components can be inserted through the cannula 68a of the cannulated body 62a. For instance, the opening device 62b can be constructed as a solid body. However, even if the opening device 62b is cannulated, the implant assembly components are inserted through the cannula 68b of the opening device 62b, it can still be said that the implant assembly components are implanted into the target bone through a guide path that is defined the cannula 68a. The guide path can further be defined by the cannula 68b in accordance with certain embodiments. For the purposes of illustration, the opening device 62b is shown removed from the cannulated body 62a after the channel 73 has been formed.

Figure 10D:
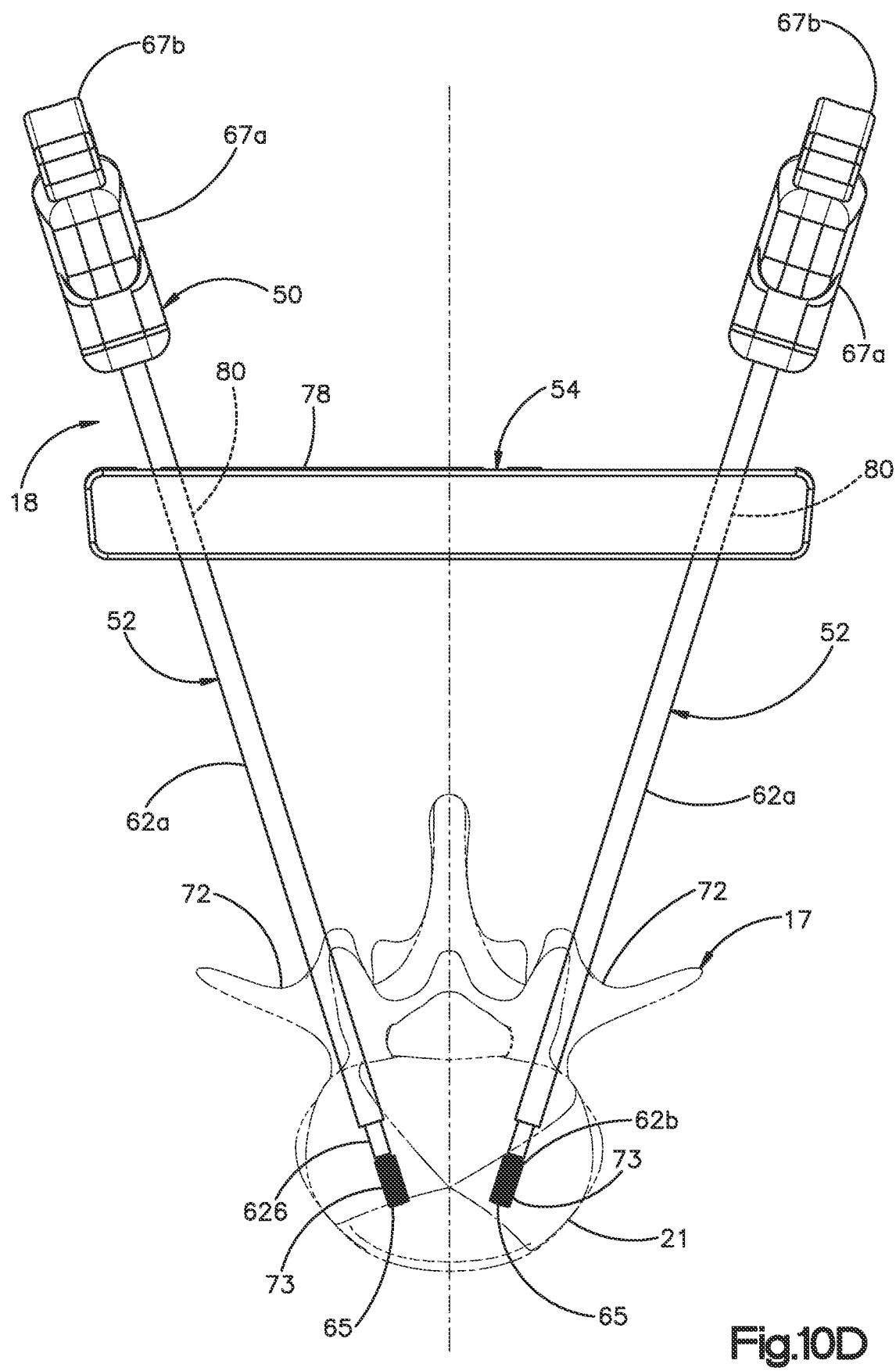
FIG. 10D is a top plan view of the insertion assembly installed in a target vertebral body through the pedicle.
Figure 10E:
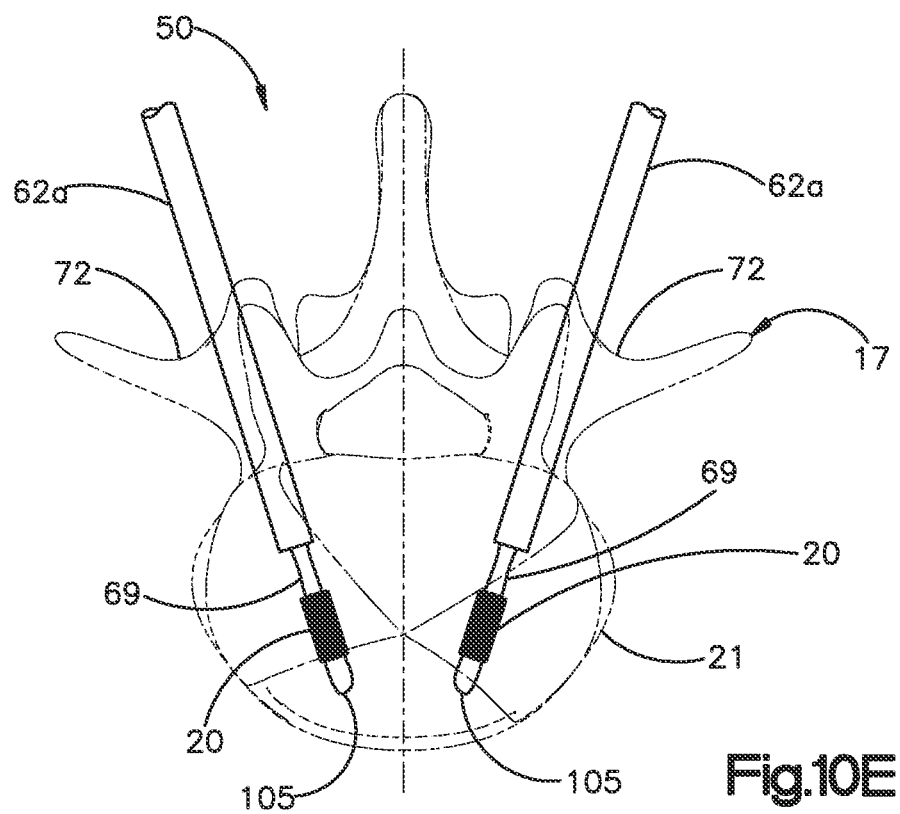
FIG. 10E is a top plan view of the primary implant and an expansion body inserted into the target vertebral body by the insertion assembly illustrated in FIG. 10D.

Referring now also to FIG. 10E, the insertion assembly 50 further includes an expansion body 69 that can be made from rubber, plastic, or other suitable material that provides an expandable bladder or other flexible member configured to occupy the internal void 23 of the implant body 22. The expansion body 69 is inserted through the cannulated body 62a and into the primary implant 20 that has been implanted in the vertebral body portion 21 of the vertebra 17. For instance, the primary implant 20 can travel inside the cannulated body 62a along a guide wire that is aligned with the channel 73. Alternatively, the expandable body 69 can be pre-inserted into the implant 20, and the expansion body 69 and the implant 20 can be inserted into the channel 73 together in unison.

Figure 10F:
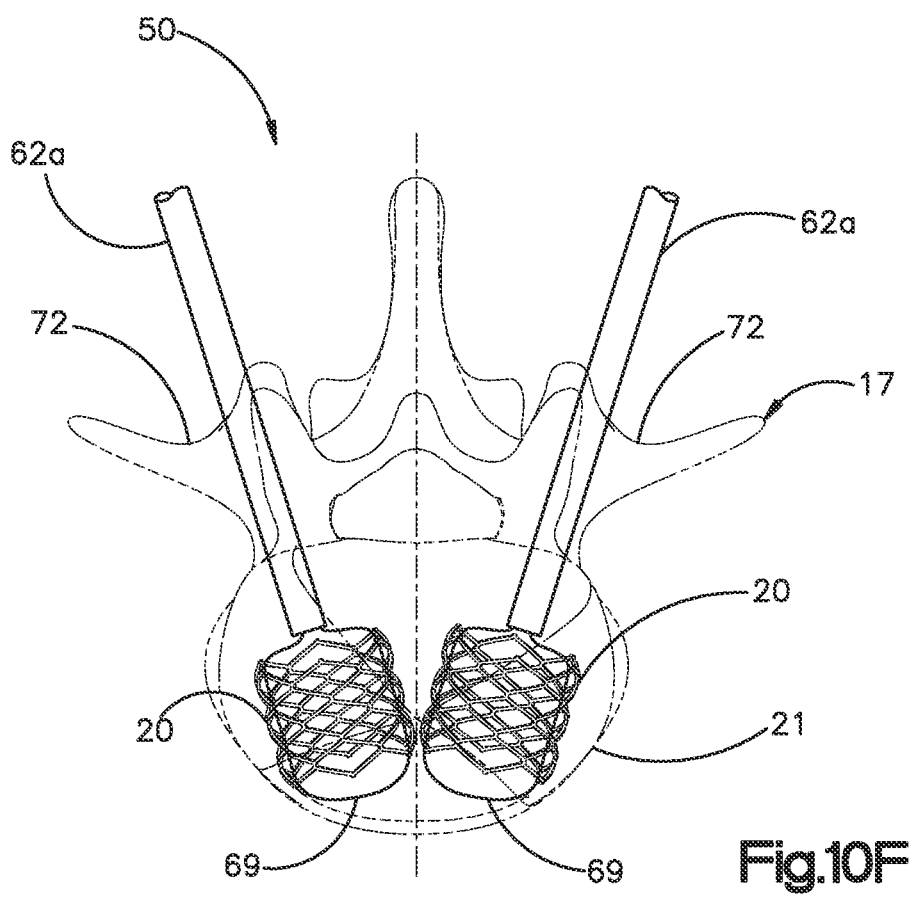
FIG. 10F is a top plan view similar to FIG. 10E, but showing the expansion body in an expanded configuration biasing the primary implant to an expanded configuration.
Figure 10G:
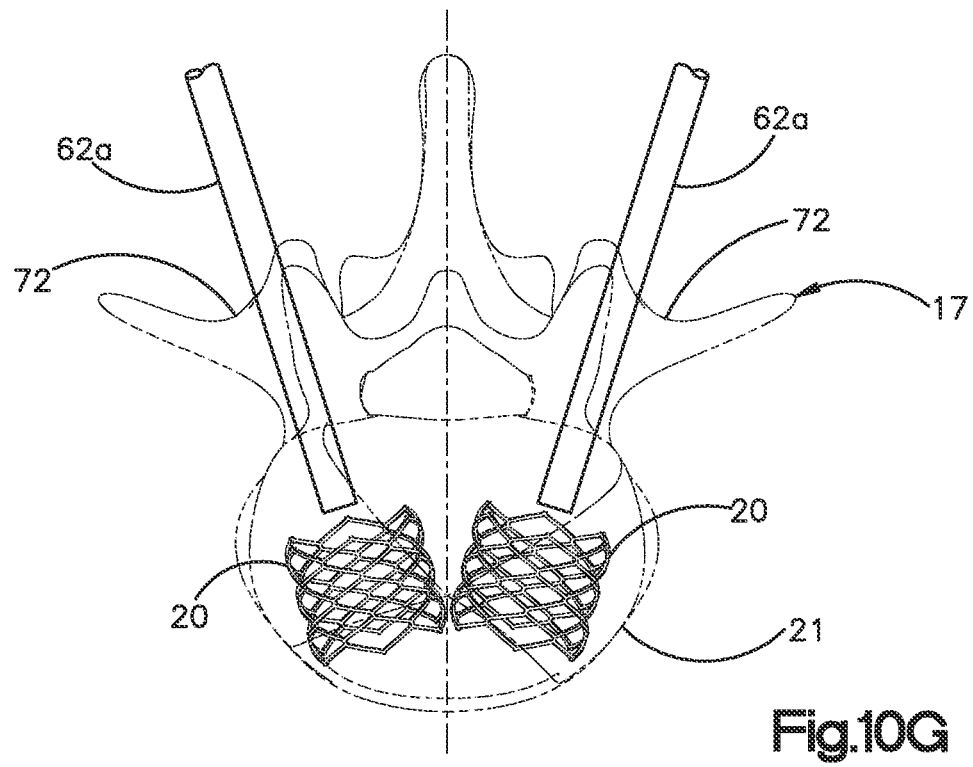
FIG. 10G is a top plan view similar to FIG. 10F, but showing the expansion body deflated and removed from the primary implant, which remains in its expanded configuration.

The expansion body 69 is closed at a distal end 105, and define a port at an opposed proximal end, such that, as illustrated in FIG. 10F, an expansion media can be inserted through the cannulated body 62a and the proximal port and into the expansion body 69, which can be a balloon that expands inside the primary implant 20. The expansion media can be any fluid as desired, such as air, saline solution, water, or the like. As the expansion body 69 expands, it imparts a radially outward force on the body of the primary implant 20, which urges the primary implant 20 to expand to its expanded configuration as described above. Once the primary implant 20 has expanded, the expansion media can be removed from the expansion body 69, which causes the expansion body 69 to contract. For instance, a docking and dedocking mechanism can be coupled to the port of the expansion body 69 so as to introduce and remove the expansion media into and from the expansion body 69. The expansion body 69 can then be removed from the cannulated body 62a as illustrated in FIG. 10G. Thus, it can be said that the expansion body 69 is temporarily implanted in the target vertebral body 21.

As described above, the primary implant plastically expands to its expanded configuration illustrated in FIG. 10G. Accordingly, after the expansion body 69 is removed, the plastically deformed primary implant 20 remains within the interior volume of the vertebral body portion 21, and is configured to withstand the intra-operative, temporary forces (which can be between approximately 100N and approximately 200N) experienced by the spine of a patient lying in a prone or supine position on the operating table.

Figure 10H:
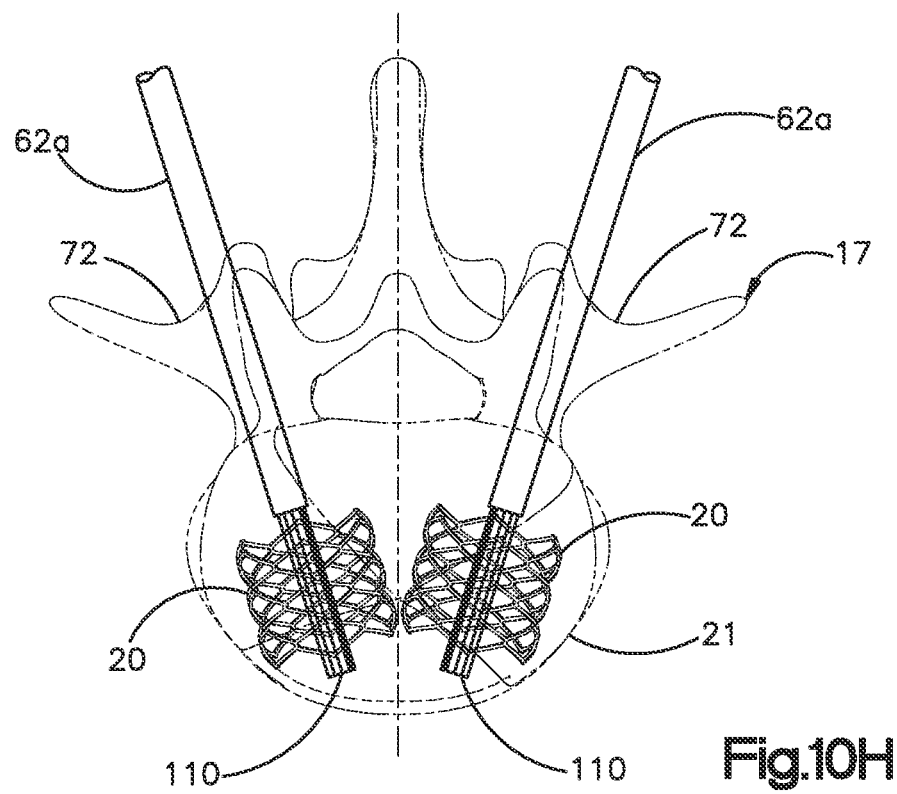
FIG. 10H is a top plan view similar to FIG. 10G, but showing the auxiliary implant inserted into the expanded primary implant in a collapsed configuration via the insertion assembly.

Referring now also to FIG. 10H, once the expansion body has been removed, the auxiliary implant 110 can be inserted through the cannulated body 62a and into the internal void 23 of the primary implant 20. The auxiliary implant 110 is illustrated as the triangular-shaped implant described above with reference to FIGS. 1D and 4A-F, though it should be appreciated that the auxiliary implant 110 having any suitable shape can be inserted inside the primary implant 20 in its collapsed or insertion configuration. The auxiliary implant 110 can be inserted into the cannulated body 62a surrounded by the sleeve 116 (FIG. 4F) that maintains the implant 110 in its collapsed configuration. The sleeve 116 can be removed once the implant 110 has been inserted into the cannulated body 62a, or can be removed once the implant 110 has been inserted into the primary implant 20.

Figure 4H:
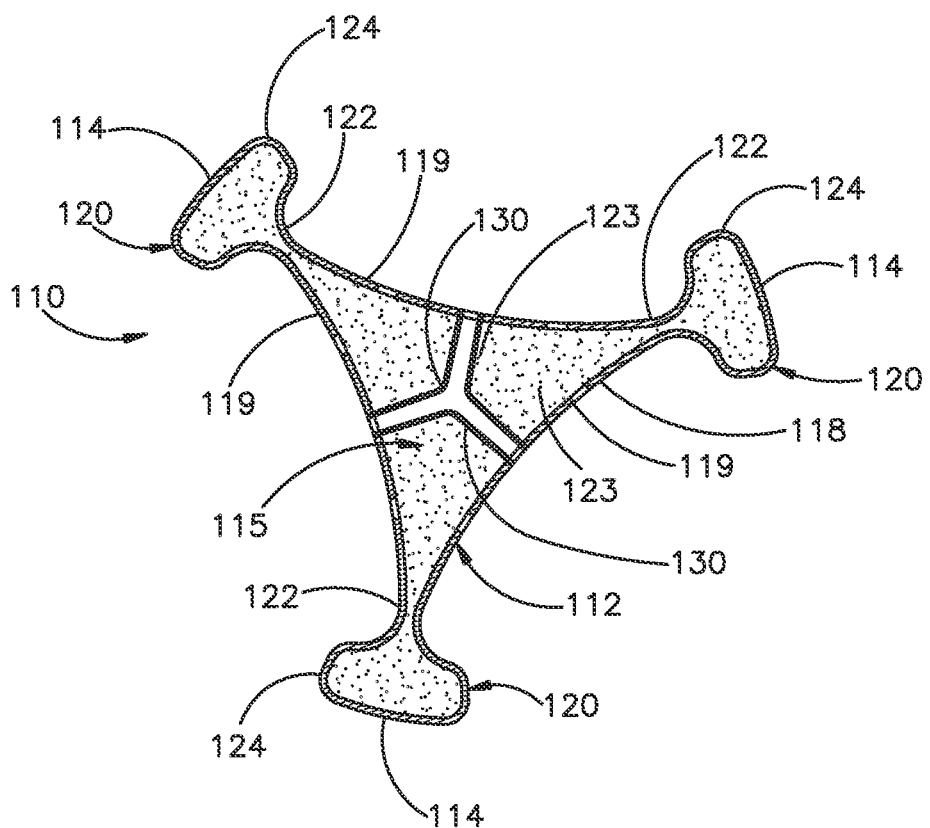
FIG. 4H is a sectional end elevation view of the auxiliary implant illustrated in FIG. 4G.
Figure 10I:
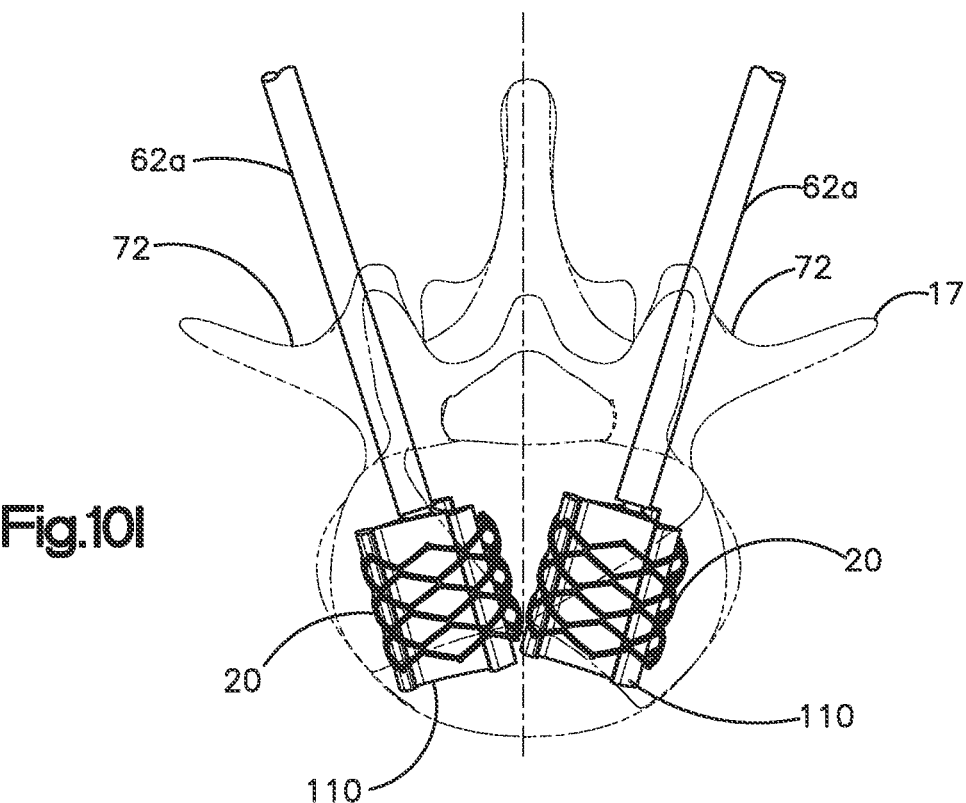
FIG. 10I is a top plan view similar to FIG. 10H, but showing the auxiliary implant expanded to its expanded configuration inside the primary implant.
Figure 10J:
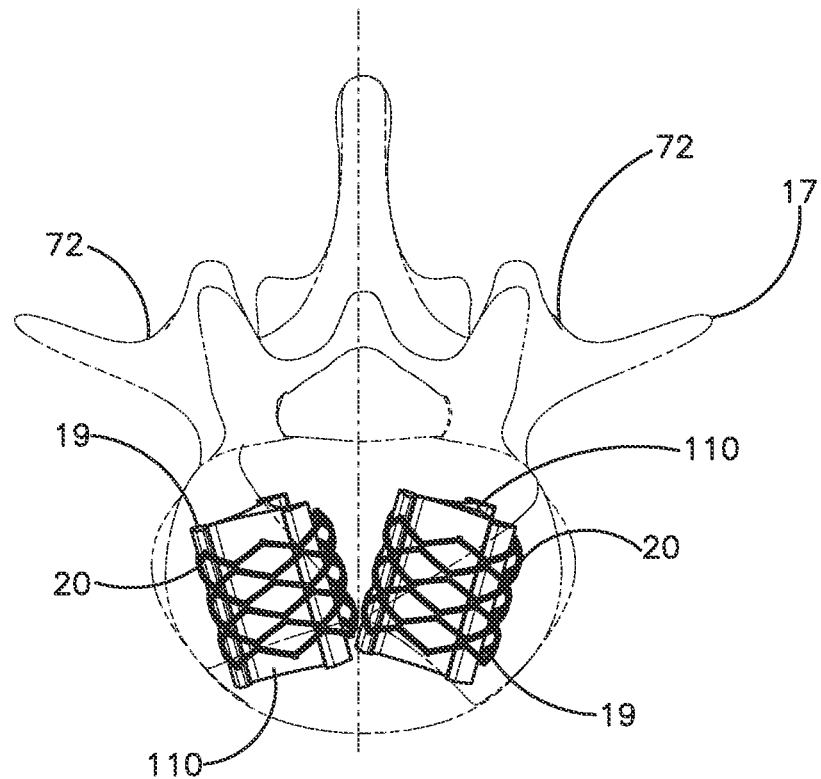
FIG. 10J is a to plan view similar to FIG. 10I, but showing the insertion assembly removed from the target vertebra.

Referring to FIGS. 4H and 10I, once the auxiliary implant 110 is disposed in the internal void of the primary implant 20, the proximal end of the auxiliary implant 110 can be coupled to a source of bone filler material 123, such as for example a biocompatible bone cement. For instance, a secondary cannula can be inserted into the cannulated body 62a, and coupled to an inlet on the implant body 112 to the interior 115 at one end, and a pressurized source of bone filler material 123 at its other end. Thus, the bone filler material 123 can be injected into the interior 115 of the implant body 112, thereby causing the implant body 112 to expand inside the primary implant 20 to a size that causes the contact surfaces 114 abut the implant 20. The contact surfaces 114 can be oriented as desired, and extend cranially and caudally in accordance with one embodiment so as to absorb compression forces imparted onto the vertebral body 21. Once the bone filler material hardens, the secondary cannula and the cannulated body 62a can be twisted, pried, or otherwise actuated to break away from the expanded auxiliary implant 110 and removed from the target vertebra 17, as illustrated in FIG. 10J. The implant assembly 19 is configured to withstand the post-operative, "permanent" forces (which can be between approximately 500N and approximately 5,000N) that are experienced by the spine during normal post-operative anatomical function of the patient (e.g., standing, walking, sitting, jumping, etc). For instance, the PMMA-based bone cement can typically withstand loads greater than 10,000N under static or fatigue load modes. Accordingly, the auxiliary implant 110 can withstand higher forces than the primary implant 20.

It should be appreciated that while the primary implant 20 is expanded prior to insertion of the auxiliary implant 110 in accordance with the illustrated embodiment, the auxiliary implant 110 can be pre-installed inside the primary implant 20 in its compressed or collapsed configuration prior to implantation of the primary implant 20 in the vertebral body portion 21. Accordingly, the primary and auxiliary implants 20 and 110 can inserted into the vertebral body 21 in unison, such that expansion of the auxiliary implant 110 expands the primary implant 20. Alternatively still, the auxiliary implant 110 can be implanted into the vertebral body 21 in its compressed or collapsed configuration without the primary implant 20, and subsequently expanded to restore height to the vertebral body 21.

Referring also again to FIG. 4E, once the implant assembly 19 has been expanded inside the target vertebral body 21 in accordance with the illustrated embodiment, the bone stimulating material 128 can subsequently be inserted into at least one of the pockets 126, up to all of the pockets 126. For example, the bone stimulating material 128 can be introduced into the channel 73 (created as described with respect to FIG. 10D) under pressure, which causes the bone stimulating material 128 to flow into the pockets 126. Alternatively, the bone stimulating material 128 can be directed into the pockets 126 in any manner as desired. While the insertion assembly 50 has been illustrated as implanting a pair of implant assemblies 19 on opposed sides of the vertebral body portion 21, it should be appreciated that only a single implant assembly 19 can alternatively be implanted as desired.

Figure 11D:
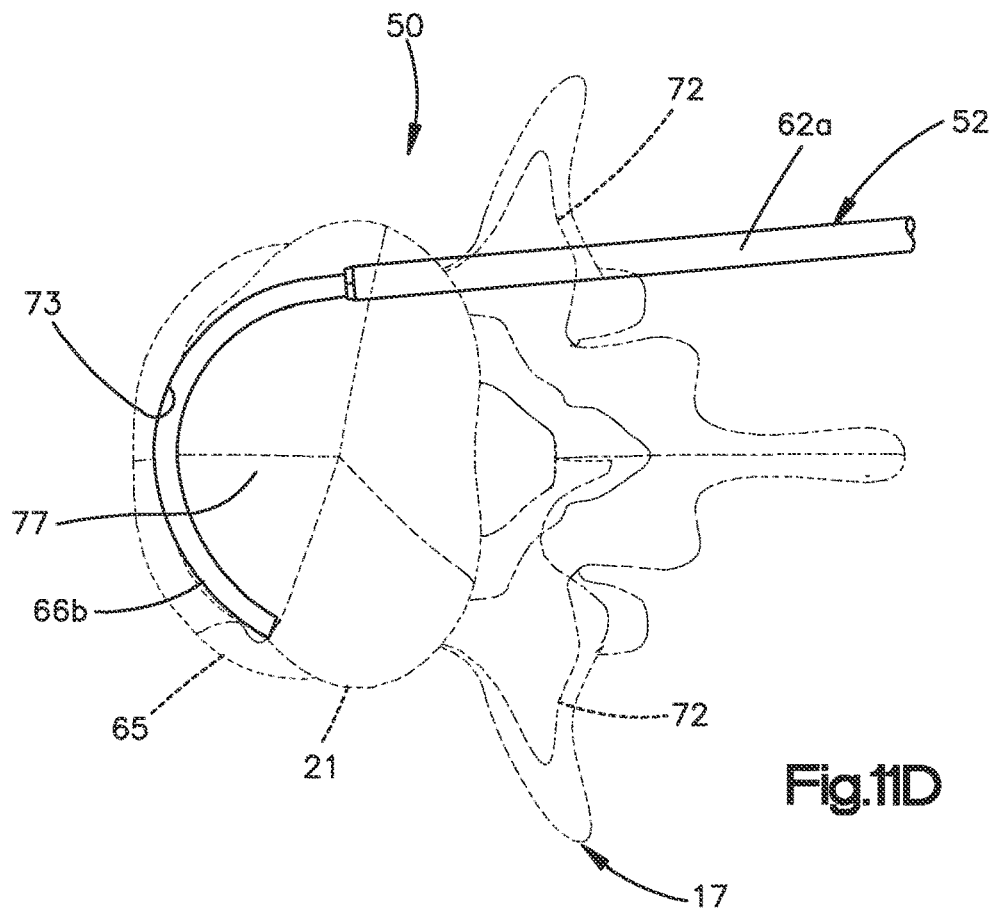
FIG. 11D is a top plan view of the insertion assembly installed in a target vertebral body through the pedicle.

Referring now to FIGS. 11A-C, the opening device 62b can be curved at a location proximate to the distal end 66b, and is further flexible, such that the distal end 66b extends in a substantially straight configuration when disposed in the cannula 68a, but is bent when disposed outside of the cannula 68a. The opening device 62b can be formed from any suitable elastic bent material, such as Nitinol (or a nickel-titanium alloy). Accordingly, as illustrated in FIG. 11D, when the opening assembly 52 is inserted into the pedicle of the target vertebra 17, and the opening device 62b is translated forward such that the distal end 66b travels out from the cannulated body 62a, the distal end 66b curves as it is driven through the cancellous bone so as to create a curved or arched channel 73. The distal end 66b can have a length sufficient such that the curved channel 73 passes through the lateral midline 77 of the vertebral body portion 21, such that the lateral midline 77 intersects the channel 73.

Figure 11E:
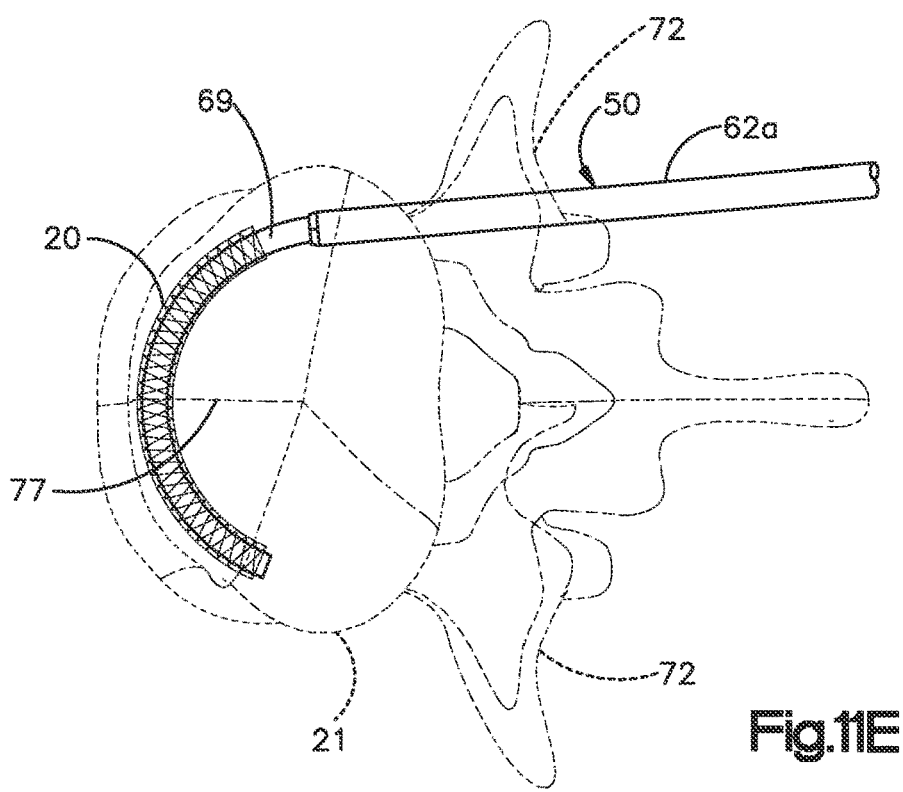
FIG. 11E is a top plan view of the primary implant and an expansion body inserted into the target vertebral body by the insertion assembly illustrated in FIG. 11D.

Next, as illustrated in FIG. 11E, the expansion body 69 is inserted through the cannulated body 62a and into the primary implant 20, and the expansion body 69 and primary implant 20 are inserted into the channel 73. The expansion body 69 and the implant 20 can be implanted together in unison, or the implant 20 can be inserted first, and subsequently the expansion body can be inserted into the implant 20. The primary implant 20 can be asymmetrical, or banana-shaped, as described above with reference to FIG. 3D such that the implant 20 defines a curvature that is substantially equal to the curvature of the curved channel 73. The implant 20 and the guide wire, for instance, or alternative structure that defines an insertion path for the implant 20 into the channel 73 can be keyed such that the implant 20 is inserted into the channel in a predetermined orientation whereby the curvature of the implant 20 will be oriented with the curvature of the channel 73.

Figure 11F:
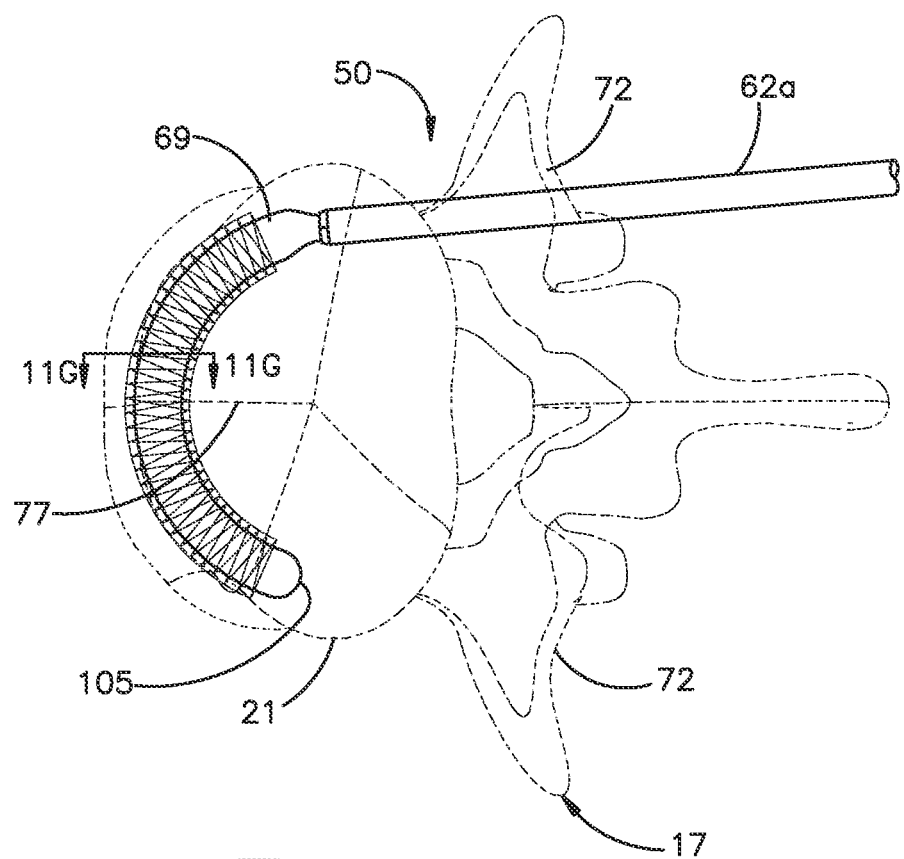
FIG. 11F is a top plan view similar to FIG. 11E, but showing the expansion body in an expanded configuration biasing the primary implant to an expanded configuration.
Figure 11G:
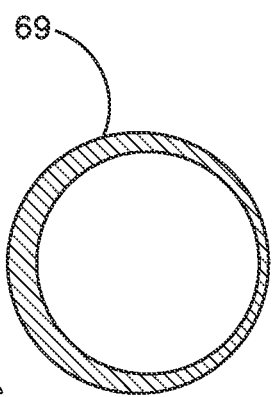
FIG. 11G is a sectional end elevation view of the expansion body illustrated in FIG. 11F, taken along line 11G-11G.

Referring to FIG. 11F, an expansion media can be inserted through the cannulated body 62a and into the expansion body 69 that causes the expansion body 69 to expand inside the primary implant 20. The expansion media can be any fluid as desired, including liquids such as contrast media, saline solution, water, mixes thereof, or the like. As the expansion body 69 expands, it imparts a radially outward force on the body of the primary implant 20, which urges the primary implant 20 to expand to its expanded configuration as described above. As illustrated in FIG. 11G, the expandable body 69 can be thicker on one side than the other, such that the body 69 becomes curved, or banana-shaped, upon expansion. Expansion of the expandable body 69 causes the primary implant 20 to expand at a location substantially central with respect to the lateral midline 77 of the vertebral body portion 21.

Figure 11H:
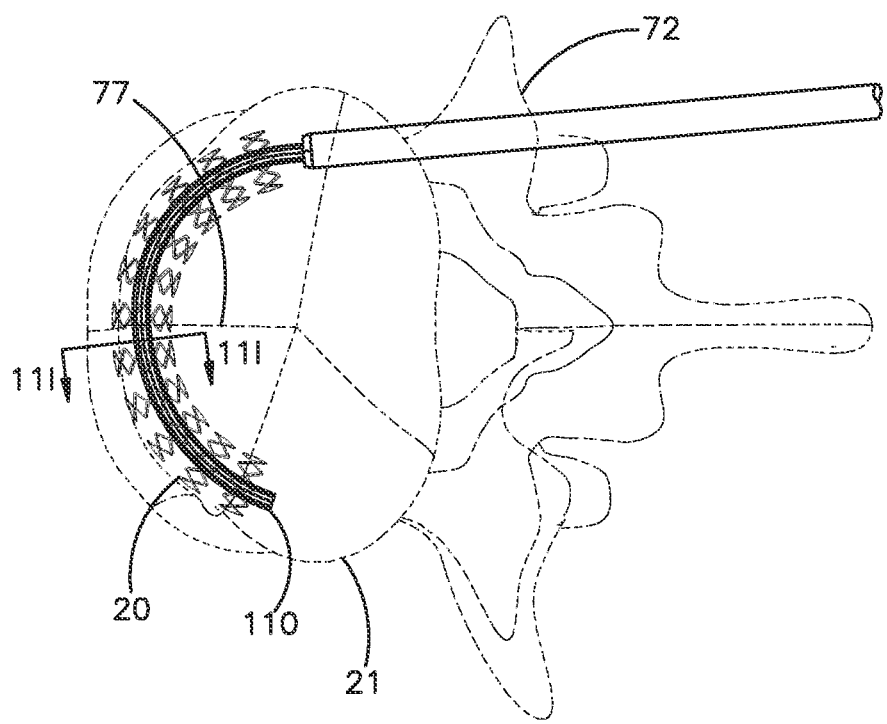
FIG. 11H is a top plan view similar to FIG. 11G, but showing the auxiliary implant inserted into the expanded primary implant in a collapsed configuration via the insertion assembly
Figure 11I:
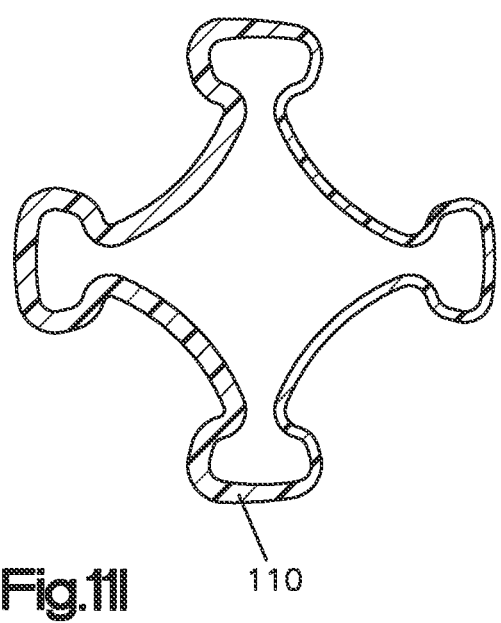
FIG. 11I is a schematic sectional end elevation view of the auxiliary implant illustrated in FIG. 11H, taken along line 11I-11I.

Referring now also to FIG. 11H, once the expansion body 69 has been deflated and removed, the auxiliary implant 110 can be inserted through the cannulated body 62a and into the internal void 23 of the primary implant 20. As schematically illustrated in FIG. 11I, the auxiliary implant 110 can be thicker at one side than another, such that the implant 110 can become curved, or banana shaped, upon expansion inside the primary implant 20. Alternatively, a plurality of "straight" auxiliary implants 110 can be implanted inside the primary implant at locations spaced from each other.

Figure 11J:
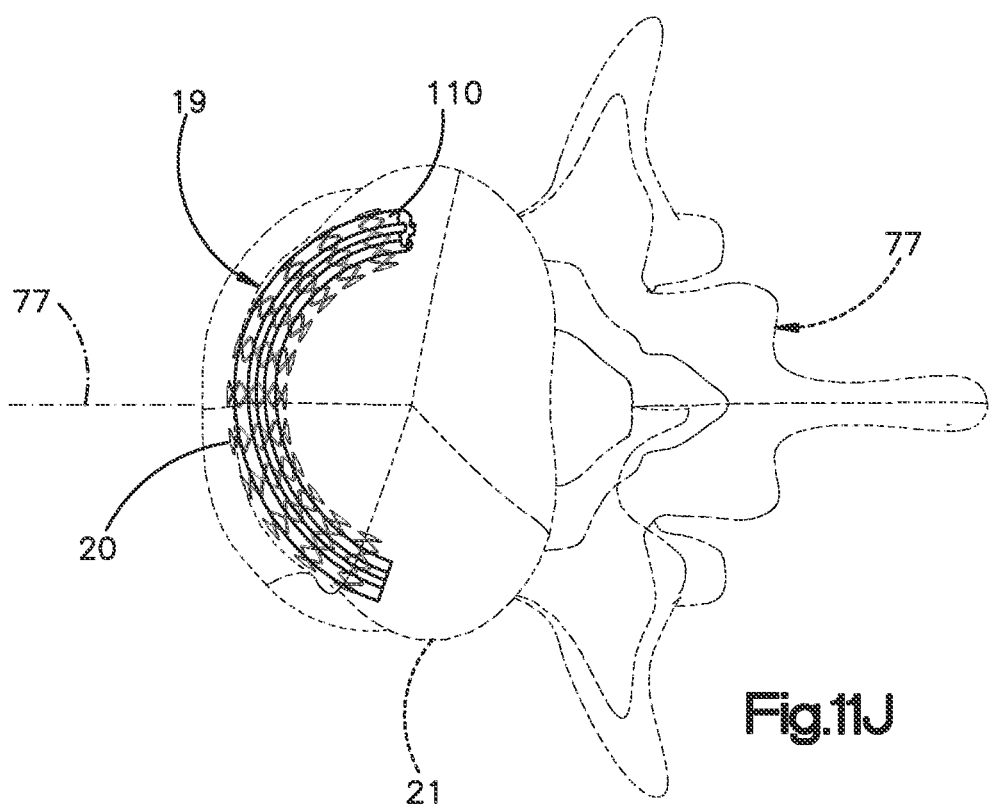
FIG. 11J is a top plan view similar to FIG. 11H, but showing the auxiliary implant expanded to its expanded configuration inside the primary implant, and showing the insertion assembly removed from the target vertebra.

As illustrated in FIG. 11J, once the auxiliary implant(s) 110 is disposed in the internal void of the primary implant 20, the proximal end of the auxiliary implant(s) 110 can be coupled to a source of bone filler material 123, such as for example a biocompatible bone cement. For instance, a secondary cannula can be inserted into the cannulated body 62a, and coupled to an inlet to the implant 110 at one end, and a pressurized source of bone filler material at its other end. Thus, the bone filler material can be injected into the implant 110, thereby causing the implant 110 to expand inside the primary implant 20 in the manner described above. Once the bone filler material hardens, the secondary cannula and the cannulated body 62a can be twisted, pried, or otherwise actuated to break away from the expanded auxiliary implant 110 and removed from the target vertebra 17, as illustrated in FIG. 11J. The resulting implant assembly 19 is positioned such that the lateral midline 77 intersects the implant assembly 19, which can be curved about a caudal-cranial axis. Thus, it can be said that the implant assembly 19 is laterally centered or at least partially laterally centered in the vertebral body 21. It can also be said that the implant assembly 19 is aligned or at least partially aligned with the lateral midline 77. In accordance with the illustrated embodiment, the implant assembly 19 is substantially centered with respect to the intervertebral discs that are adjacent and cranial and caudal with respect to the target vertebra 21. Accordingly, the implant assembly 19 can be located in the vertebral body 21 at the region of maximum load bearing, and resist the forces applied to the vertebral body 21 by the adjacent pressurized intervertebral discs, and can thus limit or prevent the intrusion of the adjacent intervertebral discs into or through the broken end plates of the fractured vertebral body 21.

Alternatively, a pair of the banana-shaped implant assemblies 19 can be inserted into the vertebral body on opposed sides of the lateral midline (see FIG. 3D) via a corresponding pair of insertion assemblies as described above with respect to FIGS. 10D-J. Alternatively still, the implant assemblies 19 can be positioned so as to abut each other (or be placed in close proximity) at the lateral midline 77 so as to provide the structural stability that limits or prevents the intervertebral discs from protruding into the vertebral body portion 21.

Figure 12A:
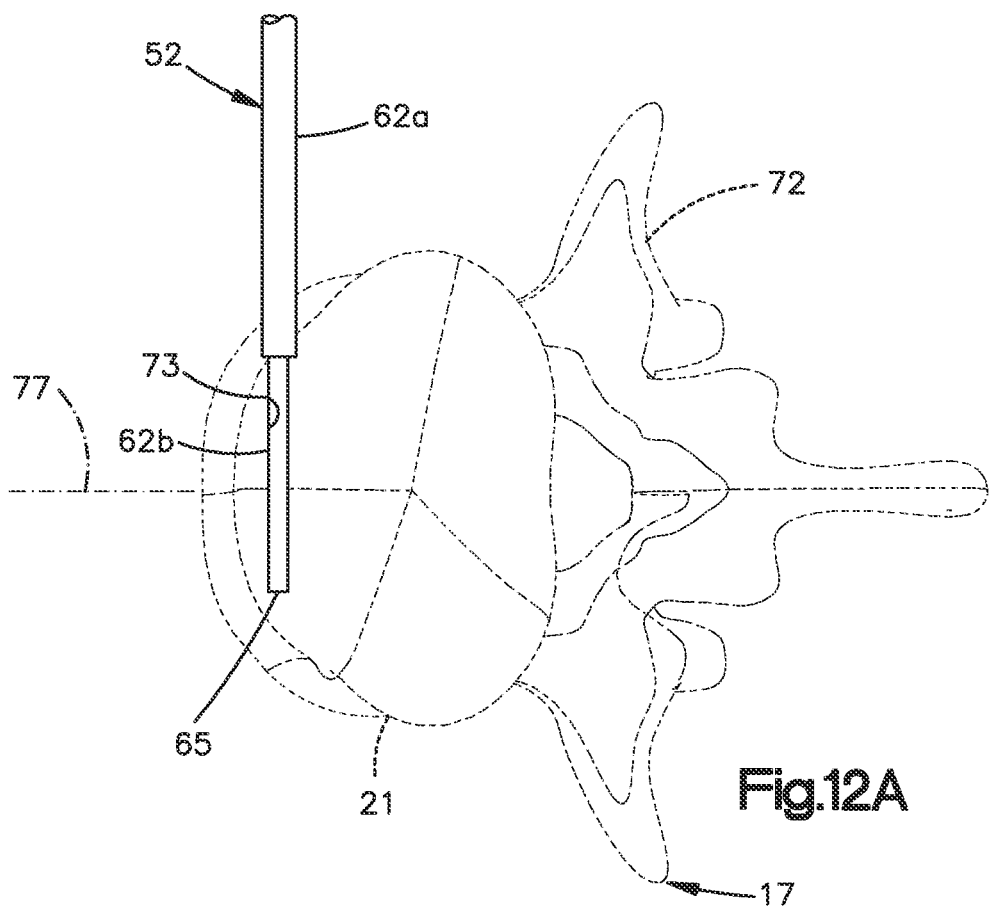
FIG. 12A is a top plan view of the insertion assembly installed in a target vertebral body via a lateral or trans-psoas approach.

Referring now to FIGS. 12A-C, the implant assembly 19 can be inserted into the vertebral body portion via a lateral or trans-psoas approach. For instance, the opening assembly 52 can be inserted laterally into the vertebral body portion 21, and the distal end 66b of the opening device 62a can be translated out from the cannulated body 62a in along a lateral direction through the cancellous bone portion of the vertebral body 21, so as to create a channel 73 in the vertebral body 21 that crosses or intersects the lateral midline 77. The primary implant 20 and the expansion body 69 can be implanted into the channel 73 and expanded, and the expansion body 69 can be deflated and removed from the vertebra 17 in the manner described above. The primary implant 20 can be substantially centered with respect to the lateral midline 77 of the vertebral body 21. The auxiliary implant 110 can then be inserted into the implant 20 and expanded, and the insertion assembly 50 can be removed in the manner described above. The auxiliary implant 110 can be symmetrical, for instance cylindrical as illustrated in FIG. 3C or cigar-shaped as illustrated in FIG. 3E. Thus, the symmetrical implant assembly 19 can be implanted laterally into the vertebral body 21, and extend substantially laterally within the vertebral body 21 at a location substantially aligned with the lateral midline 77 so as to prevent or limit intrusion of adjacent intervertebral discs into the fractured vertebral body.

Certain example embodiments have been described with respect to an expandable implant assembly that can augment an interior volume of a target bone, thereby increasing or restoring the height of the bone, filling a cavity formed in the bone and/or stabilizing, aiding and/or augmenting the bone. It should be appreciated that while the expandable implant assembly 19 has been described as used in a target bone that has been illustrated as the spine (for example, in the lumbar, thoracic or cervical regions), those skilled in the art will appreciate that the implant assembly 19 may be implanted and subsequently expanded in the manner described above in other parts of the body, for instance to augment an alternative target bone, including for example long bones such as proximal humerus and proximal tibia or bones in the hand, face, feet, extremities, cranium, or nearly any bone in the human body. Moreover, the implant assembly 19 can be used as an intervertebral spacer in a degenerated disc or in an intervertebral space after a discectomy has partially or fully removed the intervertebral disc. Furthermore, it should be appreciated that a kit can be provided that includes one or more components of the implant system 18, up to all of the components of an implant system usable to insert and expand at least one expandable implant assembly 19 in the manner described herein, including components of different sizes, shapes, and configurations.

It should be appreciated that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise precluded. It should be understood that the concepts described above with the above-described embodiments may be employed alone or in combination with any of the other embodiments described above. Those skilled in the relevant art, having the benefit of the teachings of this specification, may effect numerous modifications to the invention as described herein, and changes may be made without departing from the scope and spirit of the invention, for instance as set forth by the appended claims.

The invention claimed is:

1. An expandable implant assembly for insertion within patient anatomy, the expandable implant assembly comprising:
   a primary implant elongate along a central axis and configured to expand radially outward from the central axis, the primary implant including an inner surface that defines an internal void; and
   an auxiliary implant configured to reside in the internal void and expand radially outward from the central axis against the inner surface of the primary implant, the auxiliary implant defining a central body portion and at least first and second nodes each extending outwardly from the central body portion along respective radial directions perpendicular to the central axis, wherein each of the at least first and second nodes defines:
      a neck; and
      a foot spaced outwardly from the neck along the respective radial direction, the foot configured to abut the inner surface of the primary implant, the neck extending from the foot to a respective leg of the central body portion, the leg defining a pair of side surfaces,
   wherein, when the auxiliary implant is expanded:
      the foot defines a circumferential dimension about the central axis greater than a circumferential dimension of the neck about the central axis, and
      a circumferential width of the respective leg measured between the respective pair of side surfaces does not decrease along the leg toward the central axis.

2. The expandable implant assembly of claim 1, wherein the at least first and second nodes comprise a third node, the central body portion has a substantially triangular shape in a reference plane orthogonal to the central axis, and the respective legs define respective vertices of the central body portion.

3. The expandable implant assembly of claim 2, wherein the substantially triangular shape is substantially equilateral, and the central axis extends through the central body portion.

4. The expandable implant assembly of claim 1, wherein the auxiliary implant is insertable within the internal void of the primary implant prior to expansion of the auxiliary implant.

5. An expandable implant assembly for insertion within a target region of patient anatomy, comprising:
   a cannulated body configured to advance within the patient anatomy at least to a location adjacent the target region;
   an implant configured for insertion through the cannulated body and within the target region, the implant elongate along a central axis and configured to expand radially outward from the central axis from a first configuration to an expanded configuration, the implant defining a central body portion and at least first and second nodes each extending outwardly from the central body portion along respective radial directions perpendicular to the central axis,
      wherein each of the at least first and second nodes defines a neck and a foot spaced outwardly from the neck along the respective radial direction, the neck extending from the foot to a respective leg of the central body portion, the leg defining a pair of side surfaces, wherein, when the implant is in the expanded configuration:
   the foot defines a circumferential dimension about the central axis greater than a circumferential dimension of the neck about the central axis, and a circumferential width of the respective leg measured between the respective pair of side surfaces does not decrease along the leg toward the central axis.

6. The expandable implant assembly of claim 5, wherein the central body portion and the at least first and second nodes are configured to at least partially define at least first and second pockets that extend respectively between the at least first and second nodes.

7. The expandable implant assembly of claim 6, further comprising bone stimulating material configured to be inserted into the at least first and second pockets.

8. The expandable implant assembly of claim 5, wherein the implant comprises a body that defines an interior volume that is configured to be filled with a bone filler material so as to expand the body from the collapsed configuration to the expanded configuration.

9. The expandable implant assembly of claim 5, wherein the body of the implant is folded when in the first configuration, and the body unfolds and substantially does not stretch during expansion from the first configuration to the expanded configuration.

10. The expandable implant assembly of claim 5, wherein the implant comprises a body that defines opposed first and second sides that are elongate along respective first and second directions that are parallel with the central axis, the first side defines a first thickness, and the second side defines a second thickness less than the first thickness such that the first side is configured to be convex along the first direction and the second side is configured to be concave along the second direction when the implant is in the expanded configuration.

11. The expandable implant assembly of claim 5, wherein the implant is configured such that portions of the central axis are one or more of straight and curved when in the expanded configuration.

12. An expandable implant, comprising:
   an implant body elongate along a central axis and configured to expand radially outward from the central axis from a first configuration to an expanded configuration, the implant body defining a central body portion and first and second nodes each extending outwardly from the central body portion along respective radial directions perpendicular to the central axis,
   wherein each of the first and second nodes defines a neck and a foot spaced outwardly from the neck along the respective radial direction, the neck extending from the foot to a respective leg of the central body portion, the leg defining a pair of side surfaces,
   wherein, when the implant is in the expanded configuration:
      the foot defines a circumferential dimension about the central axis greater than a circumferential dimension of the neck about the central axis, and
      a circumferential width of the respective leg measured between the respective pair of side surfaces does not decrease along the leg toward the central axis.

13. The expandable implant of claim 12, wherein the at least first and second nodes comprise a third node, the central body portion has a substantially triangular shape in a reference plane orthogonal to the central axis, and the respective legs define respective vertices of the central body portion.

14. The expandable implant of claim 13, wherein the substantially triangular shape is substantially equilateral.

15. The expandable implant of claim 12, wherein the central body portion and the at least first and second nodes are configured to at least partially define at least first and second pockets that extend respectively between the at least first and second nodes.

16. The expandable implant of claim 15, further comprising bone stimulating material configured to be inserted into the at least first and second pockets.

17. The expandable implant of claim 12, wherein the implant body defines an interior volume that is configured to be filled with a bone filler material so as to expand the implant body from the first configuration to the expanded configuration.

18. The expandable implant of claim 12, wherein the implant body is folded when in the first configuration, and the implant body unfolds during expansion from the first configuration to the expanded configuration.

19. The expandable implant of claim 18, wherein the implant body substantially does not stretch during expansion from the first configuration to the expanded configuration.

20. The expandable implant of claim 12, wherein the implant body is configured so that the central axis is curved when in the expanded configuration, the implant body defines opposed first and second sides that are elongate along respective first and second directions that are parallel with the central axis, the first side defines a first thickness, and the second side defines a second thickness less than the first thickness such that the first side is configured to be convex along the first direction and the second side is configured to be concave along the second direction when the implant body is in the expanded configuration.

* * * * *